(12) United States Patent
Ozeki et al.

(10) Patent No.: US 8,722,868 B2
(45) Date of Patent: May 13, 2014

(54) GLYCOSYLTRANSFERASE, NOVEL GLYCOSYLTRANSFERASE GENE, AND NOVEL SUGAR DONOR COMPOUND

(75) Inventors: Yoshihiro Ozeki, Tokyo (JP); Nobuhiro Sasaki, Tokyo (JP); Kazuo Nagasawa, Tokyo (JP); Masayuki Tera, Tokyo (JP); Yuki Matsuba, Tokyo (JP); Haruka Nakamura, Tokyo (JP); Yutaka Abe, Tokyo (JP)

(73) Assignee: National University Corporation Tokyo University of Agriculture and Technology, Tokyo (JP)

( * ) Notice: Subject to any disclaimer, the term of this patent is extended or adjusted under 35 U.S.C. 154(b) by 0 days.

(21) Appl. No.: 13/389,233

(22) PCT Filed: Jan. 21, 2010

(86) PCT No.: PCT/JP2010/050674
§ 371 (c)(1),
(2), (4) Date: Feb. 6, 2012

(87) PCT Pub. No.: WO2011/016260
PCT Pub. Date: Feb. 10, 2011

(65) Prior Publication Data
US 2012/0135469 A1    May 31, 2012

(30) Foreign Application Priority Data
Aug. 7, 2009   (JP) ................... 2009-184030

(51) Int. Cl.
*C07H 21/04*    (2006.01)
*C12N 9/10*    (2006.01)
*C12N 15/00*    (2006.01)
*C12N 5/10*    (2006.01)

(52) U.S. Cl.
USPC ........ 536/23.2; 435/193; 435/320.1; 435/419

(58) Field of Classification Search
None
See application file for complete search history.

(56) References Cited

U.S. PATENT DOCUMENTS

2008/0009032 A1   1/2008   Tanaka et al.
2009/0288225 A1   11/2009   Noda et al.

FOREIGN PATENT DOCUMENTS

| EP | 1811030 | 7/2007 |
|---|---|---|
| JP | 10-113184 | 5/1998 |
| JP | 2003-289884 | 10/2003 |
| WO | 2005/059141 | 6/2005 |
| WO | 2006/046780 | 5/2006 |
| WO | 2007/046148 | 4/2007 |

OTHER PUBLICATIONS

Ogata et al., "Analysis of genes involved in the expression of carnation flower color (the third report) concerning flavonoid glucosyltransferases in the patals of the carnation," Journal of the Japanese Society for Horticultural Sciences, 2003, vol. 72, separate vol. 1, p. 358 (with English language translation).

Matsuba et al., "Enzymatic preparation of 1-O-hydroxycinnamoyl-β-D-glucose-dependent acyltransferase in anthocyanin-producing cultured cells of *Daucus carota* and *Glehnia littoralis*," Plant Biotechnology, 2008, vol. 25, No. 4, pp. 369-375.

Yamazaki et al., Molecular cloning and biochemical characterization of a novel anthocyanin 5-O-glucosyltransferase by mRNA differential display for plant forms regarding anthocyanin, The Journal of Biological Chemistry, 1999, vol. 274, No. 11, pp. 7405-7411.

Li et al., "Phylogenetic analysis of UDP-glycosyltransferase multigene family of *Arabidopsis thaliana*," The Journal of Biological Chemistry, 2001, vol. 276, No. 6, pp. 4338-4343.

Lunkenbein S et al., "Cinnamate metabolism in ripening fruit: Characterization of an UDP-glucose: cinnamate glucosyltransferase from strawberry (*Fragaria x ananassa*)", Plant Physiology, American Society of Plant Physiologists, Jan. 27, 2006, vol. 140, pp. 1-38.

*Primary Examiner* — Tekchand Saidha
*Assistant Examiner* — MD. Younus Meah
(74) *Attorney, Agent, or Firm* — Hamre, Schumann, Mueller & Larson, P.C.

(57) ABSTRACT

An object of the present invention is to provide a sugar donating reagent comprising a sugar donor compound other than a sugar nucleotide and an enzyme capable of catalyzing a glycosyl transfer reaction using a sugar donor compound other than a sugar nucleotide. The present invention provides the following: a sugar donating reagent containing a compound of formula (A):

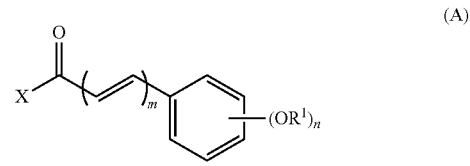

(A)

wherein $R^1$ is independently selected from hydrogen, or $C_{1-6}$ alkyl, $C_{2-6}$ alkenyl, and $C_{2-6}$ alkynyl in which each of the groups is unsubstituted or substituted with one or more groups selected from OH, F, Cl, Br, I, CN, $NO_2$, and $SO_2$, n is 0, 1, 2, 3, 4 or 5, m is 0 or 1, and X represents a monosaccharide bound via a β bond on its anomeric carbon; a glycosyltransferase capable of catalyzing a glycosyl transfer reaction using the sugar donor; and a glycosyltransferase gene comprising DNA encoding the glycosyltransferase.

14 Claims, 12 Drawing Sheets
(2 of 12 Drawing Sheet(s) Filed in Color)

SEQUENCE LISTING

<160> NUMBER OF SEQ ID NOS: 28

<210> SEQ ID NO 1
<211> LENGTH: 502
<212> TYPE: PRT
<213> ORGANISM: Dianthus caryophyllus

<400> SEQUENCE: 1

Met Asn Met Ser Cys Lys Phe Glu Ile Val Leu Leu Val Ser Trp Trp
1               5                   10                  15

Leu Leu Leu Val Leu Val Phe Gly Val Glu Ser Ser Met Phe Ser Glu
            20                  25                  30

Phe Asp Arg Leu Asp Phe Pro Lys His Phe Ile Phe Gly Ala Ser Ser
        35                  40                  45

Cys Ala Tyr Gln Val Glu Gly Ala Ala Phe Glu Asp Gly Arg Thr Leu
    50                  55                  60

Ser Thr Phe Asp Ile Ala Ala His Ser Gly His Leu Pro Gly Asn Gly
65                  70                  75                  80

Asp Ile Thr Ser Asp Glu Tyr His Lys Tyr Lys Glu Asp Val Glu Leu
                85                  90                  95

Met Val Glu Thr Gly Leu Asp Ala Tyr Arg Phe Ser Ile Ser Trp Ser
            100                 105                 110

Arg Leu Ile Pro Asn Gly Arg Pro Val Asn Pro Lys Gly Leu Glu
            115                 120                 125

Tyr Tyr Asn Asn Leu Val Asn Ala Leu Leu Thr Lys Gly Thr Gln Pro
130                 135                 140

His Val Thr Leu Leu His Ser Asp Leu Pro Gln Ala Leu Arg Asp Glu
145                 150                 155                 160

Tyr Gly Gly Leu Phe Ile Ser Pro Lys Phe Ile Asp Asp Phe Val Ala
                165                 170                 175

Tyr Ala Asp Val Cys Phe Arg Glu Phe Gly Asp Arg Val Leu His Trp
            180                 185                 190

Thr Thr Phe Asn Glu Ala Asn Phe Leu Ala Phe Gly Asp Glu Asn Thr
        195                 200                 205

Pro Ala Ser Ala Leu Tyr Leu Ser Ala His His Leu Leu Ala His
210                 215                 220

Ala Ser Ala Thr Arg Leu Tyr Arg Glu Asn Tyr Gln Ala Ser Gln Arg
225                 230                 235                 240

Gly Phe Ile Gly Ile Asn Val Tyr Ala Tyr Asp Phe Ile Pro Glu Thr
                245                 250                 255

Asn Thr Glu Val Asp Val Ile Ala Ala Lys Arg Ala Arg Asp Phe Phe
            260                 265                 270

Ile Gly Trp Phe Val Gln Pro Leu Met Asn Gly Glu Tyr Pro Leu Thr
275                 280                 285

Met Arg Lys Asn Gly Gly Pro Arg Leu Pro Lys Phe Thr Pro Asn Glu
290                 295                 300

Thr Glu Leu Leu Thr Gly Ser Tyr Asp Phe Ile Gly Leu Asn Tyr Tyr
305                 310                 315                 320

Thr Ala Lys Thr Val Lys Asp Asp Pro Val Met Leu Thr Val Glu Pro
                325                 330                 335

Arg Asn Tyr Tyr Thr Asp Gln Gly Leu Ile Ser Ser Tyr Leu Gly Asn
            340                 345                 350

Ile Asp Pro Tyr Gln Gly His Pro Phe Phe Asn Thr Pro Trp Gly Leu
        355                 360                 365

His Asp Val Leu Gln Gln Phe Lys Gln Val Tyr Gly Asn Pro Pro Val
370                 375                 380

Tyr Ile His Glu Asn Gly Glu Val Gly Asp His Asp Ala Asp Tyr Asp
385                 390                 395                 400

Lys Leu Ile Asn Asp Ile Pro Arg Val Glu Tyr Leu Gln Gly His Ile
                405                 410                 415

Arg Ala Val Leu Asp Ala Val Arg Asn Gly Ser Asn Val Lys Gly Tyr
            420                 425                 430

Phe Val Trp Ser Phe Leu Asp Met Tyr Glu Leu Met Tyr Gly Thr Lys
        435                 440                 445

Phe Thr Phe Gly Leu Tyr Tyr Ile Asp Phe Asn Asp Pro Lys Leu Thr
450                 455                 460

Arg His Pro Lys Leu Ser Gln Lys Trp Tyr Ser Arg Phe Leu Lys Gly
465                 470                 475                 480

Glu Lys Ala Ser Thr Lys Ala Ser Ile His Thr Pro Asn Glu Ala Glu
                485                 490                 495

Thr His Thr Tyr Phe Tyr
            500

<210> SEQ ID NO 2
<211> LENGTH: 1764
<212> TYPE: DNA
<213> ORGANISM: Dianthus caryophyllus

```
<220> FEATURE:
<221> NAME/KEY: CDS
<222> LOCATION: (73)..(1578)

<400> SEQUENCE: 2
gagaaaacac tcgggagagt atataaatag gagggagttt actccaaaga agaaagcaat      60
aatatagtga aa atg aac atg tca tgc aag ttt gaa att gta tta ttg gtt    111
            Met Asn Met Ser Cys Lys Phe Glu Ile Val Leu Leu Val
              1               5                  10 tca tgg tgg ttg tta cta gta cta gtt ttt ggt gtg gaa agt agc atg      159
Ser Trp Trp Leu Leu Leu Val Leu Val Phe Gly Val Glu Ser Ser Met
 15                  20                  25 ttt tcg gag ttt gac cgc ctt gac ttt cct aag cac ttc atc ttt ggt      207
Phe Ser Glu Phe Asp Arg Leu Asp Phe Pro Lys His Phe Ile Phe Gly
 30                  35                  40                  45 gct tcc tct tgt gct tat cag gtc gag gga gcg gct ttt gag gat gga      255
Ala Ser Ser Cys Ala Tyr Gln Val Glu Gly Ala Ala Phe Glu Asp Gly
                     50                  55                  60 agg aca ctg agt act ttt gat att gca gct cac tct ggt cat ttg cca      303
Arg Thr Leu Ser Thr Phe Asp Ile Ala Ala His Ser Gly His Leu Pro
 65                  70                  75 ggc aac gga gac ata acg tcc gat gaa tat cac aaa tat aag gaa gat      351
Gly Asn Gly Asp Ile Thr Ser Asp Glu Tyr His Lys Tyr Lys Glu Asp
             80                  85                  90 gtc gaa ctc atg gtg gaa aca gga ttg gat gca tac cgc ttt tcc ata      399
Val Glu Leu Met Val Glu Thr Gly Leu Asp Ala Tyr Arg Phe Ser Ile
 95                 100                 105 tcg tgg tcg aga ctg ata ccg aat ggt aga gga cct gtt aat ccg aag      447
Ser Trp Ser Arg Leu Ile Pro Asn Gly Arg Gly Pro Val Asn Pro Lys
110                 115                 120                 125 ggt ttg gag tat tat aac aac ctc gtc aat gca ctc ctc acc aaa ggt      495
Gly Leu Glu Tyr Tyr Asn Asn Leu Val Asn Ala Leu Leu Thr Lys Gly
                    130                 135                 140 acc caa cca cat gtt aca ctg ctg cat tcc gat tta cct cag gca ctt      543
Thr Gln Pro His Val Thr Leu Leu His Ser Asp Leu Pro Gln Ala Leu
                145                 150                 155 aga gat gag tac ggt gga tta ttc atc agc cca aag ttt att gac gac      591
Arg Asp Glu Tyr Gly Gly Leu Phe Ile Ser Pro Lys Phe Ile Asp Asp
            160                 165                 170 ttt gtg gcg tac gct gat gtt tgc ttt aga gag ttt ggc gac agg gtt      639
Phe Val Ala Tyr Ala Asp Val Cys Phe Arg Glu Phe Gly Asp Arg Val
            175                 180                 185 ttg cat tgg acg aca ttc aat gag gcc aac ttt tta gcc ttt ggt gac      687
Leu His Trp Thr Thr Phe Asn Glu Ala Asn Phe Leu Ala Phe Gly Asp
190                 195                 200                 205 gag aat aca ccc gct tct gca tta tac ctg tca gct cac cat ctg ttg      735
Glu Asn Thr Pro Ala Ser Ala Leu Tyr Leu Ser Ala His His Leu Leu
                    210                 215                 220 ttg gct cac gcg tct gct aca agg ctc tac cga gaa aat tac cag gca      783
Leu Ala His Ala Ser Ala Thr Arg Leu Tyr Arg Glu Asn Tyr Gln Ala
                225                 230                 235 agt caa cgt gga ttt ata ggg atc aat gtg tac gcg tat gat ttc att      831
Ser Gln Arg Gly Phe Ile Gly Ile Asn Val Tyr Ala Tyr Asp Phe Ile
            240                 245                 250 ccg gaa aca aat aca gaa gtt gac gtt att gcg gca aag cgt gcc cgt      879
Pro Glu Thr Asn Thr Glu Val Asp Val Ile Ala Ala Lys Arg Ala Arg
            255                 260                 265 gat ttc ttc att ggt tgg ttc gtg caa ccc ttg atg aac gga gag tat      927
Asp Phe Phe Ile Gly Trp Phe Val Gln Pro Leu Met Asn Gly Glu Tyr
270                 275                 280                 285
```

```
cct tta aca atg agg aag aat ggt ggc ccc cga ctt cca aag ttc acg      975
Pro Leu Thr Met Arg Lys Asn Gly Gly Pro Arg Leu Pro Lys Phe Thr
                290                 295                 300 cca aac gaa acg gag ctc ctc acg gga tcc tat gat ttt atc gga ctg     1023
Pro Asn Glu Thr Glu Leu Leu Thr Gly Ser Tyr Asp Phe Ile Gly Leu
            305                 310                 315 aat tat tac acc gcc aaa aca gtg aaa gac gac cct gtc atg ctc act     1071
Asn Tyr Tyr Thr Ala Lys Thr Val Lys Asp Asp Pro Val Met Leu Thr
        320                 325                 330 gtg gaa ccg aga aat tat tac act gac cag gga cta ata tcg tca tat     1119
Val Glu Pro Arg Asn Tyr Tyr Thr Asp Gln Gly Leu Ile Ser Ser Tyr
    335                 340                 345 cta ggc aac att gat ccg tat caa ggg cat cca ttc ttc aat acg ccg     1167
Leu Gly Asn Ile Asp Pro Tyr Gln Gly His Pro Phe Phe Asn Thr Pro
350                 355                 360                 365 tgg ggg ctt cat gat gta ctc caa caa ttc aag caa gtt tac ggc aat     1215
Trp Gly Leu His Asp Val Leu Gln Gln Phe Lys Gln Val Tyr Gly Asn
                370                 375                 380 cct ccc gtc tat ata cac gag aat ggt gaa gtc ggt gat cac gat gca     1263
Pro Pro Val Tyr Ile His Glu Asn Gly Glu Val Gly Asp His Asp Ala
            385                 390                 395 gat tac gat aaa tta att aat gac ata cct cgt gtc gag tat tta caa     1311
Asp Tyr Asp Lys Leu Ile Asn Asp Ile Pro Arg Val Glu Tyr Leu Gln
        400                 405                 410 ggt cac atc aga gct gtg ctc gat gca gta aga aat gga tcg aat gtg     1359
Gly His Ile Arg Ala Val Leu Asp Ala Val Arg Asn Gly Ser Asn Val
    415                 420                 425 aaa ggg tac ttc gtg tgg tcg ttc tta gat atg tat gag ctg atg tac     1407
Lys Gly Tyr Phe Val Trp Ser Phe Leu Asp Met Tyr Glu Leu Met Tyr
430                 435                 440                 445 ggg aca aaa ttt aca ttt ggc cta tac tac atc gat ttt aat gac ccg     1455
Gly Thr Lys Phe Thr Phe Gly Leu Tyr Tyr Ile Asp Phe Asn Asp Pro
                450                 455                 460 aaa tta acc aga cat ccg aag ctg tcg caa aaa tgg tac tcg agg ttt     1503
Lys Leu Thr Arg His Pro Lys Leu Ser Gln Lys Trp Tyr Ser Arg Phe
            465                 470                 475 ttg aaa ggc gag aag gcg agc acg aaa gcg agt ata cac act cca aat     1551
Leu Lys Gly Glu Lys Ala Ser Thr Lys Ala Ser Ile His Thr Pro Asn
        480                 485                 490 gaa gca gaa aca cat acg tac ttc tac tgacagatct actatctaga           1598
Glu Ala Glu Thr His Thr Tyr Phe Tyr
    495                 500 ctcggaggtt tggggtgcg aaaaaaaaaa taataataat gttatggtgt actaagcaag    1658
taagcagata acccgtctta agtaagactt attggtacta taaatatagt caaagttgat   1718
ttttaaagtg gtaataaaat tatcttttgg taaaaaaaaa aaaaaa                  1764

<210> SEQ ID NO 3
<211> LENGTH: 505
<212> TYPE: PRT
<213> ORGANISM: Delphinium grandiflorum L.

<400> SEQUENCE: 3

Met Cys Pro Ser Phe Leu Val Thr Leu Leu Leu Gln Leu Ser Ser
1               5                   10                  15

Leu Val Val Val Leu Val Val Trp Ala Glu Gln Leu Pro Glu Phe Asn
                20                  25                  30

Val Arg Arg Asp Asp Phe Pro Ser Asn Phe Val Phe Gly Ala Gly Thr
            35                  40                  45

Ser Ala Leu Gln Val Glu Gly Ala Ile Ala Glu Asp Gly Lys Thr Pro
```

```
                50                  55                  60
Asn Ile Trp Asp Val Asp Ser His Met Gly His Met Pro Asp Lys Ser
65                  70                  75                  80

Thr Thr Asp Ile Ala Cys Asp Ser Tyr His Arg Tyr Lys Glu Asp Val
                85                  90                  95

Lys Ile Met Ser Asp Ile Gly Leu Glu Ala Tyr Arg Phe Ser Ile Ala
                100                 105                 110

Trp Thr Arg Ile Leu Pro Tyr Gly Arg Gly Phe Ile Asn Pro Lys Gly
                115                 120                 125

Val Glu Tyr Tyr Asn Asn Leu Ile Asp Thr Leu Leu Glu His Gly Ile
                130                 135                 140

Gln Pro His Ala Thr Ile Tyr His Ile Asp His Pro Gln Ile Leu Glu
145                 150                 155                 160

Asp Glu Tyr Gly Gly Trp Leu Ser Pro Arg Met Ile Glu Asp Phe Thr
                165                 170                 175

Thr Tyr Ala Asp Val Cys Phe Arg Glu Phe Gly Asp Arg Val Ser His
                180                 185                 190

Trp Thr Thr Ile Asn Glu Pro Asn Ile Ile Ser Leu Gly Ala Tyr Asp
                195                 200                 205

Ser Gly Gln Ile Pro Pro His Arg Cys Thr Pro Pro Gly Ala Tyr Asn
                210                 215                 220

Cys Thr Ala Gly Asn Ser Ser Val Glu Pro Tyr Lys Ala Met His His
225                 230                 235                 240

Phe Leu Leu Ala His Ala Ser Ala Val Gln Ile Tyr Arg Thr Lys Tyr
                245                 250                 255

Gln Ala Lys Gln Lys Gly Leu Ile Gly Leu Asn Val Tyr Gly Phe Trp
                260                 265                 270

Cys Ala Pro Gln Thr Asn Ser Arg Ala Asp Ile Glu Ala Thr Lys Arg
                275                 280                 285

Ala Thr Ala Phe Tyr Thr Gly Trp Ala Ala Asp Pro Leu Val Phe Gly
                290                 295                 300

Asp Tyr Pro Ile Ile Met Lys Glu Asn Val Gly Ser Arg Leu Pro Ser
305                 310                 315                 320

Phe Thr Lys Asn Glu Ser Glu Leu Val Lys Gly Ser Phe Asp Phe Ile
                325                 330                 335

Gly Leu Asn His Tyr Phe Val Phe Tyr Ile Gln Asp Asp Pro Glu Glu
                340                 345                 350

Ile Thr Thr Pro Ile Ser Leu Arg Asn Phe Asp Ser Asp Met Arg Val
                355                 360                 365

Lys Ala Ser Val Lys Pro Gly Asp Ser Asp Pro Ser Gly Leu Lys
370                 375                 380

Asn Leu Leu Arg Tyr Phe Lys Asp Asn Tyr Gly Asn Pro Pro Val Tyr
385                 390                 395                 400

Val His Glu Asn Gly Phe Gly Ser Pro Gln Asn Glu Thr Leu Asp Asp
                405                 410                 415

Asp Met Gly Arg Ile Arg Tyr Ile Ser Gly Tyr Ile Gly Ser Met Leu
                420                 425                 430

Glu Ala Ile Lys Asn Gly Ser Asp Thr Arg Gly Tyr Phe Val Trp Ser
                435                 440                 445

Phe Met Asp Ala Phe Glu Ile Leu Ser Gly Tyr Gln Thr Arg Tyr Gly
                450                 455                 460

Ile Val His Val Asp Phe Asp Asp Lys Ser Leu Lys Arg Gln Leu Lys
465                 470                 475                 480
```

```
Pro Ser Ala Gln Trp Tyr Ser Asn Phe Ile Lys Lys Asn Thr Thr
            485                 490                 495
Glu Asp Glu Ile Ser Tyr Ser Ser Gln
            500                 505

<210> SEQ ID NO 4
<211> LENGTH: 1714
<212> TYPE: DNA
<213> ORGANISM: Delphinium grandiflorum L.
<220> FEATURE:
<221> NAME/KEY: CDS
<222> LOCATION: (28)..(1542)

<400> SEQUENCE: 4
gaaaataaaa aggtgactag tttcaaa atg tgc ccc tct ttt cta gtg act ctt         54
                            Met Cys Pro Ser Phe Leu Val Thr Leu
                              1               5 ctt ctt ctc cag ctt agt agt cta gtg gtg gta cta gtt gtt tgg gca        102
Leu Leu Leu Gln Leu Ser Ser Leu Val Val Val Leu Val Val Trp Ala
 10              15                  20                  25 gaa caa ttg ccc gaa ttt aat gtc aga aga gat gat ttc cca tct aac        150
Glu Gln Leu Pro Glu Phe Asn Val Arg Arg Asp Asp Phe Pro Ser Asn
             30                  35                  40 ttt gtg ttc ggc gct ggt act tca gct ctt cag gtt gaa ggg gcc att        198
Phe Val Phe Gly Ala Gly Thr Ser Ala Leu Gln Val Glu Gly Ala Ile
         45                  50                  55 gca gaa gat gga aaa aca cct aat atc tgg gac gtc gac agt cat atg        246
Ala Glu Asp Gly Lys Thr Pro Asn Ile Trp Asp Val Asp Ser His Met
     60                  65                  70 ggg cat atg ccg gac aag agc acc aca gat ata gct tgc gat tca tac        294
Gly His Met Pro Asp Lys Ser Thr Thr Asp Ile Ala Cys Asp Ser Tyr
 75                  80                  85 cac aga tat aag gaa gat gtg aag ata atg agt gat ata gga ctc gaa        342
His Arg Tyr Lys Glu Asp Val Lys Ile Met Ser Asp Ile Gly Leu Glu
 90                  95                 100                 105 gct tat cga ttt tcc att gca tgg acc aga att ctt cca tat ggg aga        390
Ala Tyr Arg Phe Ser Ile Ala Trp Thr Arg Ile Leu Pro Tyr Gly Arg
            110                 115                 120 gga ttc atc aat cca aaa ggg gtc gag tat tat aac aat ctc atc gac        438
Gly Phe Ile Asn Pro Lys Gly Val Glu Tyr Tyr Asn Asn Leu Ile Asp
            125                 130                 135 aca ctg ttg gaa cat gga att caa cca cat gct aca ata tac cat ata        486
Thr Leu Leu Glu His Gly Ile Gln Pro His Ala Thr Ile Tyr His Ile
            140                 145                 150 gat cac cct cag ata ctt gaa gat gaa tac gga gga tgg tta agc ccg        534
Asp His Pro Gln Ile Leu Glu Asp Glu Tyr Gly Gly Trp Leu Ser Pro
        155                 160                 165 aga atg atc gag gac ttc acc acc tac gca gat gta tgt ttt aga gag        582
Arg Met Ile Glu Asp Phe Thr Thr Tyr Ala Asp Val Cys Phe Arg Glu
170                 175                 180                 185 ttt ggc gac agg gtt tcg cac tgg aca acc atc aac gaa cct aac ata        630
Phe Gly Asp Arg Val Ser His Trp Thr Thr Ile Asn Glu Pro Asn Ile
                190                 195                 200 ata agc ttg ggg gct tac gac agt ggt cag att cca ccc cat cga tgt        678
Ile Ser Leu Gly Ala Tyr Asp Ser Gly Gln Ile Pro Pro His Arg Cys
            205                 210                 215 acg ccc cca ggt gcc tac aac tgt aca gct ggt aac tca tcc gtc gaa        726
Thr Pro Pro Gly Ala Tyr Asn Cys Thr Ala Gly Asn Ser Ser Val Glu
            220                 225                 230 cct tac aaa gca atg cac cat ttc ttg cta gcc cat gcg tct gct gtg        774
Pro Tyr Lys Ala Met His His Phe Leu Leu Ala His Ala Ser Ala Val
        235                 240                 245
```

-continued

```
caa atc tac agg aca aaa tac cag gct aag cag aaa ggt ttg ata ggg      822
Gln Ile Tyr Arg Thr Lys Tyr Gln Ala Lys Gln Lys Gly Leu Ile Gly
250                 255                 260                 265 ctc aat gtg tac ggt ttc tgg tgt gca cct cag aca aac tcg agg gca      870
Leu Asn Val Tyr Gly Phe Trp Cys Ala Pro Gln Thr Asn Ser Arg Ala
                270                 275                 280 gat att gaa gca acc aaa aga gcc aca gct ttc tac act ggc tgg gct      918
Asp Ile Glu Ala Thr Lys Arg Ala Thr Ala Phe Tyr Thr Gly Trp Ala
            285                 290                 295 gct gat ccc ctc gtt ttc ggg gac tat cca ata atc atg aaa gag aat      966
Ala Asp Pro Leu Val Phe Gly Asp Tyr Pro Ile Ile Met Lys Glu Asn
        300                 305                 310 gtt ggc tcc aga ctt cca tcg ttt acc aag aac gag tcc gag ctt gta     1014
Val Gly Ser Arg Leu Pro Ser Phe Thr Lys Asn Glu Ser Glu Leu Val
    315                 320                 325 aaa ggg tca ttt gac ttt att ggg ctg aac cat tat ttc gta ttt tac     1062
Lys Gly Ser Phe Asp Phe Ile Gly Leu Asn His Tyr Phe Val Phe Tyr
330                 335                 340                 345 ata caa gat gac cct gaa gag att aca aca cca att agc ctg aga aat     1110
Ile Gln Asp Asp Pro Glu Glu Ile Thr Thr Pro Ile Ser Leu Arg Asn
                350                 355                 360 ttc gat agt gac atg cgt gtc aaa gct tca gtt aag cca ggg gac tct     1158
Phe Asp Ser Asp Met Arg Val Lys Ala Ser Val Lys Pro Gly Asp Ser
            365                 370                 375 ggt gat cca tct ggt tta aag aac ctg ctt cga tat ttc aag gac aac     1206
Gly Asp Pro Ser Gly Leu Lys Asn Leu Leu Arg Tyr Phe Lys Asp Asn
        380                 385                 390 tat gga aat cct cct gtc tat gtt cat gag aat gga ttt ggg tcg ccg     1254
Tyr Gly Asn Pro Pro Val Tyr Val His Glu Asn Gly Phe Gly Ser Pro
    395                 400                 405 caa aat gag aca ctt gat gac gac atg ggc agg atc cgg tac ata agc     1302
Gln Asn Glu Thr Leu Asp Asp Asp Met Gly Arg Ile Arg Tyr Ile Ser
410                 415                 420                 425 ggc tac ata gga agc atg ctt gaa gca atc aag aat gga tca gac aca     1350
Gly Tyr Ile Gly Ser Met Leu Glu Ala Ile Lys Asn Gly Ser Asp Thr
                430                 435                 440 aga gga tat ttt gtg tgg tcg ttc atg gac gct ttt gag att cta agt     1398
Arg Gly Tyr Phe Val Trp Ser Phe Met Asp Ala Phe Glu Ile Leu Ser
            445                 450                 455 gga tac caa acc cgg tat ggg att gtt cac gtc gac ttt gat gat aag     1446
Gly Tyr Gln Thr Arg Tyr Gly Ile Val His Val Asp Phe Asp Asp Lys
        460                 465                 470 agt ttg aag aga cag ctc aag cca tca gcc cag tgg tat tcc aac ttc     1494
Ser Leu Lys Arg Gln Leu Lys Pro Ser Ala Gln Trp Tyr Ser Asn Phe
    475                 480                 485 atc aag aag aag aac aca aca gag gat gag ata tcg tac tct tca cag     1542
Ile Lys Lys Lys Asn Thr Thr Glu Asp Glu Ile Ser Tyr Ser Ser Gln
490                 495                 500                 505 tagtatagga tggttgggaa tatagtttgt tgctataaca tgaaattcag gtgtatgaag   1602
tttgtccaat aagatcaaca actattgcag ttgatattac attgacatgt ggtagactgt   1662
aaacatttat aatggtatct aagtatcatt aaatacacca aaaaaaaaaa aa           1714
```

<210> SEQ ID NO 5
<211> LENGTH: 11
<212> TYPE: PRT
<213> ORGANISM: Dianthus caryophyllus

<400> SEQUENCE: 5

Gly Leu Glu Tyr Tyr Asn Asn Leu Val Asn Ala

```
1               5                   10
```

<210> SEQ ID NO 6
<211> LENGTH: 10
<212> TYPE: PRT
<213> ORGANISM: Dianthus caryophyllus

<400> SEQUENCE: 6

```
Gly Thr Gln Pro His Val Thr Leu Leu His
1               5                   10
```

<210> SEQ ID NO 7
<211> LENGTH: 11
<212> TYPE: PRT
<213> ORGANISM: Dianthus caryophyllus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 7

```
Phe Thr Pro Xaa Glu Thr Glu Leu Leu Thr Gly
1               5                   10
```

<210> SEQ ID NO 8
<211> LENGTH: 10
<212> TYPE: PRT
<213> ORGANISM: Dianthus caryophyllus

<400> SEQUENCE: 8

```
Ser Glu Phe Asp Arg Leu Asp Phe Pro Lys
1               5                   10
```

<210> SEQ ID NO 9
<211> LENGTH: 10
<212> TYPE: PRT
<213> ORGANISM: Dianthus caryophyllus

<400> SEQUENCE: 9

```
Glu Phe Asp Arg Leu Asp Phe Pro Lys His
1               5                   10
```

<210> SEQ ID NO 10
<211> LENGTH: 10
<212> TYPE: PRT
<213> ORGANISM: Dianthus caryophyllus

<400> SEQUENCE: 10

```
Pro Ser Glu Phe Asp Arg Leu Asp Phe Pro
1               5                   10
```

<210> SEQ ID NO 11
<211> LENGTH: 20
<212> TYPE: DNA
<213> ORGANISM: Dianthus caryophyllus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature

```
<222> LOCATION: (18)..(18)
<223> OTHER INFORMATION: n is a, c, g, or t

<400> SEQUENCE: 11
ggnacncarc cncaygtnac                                        20

<210> SEQ ID NO 12
<211> LENGTH: 20
<212> TYPE: DNA
<213> ORGANISM: Dianthus caryophyllus
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 12
ttyacnccng aygaracnga                                        20

<210> SEQ ID NO 13
<211> LENGTH: 25
<212> TYPE: DNA
<213> ORGANISM: Dianthus caryophyllus

<400> SEQUENCE: 13
ggaagtcggg ggccaccatt cttcc                                  25

<210> SEQ ID NO 14
<211> LENGTH: 28
<212> TYPE: DNA
<213> ORGANISM: Dianthus caryophyllus

<400> SEQUENCE: 14
atgaacatgt catgcaagtt tgaaattg                               28

<210> SEQ ID NO 15
<211> LENGTH: 28
<212> TYPE: DNA
<213> ORGANISM: Dianthus caryophyllus

<400> SEQUENCE: 15
atgtcggagt ttgaccgcct tgactttc                               28

<210> SEQ ID NO 16
<211> LENGTH: 17
<212> TYPE: DNA
<213> ORGANISM: Dianthus caryophyllus

<400> SEQUENCE: 16
gtagaagtac gtatgtg                                           17

<210> SEQ ID NO 17
<211> LENGTH: 25
<212> TYPE: DNA
<213> ORGANISM: Delphinium grandiflorum L.

<400> SEQUENCE: 17
ctggttgctt caatatctgc cctcg                                  25
```

```
<210> SEQ ID NO 18
<211> LENGTH: 25
<212> TYPE: DNA
<213> ORGANISM: Delphinium grandiflorum L.

<400> SEQUENCE: 18
atgtgcccct cttttctagt gactc                                              25

<210> SEQ ID NO 19
<211> LENGTH: 20
<212> TYPE: DNA
<213> ORGANISM: Delphinium grandiflorum L.

<400> SEQUENCE: 19
atgcccgaat ttaatgtcag                                                    20

<210> SEQ ID NO 20
<211> LENGTH: 19
<212> TYPE: DNA
<213> ORGANISM: Delphinium grandiflorum L.

<400> SEQUENCE: 20
ctgtgaagag tacgatatc                                                     19

<210> SEQ ID NO 21
<211> LENGTH: 23
<212> TYPE: DNA
<213> ORGANISM: Dianthus caryophyllus

<400> SEQUENCE: 21
ggcacccacg acaccaccat ccc                                                23

<210> SEQ ID NO 22
<211> LENGTH: 23
<212> TYPE: DNA
<213> ORGANISM: Dianthus caryophyllus

<400> SEQUENCE: 22
caggattgtc caagattaga gtc                                                23

<210> SEQ ID NO 23
<211> LENGTH: 22
<212> TYPE: DNA
<213> ORGANISM: Dianthus caryophyllus

<400> SEQUENCE: 23
gagggagttt actccaaaga ag                                                 22

<210> SEQ ID NO 24
<211> LENGTH: 22
<212> TYPE: DNA
<213> ORGANISM: Dianthus caryophyllus

<400> SEQUENCE: 24
caccatgagt tcgacatctt cc                                                 22

<210> SEQ ID NO 25
<211> LENGTH: 25
<212> TYPE: DNA
<213> ORGANISM: Dianthus caryophyllus

<400> SEQUENCE: 25
ccctattgag cacggtatcg tcacc                                              25
```

```
<210> SEQ ID NO 26
<211> LENGTH: 25
<212> TYPE: DNA
<213> ORGANISM: Dianthus caryophyllus

<400> SEQUENCE: 26
cagcacttgt ggtgagggag taacc                                              25

<210> SEQ ID NO 27
<211> LENGTH: 23
<212> TYPE: DNA
<213> ORGANISM: Dianthus caryophyllus

<400> SEQUENCE: 27
atggaggagg ataaacaaaa gcc                                                23

<210> SEQ ID NO 28
<211> LENGTH: 22
<212> TYPE: DNA
<213> ORGANISM: Dianthus caryophyllus

<400> SEQUENCE: 28
atgtgaagta acttcttcaa ta                                                 22
```

GLYCOSYLTRANSFERASE, NOVEL GLYCOSYLTRANSFERASE GENE, AND NOVEL SUGAR DONOR COMPOUND

TECHNICAL FIELD

The present invention relates to a novel glycosyltransferase, a glycosyltransferase gene consisting of DNA encoding the glycosyltransferase, and the use thereof. In addition, the present invention relates to a novel sugar donor compound used for a glycosyl transfer reaction.

BACKGROUND ART

In general, a glycosylated compound obtained by glycosylating a certain compound is likely to have improved stability and solubility compared with the corresponding unglycosylated compound. Therefore, glycosyl transfer reactions for glycosylation of various compounds have been actively studied. In addition, glycosyl transfer reactions can be applied to sugar chain synthesis. Thus, the glycosyl transfer reaction is one of highlighted research themes.

There is a known glycosyl transfer reaction observed in nature, which is involved in color development of plant petals or fruits. For example, Patent Literature 1 describes a method comprising incorporating a morning-glory-derived gene into a different plant so as to transfer glucose to sugar moiety of a flavonoid having the sugar at the 3 position, thereby providing a flower having a color different from a natural plant.

There are many known glycosyl transfer reactions in which a sugar nucleotide such as UDP-glucose is used as a sugar donor. For example, Non-Patent Literature 1 describes that UDP-glucose:anthocyanidin 5-glycosyltransferase derived from Japanese basil, verbena, or the like catalyzes a reaction of transferring a sugar to a hydroxy group at the 5 position of anthocyanidin with the use of UDP-glucose as a sugar donor. Non-Patent Literature 2 describes that UDP-glucose:flavonoid 3-glycosyltransferase from Japanese basil, maize (*Zea mays*), gentian, grape, or the like catalyses a reaction of transferring a sugar to a hydroxy group at the 3 position of flavonoid or anthocyanidin with the use of UDP-glucose as a sugar donor. Patent Literature 2 describes that an antirrhinum-derived enzyme catalyzes a reaction of transferring a sugar to a hydroxy group at the 4' position of a chalcone with the use of UDP-glucose as a sugar donor. In addition, Patent Literature 1 describes that glycosyltransferase encoded by a gene incorporated therein catalyzes a reaction of transferring glucose with the use of UDP-glucose as a sugar donor (see Example 4 in Patent Literature 1).

CITATION LIST

Patent Literature

Patent Literature 1: JP Patent Publication (Kokai) No. 2003-289884 A
Patent Literature 2: WO2005/059141

Non-Patent Literature

Non-Patent Literature 1: J. Biol. Chem., Vol. 274, No. 11 (1999) pp. 7405-7411
Non-Patent Literature 2: J. Biol. Chem., Vol. 276, No. 6 (2001) pp. 4338-4343

SUMMARY OF INVENTION

As described above, there are many known glycosyl transfer reactions in which a sugar nucleotide is used as a sugar donor. However, there are few known glycosyl transfer reactions in which a compound other than a sugar nucleotide is used as a sugar donor. For instance, in order to examine the function of a glycosyltransferase in a study of plant pigments, it is necessary to use sugar nucleotides as sugar donors. However, sugar nucleotides are chemically unstable and thus difficult to isolate. Therefore, sugar nucleotides are relatively expensive reagents and difficult to get in some cases. For such reasons, a compound other than a sugar nucleotide, which can function as a sugar donor, is needed.

The present inventors found a compound that functions as a sugar donor in carnations over the course of research into carnation petal pigments. It was previously unknown whether or not this compound would function as a sugar donor.

Carnation petals contain a variety of pigments. A major example of pigments is anthocyanin formed via glycosylation of the 3 or 5 position of anthocyanidin (and particularly pelargonidin or cyanidin). However, the present inventors focused on the fact that there are carnations not having an anthocyanin in which 5 position of anthocyanidin is glycosylated depending on carnation variety. The present inventors predicted that carnations have a glycosyltransferase that transfers a sugar to the 5 position of anthocyanidin. Further, the present inventors presumed that a sugar donor used by the glycosyltransferase accumulates in carnations not having an anthocyanin in which 5 position of anthocyanidin is glycosylated. Therefore, the present inventors studied on an extract of carnation petals not having anthocyanin glycosylated at the 5 position and thus found a compound that functions as a sugar donor in the extract. Further, the present inventors discovered a novel glycosyltransferase that catalyzes a glycosyl transfer reaction using such novel sugar donor in an extract of carnation petals and in an extract of delphinium petals, thereby identifying a glycosyltransferase gene consisting of DNA encoding the glycosyltransferase.

According to the present invention, a novel glycosyltransferase, a glycosyltransferase gene consisting of DNA encoding the glycosyltransferase, and the use thereof are provided based on the above findings. Further, a sugar donating reagent containing a novel sugar donor compound and a novel method for glycosylation of polyphenol and a polyphenol glycosylation kit using the sugar donating reagent are provided.

The present invention is summarized as follows.
(1) A protein, which is the following (a) or (b):
  (a) a protein comprising the amino acid sequence set forth in SEQ ID NO: 1 or 3;
  (b) a protein comprising an amino acid sequence derived from the amino acid sequence shown in SEQ ID NO: 1 or 3 by deletion, substitution, insertion, or addition of one or more amino acids and having glycosyltransferase activity.
(2) A glycosyltransferase gene comprising DNA which encodes the protein according to (1).
(3) A glycosyltransferase gene comprising DNA which is one of the following (c) to (e):
  (c) DNA comprising the nucleotide sequence shown in SEQ ID NO: 2 or 4;
  (d) DNA which hybridizes under stringent conditions to DNA comprising a nucleotide sequence complementary to the nucleotide sequence set forth in SEQ ID NO: 2 or 4 and encodes a protein having glycosyltransferase activity; or
  (e) DNA comprising a degenerate isomer of the nucleotide sequence set forth in SEQ ID NO: 2 or 4.
(4) A recombinant vector comprising the glycosyltransferase gene according to (2) or (3).
(5) A transformant obtained by transforming a host cell using the recombinant vector according to (4).

(6) A plant transfected with the glycosyltransferase gene according to (2) or (3) or a progeny of the plant having the same properties as the plant.
(7) A method for producing the glycosyltransferase according to (1), which comprises culturing the transformant according to (5).
(8) A sugar donating reagent containing a compound of formula (A):

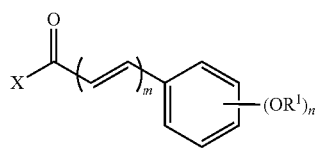

(A)

wherein $R^1$ and $R^2$ are independently selected from hydrogen, $C_{1-6}$ alkyl, $C_{2-6}$ alkenyl, and $C_{2-6}$ alkynyl wherein each of the groups is unsubstituted or substituted with one or more groups selected from OH, F, Cl, Br, I, CN, $NO_2$ and $SO_2$; n is 0, 1, 2, 3, 4 or, 5; m is 0 or 1, and X represents a monosaccharide bound via a 13 bond on its anomeric carbon.
(9) The sugar donating reagent according to (8), wherein $R^1$ is independently selected from hydrogen or $C_{1-6}$ alkyl which is unsubstituted or substituted with one or more groups selected from OH, F, Cl, Br, and I.
(10) The sugar donating reagent according to (9), wherein X is selected from the group consisting of glucose, glucuronic acid, galactose, xylose, apiose, allose, rhamnose, arabinofuranose, and mannose.
(11) The sugar donating reagent according to (10), wherein the compound of formula (I) or (II) is 1-O-β-vanillyl glucose, 1-O-β-isovanillyl glucose, 1-O-β-p-hydroxybenzoyl glucose, 1-O-β-p-coumaryl glucose, 1-O-β-caffeyl glucose, 1-O-β-feruloyl glucose, or 1-O-β-sinapoyl glucose.
(12) A method for glycosylation of polyphenol, which comprises reacting a polyphenol with the sugar donating reagent according to any one of (8) to (11) and a glycosyltransferase.
(13) The method for glycosylation according to (12), wherein the polyphenol is a flavonoid.
(14) The method for glycosylation according to (12) or (13), wherein the glycosyltransferase is derived from a carnation having non-red petals or derived from delphinium.
(15) The method for glycosylation according to (12) or (13), wherein the glycosyltransferase is the protein according to (1).
(16) A polyphenol glycosylation kit, which includes the sugar donating reagent according to any one of (8) to (11) and the glycosyltransferase according to (1).

The use of the sugar donating reagent of the present invention enables sugar donor reaction without a sugar nucleotide such as UDP-glucose. In addition, an enzyme capable of catalyzing a glycosyl transfer reaction using a sugar donor other than a sugar nucleotide can be provided using the glycosyltransferase and the glycosyltransferase gene of the present invention.

This description includes part or all of the contents as disclosed in the descriptions, claims, and/or drawings of Japanese Patent Applications Nos. 2009-011253 and 2009-184030, which are priority documents of the present application.

BRIEF DESCRIPTION OF DRAWINGS

The patent or application file contains at least one drawing executed in color. Copies of this patent or patent application publication with color drawing(s) will be provided by the Office upon request and payment of the necessary fee.

Figure 3:
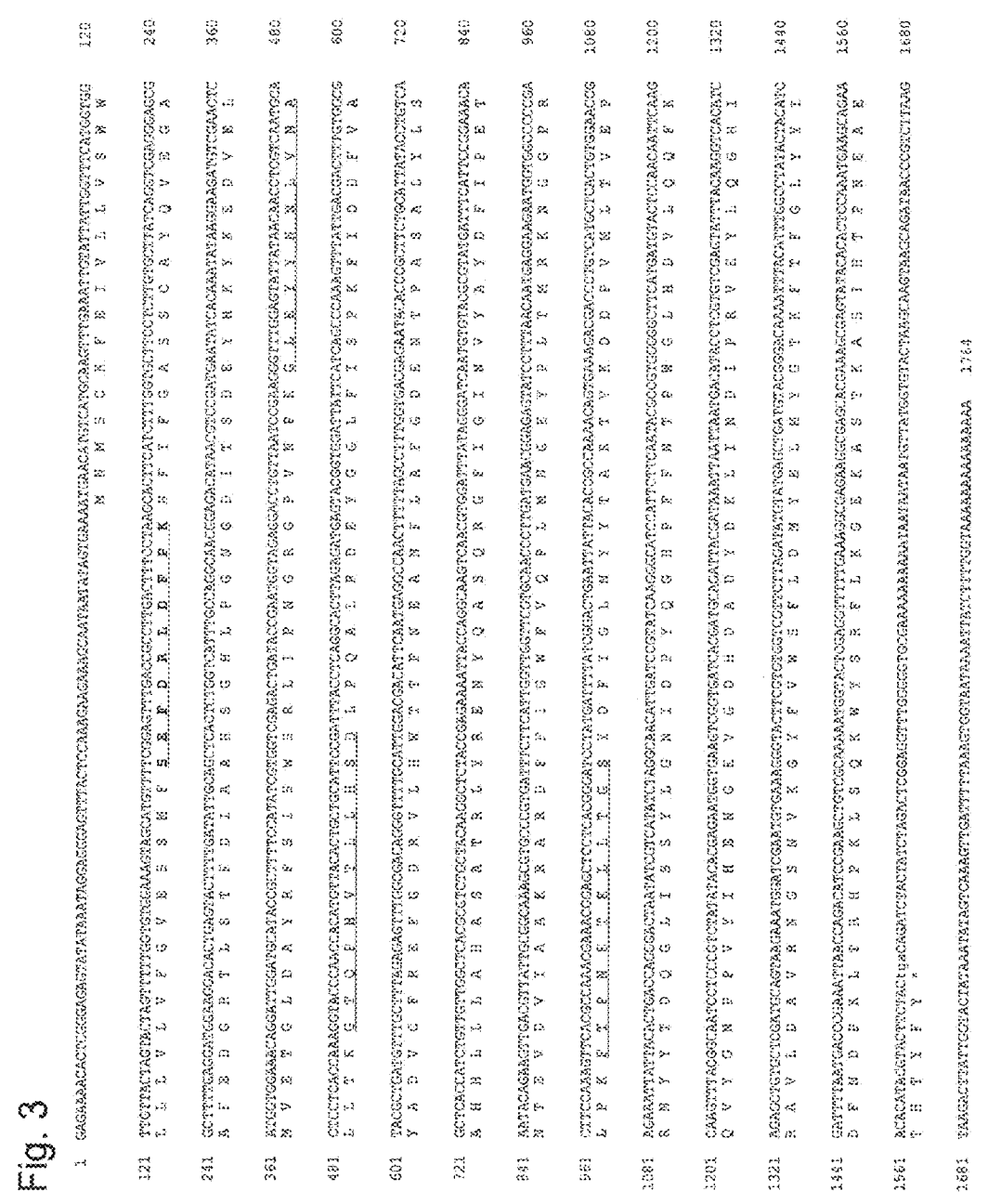

FIG. 3 shows the nucleotide sequence (SEQ ID NO: 2) predicted as the cDNA sequence of a carnation-derived glycosyltransferase and the predicted amino acid sequence (SEQ ID NO: 1) encoded by the nucleotide sequence.

FIG. 5 shows the nucleotide sequence (SEQ ID NO: 4) predicted as the cDNA sequence of a delphinium-derived glycosyltransferase and the predicted amino acid sequence (SEQ ID NO: 3) encoded by the nucleotide sequence.

DESCRIPTION OF EMBODIMENTS

[1] Sugar Donor Compound

Figure 1:
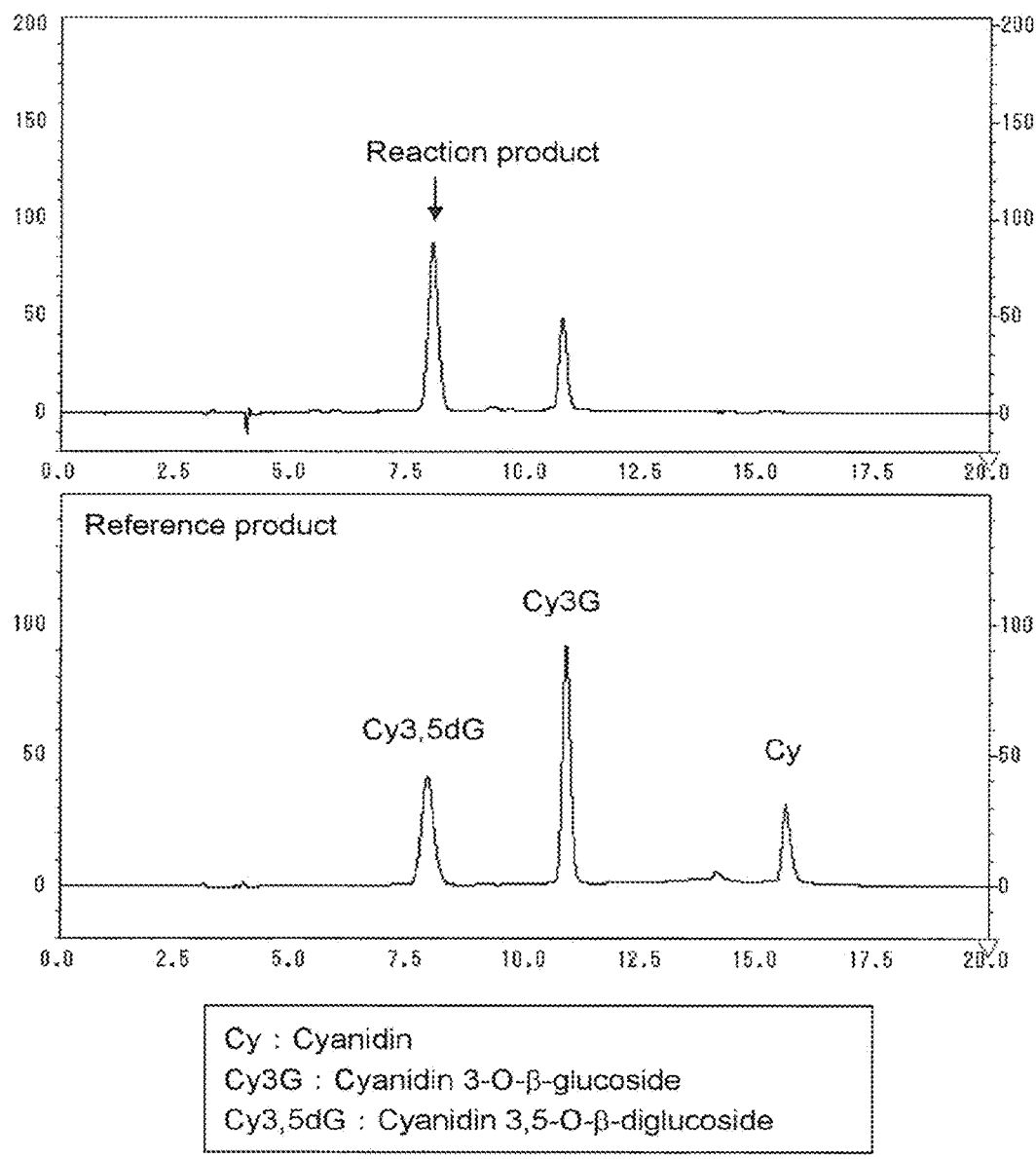
FIG. 1 shows HPLC analysis results indicating generation of cyanidin 3,5-O-β-diglucoside from cyanidin 3-O-β-glucoside as a result of glycosyl transfer reaction with the use of 1-O-β-vanillyl glucose as a sugar donor.

The novel sugar donor compound of the present invention has a structure represented by the following formula (A):

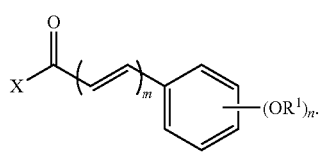

(A)

In formula (A), $R^1$ is selected from hydrogen, $C_{1-6}$ alkyl (e.g., methyl, ethyl, n-propyl, isopropyl, n-butyl, isobutyl, t-butyl, pentyl, or hexyl (and the same applies hereinafter to $C_{1-6}$ alkyl)), $C_{2-6}$ alkenyl (e.g., vinyl, 1-propenyl, 2-propenyl, 1-butenyl, 2-butenyl, 3-butenyl, 1-methyl-2-propenyl, 1-pentenyl, 2-pentenyl, 3-pentenyl, 4-pentenyl, 1-methyl-2-butenyl, 2-methyl-3-butenyl, 1-hexenyl, 2-hexenyl, 3-hexenyl, 4-hexenyl, 5-hexenyl, 1,1-dimethyl-2-butenyl, or 2-methyl-3-pentenyl (and the same applies hereinafter to $C_{2-6}$ alkenyl)), and $C_{2-6}$ alkynyl (e.g., ethinyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-hexynyl, 2-hexynyl, 3-hexynyl, 4-hexynyl, 5-hexynyl, 1,1-dimethyl-2-butynyl, or 2-methyl-3-pentynyl (and the same applies hereinafter to $C_{2-6}$ alkynyl)). Here, $C_{1-6}$ alkyl, $C_{2-6}$ alkenyl, or $C_{2-6}$ alkynyl may or may not be substituted with at least one member selected from the group consisting of OH, F, Cl, Br, I, CN, $NO_2$, $SO_2$, $C_{1-6}$ alkyl, $C_{2-6}$ alkenyl, and $C_{2-6}$ alkynyl. Preferably, $R^1$ is selected from either hydrogen or $C_{1-6}$ alkyl (provided that $C_{1-6}$ alkyl may or may not be substituted with at least one member selected from the group consisting of OH, F, Cl, Br, and I). More preferably, $R^1$ is selected from among hydrogen, methyl, ethyl, n-propyl, and isopropyl (each of which may or may not be substituted with at least one member selected from the group consisting of OH, F, Cl, Br, and I). Particularly preferably, $R^1$ is selected from either hydrogen or methyl. In formula (A), n is 0, 1, 2, 3, 4, or 5, preferably 0, 1, 2, 3, or 4, and particularly preferably 1, 2, or 3. In formula (A), m is 0 or 1.

If m is 0 in formula (A), the novel sugar donor compound of the present invention preferably has a structure represented by the following formula (I) or (II):

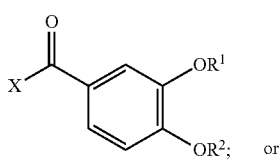

(I)

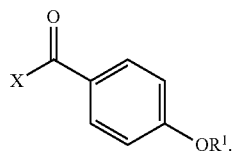

(II)

In formulae (I) and (II), $R^1$ and $R^2$ are independently selected from among hydrogen, $C_{1-6}$ alkyl, $C_{2-6}$ alkenyl, and $C_{2-6}$ alkynyl. Here, each of $C_{1-6}$ alkyl, $C_{2-6}$ alkenyl, and $C_{2-6}$ alkynyl may or may not be substituted with at least one member selected from the group consisting of OH, F, Cl, Br, I, CN, $NO_2$, $SO_2$, $C_{1-6}$ alkyl, $C_{2-6}$ alkenyl, and $C_{2-6}$ alkynyl. Preferably, $R^1$ and $R^2$ are independently selected from hydrogen and $C_{1-6}$ alkyl (provided that $C_{1-6}$ alkyl may or may not be substituted with at least one member selected from the group consisting of OH, F, Cl, Br, and I). More preferably, $R^1$ and $R^2$ are selected from among hydrogen, methyl, ethyl, n-propyl, and isopropyl (each of which may or may not be substituted with at least one member selected from the group consisting of OH, F, Cl, Br, and I). Particularly preferably, each of $R^1$ and $R^2$ is selected from either hydrogen or methyl. It is most preferable that $R^1$ be methyl and $R^2$ be hydrogen or that $R^1$ be hydrogen and $R^2$ be methyl in formula (I). In formula (II), $R^1$ is most preferably hydrogen.

If m is 1 in formula (A), the novel sugar donor compound of the present invention preferably has a structure represented by the following formula (III), (IV), or (V):

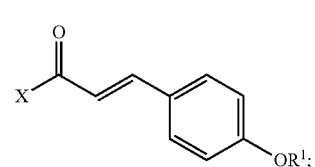

(III)

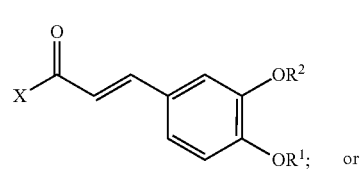

(IV)

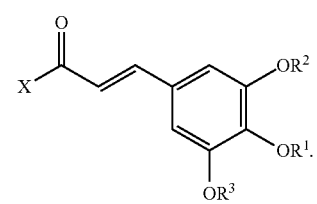

(V)

In formulae (III), (IV), and (V), $R^1$, $R^2$, and $R^3$ are independently selected from among hydrogen, $C_{1-6}$ alkyl, $C_{2-6}$ alkenyl, and $C_{2-6}$ alkynyl. Here, each of $C_{1-6}$ alkyl, $C_{2-6}$ alkenyl, and $C_{2-6}$ alkynyl may or may not be substituted with at least one member selected from the group consisting of OH, F, Cl, Br, I, CN, $NO_2$, $SO_2$, $C_{1-6}$ alkyl, $C_{2-6}$ alkenyl, and $C_{2-6}$ alkynyl. Preferably, each of $R^1$ and $R^2$ is independently selected from either hydrogen or $C_{1-6}$ alkyl (provided that $C_{1-6}$ alkyl may or may not be substituted with at least one member selected from the group consisting of OH, F, Cl, Br, and I). More preferably, any of $R^1$, $R^2$, and $R^3$ is selected from among hydrogen, methyl, ethyl, n-propyl, and isopropyl (each of which may or may not be substituted with at least one member selected from the group consisting of OH, F, Cl, Br, and I). Particularly preferably, each of $R^1$, $R^2$, and $R^3$ is selected from either hydrogen or methyl. In formula (III), it is most preferable that $R^1$ be hydrogen. In formula (IV), it is most preferable that $R^1$ be hydrogen and $R^2$ be methyl. In formula (V), it is most preferable that $R^1$ be hydrogen and each of $R^2$ and $R^3$ be methyl.

In addition, in formulae (A) and (I) to (V), X represents a monosaccharide bound via a β bond on its anomeric carbon. The expression "a sugar bound via a β bond on its anomeric carbon" used herein refers to a situation in which a non-sugar moiety (aglycone) is bonded via an ether bond to a hydroxy group on the anomeric carbon of sugar X in a manner such that the moiety is located at the β position of the sugar. Examples of a monosaccharide include: hexose such as allose, altrose, glucose, mannose, gulose, idose, galactose, or talose; pentose such as ribose, arabinose, xylose, or lyxose; tetrose such as erythrose or threose; and triose such as glyceraldehyde. In addition, sugars used herein include derivatives thereof. Examples of sugar derivatives include: reduced derivatives such as sugar alcohol, deoxy sugar, and glycal; oxidized derivatives such as aldonic acid, uronic acid, and aldaric acid; dehydrated derivatives such as glycoseen and anhydro sugar; phosphate-esterified products; acetate-esterified products; amino sugars; thio sugars; glycoproteins; sugar esters; and sugar ethers. Preferably, the monosaccharide is selected from among glucose, glucuronic acid, galactose, xylose, apiose, allose, rhamnose, arabinofuranose, and mannose. More preferably, the monosaccharide is selected from among glucose, glucuronic acid, galactose, xylose, apiose, and allose. Most preferably, the monosaccharide is glucose. Further, the monosaccharide may be in the D- or L-form but it is preferably in the D-form.

A particularly preferable example of a compound of formula (I) is 1-O-β-vanillyl glucose of the following formula:

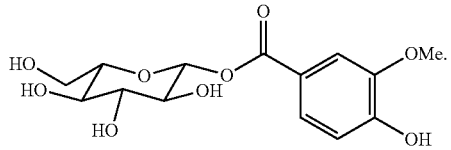

For instance, 1-O-β-vanillyl glucose can be prepared in the following manner. Carnation petals (with a red color and particularly preferably a color similar to bright red (0406) according to the Japan color standard for horticultural plants) are subjected to extraction using an organic solvent such as alcohol (e.g., methanol, ethanol, or propanol) or acetonitrile, an aqueous solution thereof, or a solution obtained by adding an organic acid (e.g., formic acid or trifluoroacetic acid) to such organic solvent or an aqueous solution thereof. Then, the extract is purified by HPLC using a reversed-phase column such as an ODS column. In addition to the above, 1-O-β-isovanillyl glucose represented by the following formula, which is an isomer of the above 1-O-β-vanillyl glucose, is a particularly preferable example of the compound of formula (I):

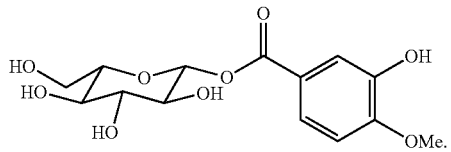 [SMILES: COc1ccc(C(=O)OC2OC(CO)C(O)C(O)C2O)cc1O]

A compound of formula (I) including 1-O-β-vanillyl glucose and 1-O-β-isovanillyl glucose can be extracted from a natural product, or alternatively, can be synthesized using a commercially available reagent by a conventionally known method. Further, it can be synthesized by transferring a sugar to a corresponding aromatic carboxylic acid using a known glycosyltransferase.

A particularly preferable example of the compound of formula (II) is 1-O-β-p-hydroxybenzoyl glucose represented by the following formula:

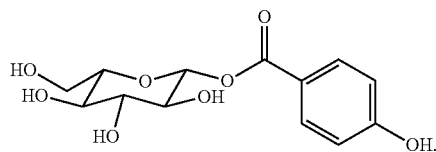 [SMILES: O=C(OC1OC(CO)C(O)C(O)C1O)c1ccc(O)cc1]

Also, the compound of formula (II) including 1-O-β-p-hydroxybenzoyl glucose can be extracted from a natural product, or alternatively, can be synthesized using a commercially available reagent by a conventionally known method. Further, it can be synthesized by transferring a sugar to a corresponding aromatic carboxylic acid using a known glycosyltransferase.

A particularly preferable example of the compound of formula (III) is 1-O-β-p-coumaryl glucose represented by the following formula:

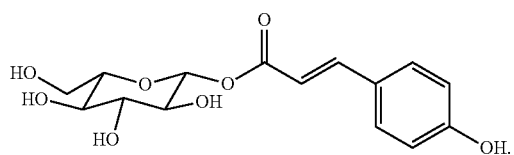 [SMILES: O=C(/C=C/c1ccc(O)cc1)OC1OC(CO)C(O)C(O)C1O]

A particularly preferable example of the compound of formula (IV) is 1-O-β-caffeyl glucose represented by the following formula:

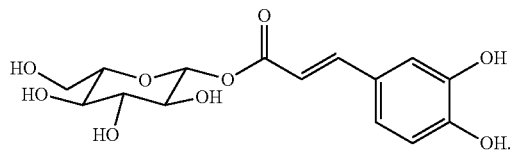 [SMILES: O=C(/C=C/c1ccc(O)c(O)c1)OC1OC(CO)C(O)C(O)C1O]

A particularly preferable example of the compound of formula (IV) is 1-O-β-feruloyl glucose represented by the following formula:

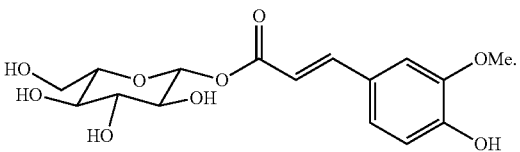 [SMILES: COc1cc(/C=C/C(=O)OC2OC(CO)C(O)C(O)C2O)ccc1O]

A particularly preferable example of the compound of formula (V) is 1-O-β-sinapoyl glucose represented by the following formula:

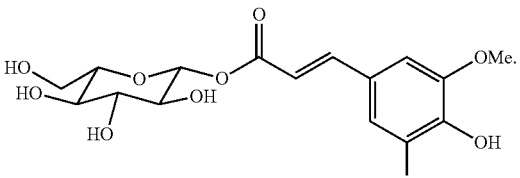

Also, any of the compounds of formulae (III) to (V) including 1-O-β-∈-coumaryl glucose, 1-O-β-caffeyl glucose, 1-O-β- feruloyl glucose, or 1-O-β-sinapoyl glucose, it can be extracted from a natural product, or alternatively, can be synthesized using a commercially available reagent by a conventionally known method. Also, it can be synthesized by, for example, the enzymological method described in Matsuba Y et al., Plant Biotechnology vol. 25, No. 4 (2008), pp. 369-375.

[2] Sugar Donor Reagent

The present invention relates to a sugar donating reagent containing the compound of formula (A). The term "sugar donating reagent" used herein refers to a reagent capable of glycosylating an arbitrary compound when used in combination with a glycosyltransferase.

Any compound may be glycosylated using the sugar donating reagent of the present invention. However, the sugar donating reagent of the present invention is particularly appropriate for polyphenol glycosylation. Examples of polyphenols include: flavonoid-based polyphenols; chlorogenic-acid-based polyphenols such as chlorogenic acid; phenylcarboxylic-acid-based polyphenols such as tannin; ellagic-acid-based polyphenols such as ellagic acid; lignan-based polyphenols such as sesamin; curcumin-based polyphenols such as curcumin; and coumarin-based polyphenols such as coumarin.

The sugar donating reagent of the present invention is appropriate for glycosylation of polyphenols, and, in particular, flavonoids. The term "flavonoid" collectively refers to a group of compounds each having 1,3-diphenylpropane as its basic skeleton. Flavonoids are known as major pigment compounds that cause expression of a variety of color tones in plants. Examples of flavonoids include chalcone, flavone, flavonol, flavan, flavanone, flavanol, flavanonol, isoflavone, and anthocyanidin.

The sugar donating reagent of the present invention is appropriate for glycosylation of flavonoids, and anthocyanidin and anthocyanidin derivatives in particular. Anthocyanidin is a compound that is glycosylated to form anthocyanin, which is a pigment widely found in plants. There are various types of anthocyanidin depending on differences in the position of a substitutent such as —OH or —OMe. Anthocyanidin that can be glycosylated by the sugar donating reagent of the present invention is not particularly limited. However, preferable examples of anthocyanidin include pelargonidin, cyanidin, delphinidin, aurantinidin, luteolinidin, peonidin, malvidin, petunidin, europinidin, rosinidin, and any compound selected from among derivatives of the above examples. Particularly preferable examples of anthocyanidin include cyanidin or pelargonidin and derivatives thereof. Cyanidin and pelargonidin are compounds structurally characterized by the formulae shown below:

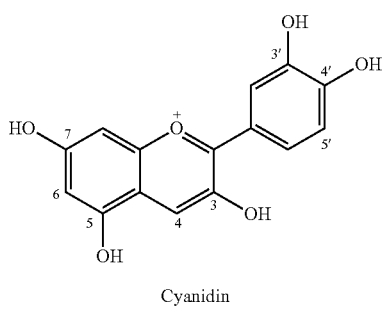

Cyanidin

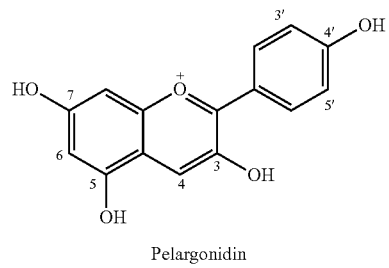

Pelargonidin

When anthocyanidin or a derivative thereof is glycosylated with the sugar donating reagent of the present invention, the position at which glycosylation takes place may be any position as long as a sugar can be bonded to anthocyanidin or a derivative thereof at such position. However, the sugar donating reagent of the present invention is excellent in glycosylating anthocyanidin or a derivative thereof at the 3, 5, or 7 position, and, in particular, cyanidin, pelargonidin, or a derivative of either thereof at the 5 or 7 position (preferably with glucose).

The term "anthocyanidin derivative" used herein refers to an anthocyanidin having at least one hydroxy group to which a monosaccharide, oligosaccharide, or polysaccharide has been bonded via an ether bond or an anthocyanidin having at least one hydrogen atom or hydroxy group substituted with a substituent such as halo, hydroxy, alkyl, alkenyl, alkynyl, alkoxy, aryl, cycloalkyl, carbonyl, ester, ether, amide, amino, cyano, nitro, sulfonyl, or sulfinyl

[3] A Method for Glycosylation and a Glycosylation Kit

In another aspect, the present invention relates to a method for glycosylation of polyphenol, which comprises allowing a polyphenol to react with a sugar donating reagent containing the compound of formula (A) and a glycosyltransferase. Examples of polyphenols include flavonoid-based polyphenols, chlorogenic-acid-based polyphenols such as chlorogenic acid, phenylcarboxylic-acid-based polyphenols such as tannin, ellagic-acid-based polyphenols such as ellagic acid, lignan-based polyphenols such as sesamin, curcumin-based polyphenols such as curcumin, and coumarin-based polyphenols such as coumarin.

The method for glycosylation of the present invention is appropriate for glycosylation of polyphenols, and, in particular, flavonoids. Examples of flavonoids include chalcone, flavone, flavonol, flavan, flavanone, flavanol, flavanonol, isoflavone, and anthocyanidin.

The method for glycosylation of the present invention is appropriate for glycosylation of flavonoids, and, in particular, anthocyanidin or an anthocyanidin derivative. An example of anthocyanidin that can be glycosylated by the method for glycosylation of the present invention is not particularly limited. However, preferable examples of anthocyanidin include pelargonidin, cyanidin, delphinidin, aurantinidin, luteolinidin, peonidin, malvidin, petunidin, europinidin, rosinidin, and any anthocyanidin selected from among derivatives of the above examples. Particularly preferable examples of anthocyanidins include cyanidin or pelargonidin and derivatives thereof.

When anthocyanidin or a derivative thereof is glycosylated by the method for glycosylation of the present invention, the position at which glycosylation takes place may be any position as long as a sugar can be bonded to anthocyanidin or a derivative thereof at such position. However, the method for glycosylation of the present invention is excellent in glycosylating anthocyanidin or a derivative thereof at the 3, 5, or 7 position, and, in particular, cyanidin, pelargonidin, or a derivative of either thereof at the 5 or 7 position (preferably with glucose).

A glycosyltransferase used in the method for glycosylation of the present invention is not particularly limited as long as it is an enzyme capable of catalyzing a glycosyl transfer reaction with the use of the compound of formula (A) as a sugar donor. However, a carnation-derived enzyme can be preferably used. Carnation (scientific name: *Dianthus caryophyllus*) is a plant belonging to the genus *Dianthus* of the family Caryophyllaceae of the order Caryophyllales, and it has been widely distributed as an ornamental plant. A glycosyltransferase extracted from carnation petals is particularly preferably used in the method for glycosylation of the present invention. A glycosyltransferase can be extracted by, for example, a method comprising dissolving a powder (obtained by grinding petals in liquid nitrogen) in potassium phosphate buffer and adding an ammonium sulfate solution thereto for protein precipitation. The thus extracted glycosyltransferase may be used after being purified via dialysis or HPLC according to need. For instance, purification can be carried out in the following manner: the extracted glycosyltransferase is adsorbed by an anion exchanger (e.g., Resouce Q (GE Healthcare) or DEAE sepharose (GE Healthcare)) at a pH of approximately 5.6 to 7.2, followed by elution with an NaCl aqueous solution according to a linear-concentration-gradient elution method. Alternatively, the extracted glycosyltransferase is adsorbed by a benzamidine-sepharose carrier (Benzamidine sepharose; GE Healthcare), which is a kind of affinity chromatography carrier, with the use of phosphoric acid buffer (pH 7.2), followed by elution with 4-amino benzamidine according to a linear-concentration-gradient elution method.

There are various types of carnations, and their petal colors differ depending on type. However, a glycosyltransferase used in the method for glycosylation of the present invention is preferably extracted from carnation petals with a color other than a red color (and, in particular, a red color similar to bright red (0406) according to the Japan color standard for horticultural plants) such as a white, yellow, pink, or purple color, and, in particular, a pink color (specifically, a color similar to vivid ruby (0107) according to the Japan color standard for horticultural plants) or a purple color (specifically, a color similar to vivid red purple (9207) according to the Japan color standard for horticultural plants). Any carnation variety can be used in the present invention as long as the petal color corresponds to any of the above colors. As described above, the carnation petal color is determined according to the Japan color standard for horticultural plants (published by the Japan Color Research Institute). Particularly preferably, glycosyltransferase used in the method for glycosylation of the present invention is extracted from carnation petals with a pink color (specifically, a color similar to vivid ruby (0107) according to the Japan color standard for horticultural plants). Examples of carnation varieties having such pink petals include "Beam Cherry," "Cinderella," and "Bell mouth." The most preferable example of a glycosyltransferase used in the method for glycosylation of the present invention is a glycosyltransferase having a molecular weight of approximately 55 kDa determined by SDS-PAGE (SDS-polyacrylamide gel electrophoresis) analysis and a reaction optimum pH of 5.0 to 5.5, which is selected from among glycosyltransferases extracted from carnation petals having a pink color as described above.

Also, a delphinium-derived enzyme can be preferably used as a glycosyltransferase used in the method for glycosylation of the present invention. *delphinium* (scientific name: *Delphinium grandiflorum* L.; Japanese name: Oohienso) is a plant belonging to the genus *Delphinium* of the family Ranunculaceae. It is particularly preferable to use an enzyme extracted from delphinium petals as a glycosyltransferase used in the method for glycosylation of the present invention. A glycosyltransferase can be extracted by the aforementioned method for extraction from carnation petals.

In another aspect, the present invention relates to a polyphenol glycosylation kit including the sugar donating reagent and the glycosyltransferase described above.

[4] Glycosyltransferase

The glycosyltransferase of the present invention is the above carnation- or delphinium-derived glycosyltransferase. An example of the glycosyltransferase of the present invention is a protein consisting of the amino acid sequence of SEQ ID NO: 1 or 3. The glycosyltransferase of the present invention includes a protein that is functionally equivalent to the protein consisting of the amino acid sequence of SEQ ID NO: 1 or 3. Therefore, the glycosyltransferase of the present invention includes a protein consisting of an amino acid sequence derived from the amino acid sequence set forth in SEQ ID NO: 1 or 3 by deletion, substitution, insertion, or addition of one or more amino acids and having glycosyltransferase activity.

Here, the term "several amino acids" refers to 2 to 5 and preferably 2 to 3 amino acids. Deletion, addition, insertion, or substitution of one or plurality of amino acids with respect to the amino acid sequence of the relevant sequence number can be carried out by modifying the sequence of DNA encoding a protein consisting of the amino acid sequence of each sequence number by a general technique such as site-specific mutagenesis (see, for example, Zoller et al., Nucleic Acids Res. 10 6478-6500, 1982). Here, substitution of amino acid residues is preferably preservative substitution. It is known that preservative substitution can take place between the following amino acid residues: glycine (Gly) and proline (Pro), glycine and alanine (Ala) or valine (Val), leucine (Leu) and isoleucine (Ile), glutamic acid (Glu) and glutamine (Gln), aspartic acid (Asp) and asparagine (Asn), cysteine (Cys) and threonine (Thr), threonine and serine (Ser) or alanine, and lysine (Lys) and arginine (Arg).

Also, the glycosyltransferase of the present invention includes a protein having glycosyltransferase activity and consisting of an amino acid sequence having 80% or more identity, preferably 90% or more identity, more preferably 95% or more identity, and further preferably 98% or more identity to the amino acid sequence of SEQ ID NO: 1 or 3.

A compound used as a sugar donor by the glycosyltransferase of the present invention is preferably the above sugar donor compound that has the structure of formula (A). Among examples of the compound of formula (A), it is particularly preferable to use, as sugar donor compounds, compounds of formulae (I) to (V). In addition, it is especially preferable to use, as sugar donor compounds, 1-O-β-vanillyl glucose, 1-O-β-isovanillyl glucose, 1-O-β-p-hydroxybenzoyl glucose, 1-O-β-p-coumaryl glucose, 1-O-β-caffeyl glucose, 1-O-β-feruloyl glucose, and 1-O-β-sinapoyl glucose. Regarding the compound of formula (A), details are described above.

The glycosyltransferase of the present invention is appropriate for glycosylation of polyphenols. The glycosyltransferase of the present invention is appropriate for glycosylation of polyphenols, preferably flavonoid, and particularly preferably anthocyanidin or an anthocyanidin derivative. Specifically, the glycosyltransferase of the present invention is appropriate for glycosylation of cyanidin or pelargonidin and derivatives thereof. More specifically, the glycosyltransferase of the present invention is appropriate for glycosylation (preferably with glucose) at the 3, 5, or 7 position of anthocyanidin or a derivative thereof, and, in particular, the 5 or 7 position of cyanidin, pelargonidin, or a derivative of either thereof. Details of such polyphenols are described above.

[5] Glycosyltransferase Gene

The glycosyltransferase gene of the present invention is a gene encoding a protein having activity of causing sugar transfer from the above glycosyltransferase (i.e., a sugar donor) to an arbitrary compound (i.e., glycosylation of the arbitrary compound). Specifically, the glycosyltransferase gene of the present invention is a glycosyltransferase gene consisting of DNA encoding the above glycosyltransferase. Specific examples of the glycosyltransferase gene of the present invention include a gene consisting of DNA having the nucleotide sequence of SEQ ID NO: 2 or 4.

The glycosyltransferase gene of the present invention includes a gene that is functionally equivalent to a gene consisting of DNA having the nucleotide sequence of SEQ ID NO: 2 or 4. Here, the expression "a gene that is functionally equivalent" refers to a case in which a protein encoded by a gene of interest has biological and biochemical functions equivalent to those of the protein encoded by the glycosyltransferase gene of the present invention. An example of a method for preparing a gene functionally equivalent to a specific gene known to persons skilled in the art is a method using a hybridization technique (see, for example, Sambrook, J et al., Molecular Cloning 2nd ed., 9.47-9.58, Cold Spring Harbor Lab. press (1989)). Therefore, the glycosyltransferase gene of the present invention includes a gene consisting of DNA encoding a protein that hybridizes under stringent conditions to DNA consisting of a nucleotide sequence complementary to the nucleotide sequence of SEQ ID NO: 2 or 4 and has glycosyltransferase activity.

Here, the term "stringent conditions" refers to conditions under which namely a specific hybrid is formed, but a nonspecific hybrid is not formed. Such conditions include low stringent conditions and high stringent conditions. However, high-stringency conditions are preferable. Low-stringency conditions comprises, for example, washing at 42° C., 5×SSC, and 0.1% SDS and preferably washing at 50° C., 5×SSC, and 0.1% SDS after hybridization. High-stringency conditions comprises, for example, washing at 65° C., 0.1× SSC, and 0.1% SDS after hybridization. DNA consisting of a nucleotide sequence highly homologous (i.e., having 80% or more, preferably 90% or more, more preferably 95% or more, and further preferably 98% or more homology or having 80% or more, preferably 90% or more, more preferably 95% or more, and further preferably 98% or more identity) to the nucleotide sequence of SEQ ID NO: 2 or 4 can hybridize to DNA consisting of the nucleotide sequence complementary to the nucleotide sequence of the DNA under the above stringent conditions.

Also, the glycosyltransferase gene of the present invention includes a degenerate isomer of a gene consisting of DNA having the nucleotide sequence of SEQ ID NO: 2 or 4. Here, the term "degenerate isomer" refers to DNA which is different only in a degenerate codon and capable of encoding a protein identical to a protein encoded by the above gene. For example, a degenerate isomer of DNA comprising the nucleotide sequence of SEQ ID NO: 2 or 4 has a degenerate codon corresponding to an amino acid of the sequence. More specifically, it can be said that a codon (AAC) corresponding to Asn has been replaced by a degenerate codon (e.g., AAT) thereof in a degenerate isomer.

[6] A Recombinant Vector Containing a Glycosyltransferase Gene

Further, the present invention relates to a recombinant vector containing the above glycosyltransferase gene. The recombinant vector of the present invention can be constructed by introducing the above glycosyltransferase gene into an appropriate vector. The type of vector is not particularly limited. Examples of a vector that can be used include: pBI, pPZP, pSMA, pUC, pBR, pBluescript, pET, pGEM, pKS1, and pTriEXTM vectors (TAKARA); and a pTrcHis2-TOPO vector (Invitrogen). Also, viral vectors such as cauliflower mosaic virus (CaMV), bean golden mosaic virus (BGMV), and tobacco mosaic virus (TMV) can be used. Alternatively, a pBI binary vector may be used.

In order to insert a gene into a vector, for example, a method comprising cleaving isolated DNA to be inserted using an appropriate restriction enzyme and then inserting the DNA fragment at a restriction enzyme site or multicloning site of an appropriate vector DNA for ligation to vector DNA can be used.

It is necessary to incorporate the above gene into a vector in a manner that allows the gene to function therein. For such purpose, a vector is allowed to contain components such as a promoter, an intron, an enhancer, a translation stop codon, a terminator, a polyA addition signal, and a 5'-UTR sequence inside, upstream, or downstream of the gene. In addition, a vector may contain a selection marker gene. Conventionally known vector components can be used in combination in an adequate manner.

Examples of a promoter capable of functioning in plant cells include a cauliflower mosaic virus (CaMV) 35S promoter, a nopaline synthase gene promoter (Pnos), a maize (*Zea mays*)-derived ubiquitin promoter, a rice-derived actin promoter, a tobacco-derived PR protein promoter, a petunia-derived EPSP synthase promoter, and a chsA promoter. Among them, a cauliflower mosaic virus (CaMV) 35S promoter is known as a systemically expressed promoter. In addition, an EPSP synthase promoter or a chsA promoter from petunia is known to function in petals.

Examples of a promoter capable of functioning in bacterial cells include: promoters of the *Bacillus stearothermophilus* maltogenic amylase gene, the *Bacillus licheniformis* amylase gene, the *Bacillus amyloliquefaciens* BAN amylase gene, the *Bacillus subtilis* alkali protease gene, and the *Bacillus pumilus* xylosidase gene; a phage lambda PR or PL promoter, and an *Escherichia coli* lac, trp, or tac promoter.

Examples of a promoter capable of functioning in yeast host cells include a yeast glycolytic system gene-derived promoter, an alcohol dehydrogenase gene promoter, a TPI1 promoter, and an ADH2-4c promoter. Examples of a promoter capable of functioning in fungi include an ADH3 promoter and a tpiA promoter. Examples of a promoter capable of functioning in insect cells include a polyhedrin promoter, a P10 promoter, an *Autographa californica* nuclear polyhedrosis protein promoter, a Baculovirus immediate-early gene 1 promoter, and a Baculovirus 39K delayed-early gene promoter. Examples of a promoter capable of functioning in mammals include an SV40 promoter, an MT-1 promoter, a CMV promoter, and an Adenovirus-2 major late promoter.

In addition, it is possible to use a promoter obtained using an *Agrobacterium* isopentenyl transferase (ipt) gene or a nopaline synthase (nos) gene promoter, a promoter of a highly expressed gene obtained from the genome of a plant used as a transformation host, or the like (Genschik et al., Gene, 148, 195-202 (1994)). Further, it is also possible to use a chimeric promoter comprising a combination of a plurality of the above promoters and having significantly increased promoter activity (Plant J., 7, 661-676 (1995)).

Examples of an enhancer that can be used include a virus-derived translation enhancer and a plant-derived translation enhancer. Examples of a virus-derived translation enhancer include sequences of tobacco mosaic virus, alfalfa mosaic virus RNA4, bromo mosaic virus RNA3, potato virus X, and tobacco H virus (Gallie et al., Nuc. Acids Res., 15, 8693-8711 (1987)). In addition, examples of a plant-derived translation enhancer include a soybean β-1,3 glucanase (Glu)-derived sequence (written by Isao Ishida and Norihiko Misawa, edited by Kodansha Scientific, "Manuals for Cell Engineering Experimental Operations (*Saibo-Kogaku Jikken Sousa Nyumon*)," Kodansha Ltd., p. 119 (1992)) and a sequence from a tobacco ferredoxin-binding subunit (PsaDb) (Yamamoto et al., J. Biol. Chem., 270, 12466-12470 (1995)). Further, examples of an enhancer include an enhancer region containing the upstream sequence of a CaMV 35S promoter, an SV40 enhancer, and a CMV enhancer. Examples of a translation stop codon include a sequence such as TAA, TAG, or TGA.

Examples of a terminator include a nopaline synthase (NOS) gene terminator, an octopine synthase (OCS) gene terminator, a CaMV 35S terminator, an *Escherichia coli* lipopolyprotein 1 pp 3' terminator, a trp operon terminator, an amyB terminator, and an ADH1 gene terminator.

Examples of a selection marker gene include drug-resistant genes (e.g., the tetracycline-resistant gene, the ampicillin-resistant gene, the kanamycin-resistant gene, the hygromycin-resistant gene, the spectinomycin-resistant gene, the chloramphenicol-resistant gene, and the neomycin-resistant gene), fluorescent or luminescent reporter genes (e.g., luciferase, β-galactosidase, β-glucuronidase (GUS), and green fluorescence protein (GFP)), and genes of enzymes such as neomycin phosphotransferase II (NPT II) and dihydrofolate reductase.

[7] Transformant

The present invention further relates to a transformant that can be produced by introducing a recombinant vector containing the above glycosyltransferase gene into an adequate host.

Such host is not limited as long as the introduced gene can be expressed therein. Examples of the host include bacteria such as *Escherichia coli* and *Bacillus subtilis*, yeasts such as *Saccharomyces cerevisiae, Schizosaccharomyces pombe,* and *Pichia pastoris,* and fungi such as *Aspergillus, Neurospora, Fusarium,* and *Trichoderma*. In addition, plant cells of monocotyledons or dicotyledons belonging to the families Brassicaceae, Lauraceae, Annonaceae, Solanaceae, Rosaceae, and the like, insect cells such as sf9 and sf21, and mammal cells such as HEK293 cells, HeLa cells, and Chinese hamster ovarian cells may be used as hosts.

For introduction of a gene or a recombinant vector, conventionally known methods such as an *Agrobacterium* method, a PEG-calcium phosphate method, an electroporation method, a liposome method, a particle gun method, and a microinjection method can be used. The introduced gene may be incorporated into the genomic DNA of a host or it may exist in a foreign vector in a host.

[8] A Plant Transfected with a Glycosyltransferase Gene

Moreover, the present invention relates to a plant transfected with a glycosyltransferase gene, which is obtained via transformation using a recombinant vector containing the above glycosyltransferase gene, or a progeny of the plant having properties of the plant.

For preparation of a transformed plant, a variety of reported and established methods can be adequately used. Preferable examples of such method include a biological method such as a method using, as a vector, a virus, a Ti plasmid or an Ri plasmid of *Agrobacterium* or the like and a physical method such as a method for gene introduction using electroporation, polyethyleneglycol, a particle gun, or microinjection (Plant Genetic Transformation and Gene Expression; a laboratory manual, edited by J. Draper et al., Blackwell Scientific Publication (1988)), or silicon whiskers (Euphytica, 85, 75-80 (1995); In Vitro Cell. Dev. Biol., 31, 101-104 (1995); Plant Science, 132, 31-43 (1998)). Persons skilled in the art can adequately select and use such gene introduction method.

Examples of plants subjected to transformation with the use of a gene encoding the novel glycosyltransferase of the present invention include monocotyledon plants such as lily, orchid, and araceous foliage plants and dicotyledon plants such as potato, chrysanthemum, rose, carnation, petunia, gypsophila, cyclamen, aster, salvia, and gentian. Types of particularly preferable plants are chrysanthemum, carnation, rose, petunia, and the like. Among the above, examples of plants subjected to transformation with the use of the glycosyltransferase of the present invention include plants that do not have activity of the glycosyltransferase of the present invention; that is to say, plants lacking the glycosyltransferase of the present invention and plants in which the glycosyltransferase of the present invention does not function.

For production of transformed plants according to the present invention, plant materials are transformed with the gene of the present invention. Examples of plant materials include cells of growing points, shoot primordia, meristems, leaf discs, stem discs, root discs, tuber discs, petiole discs, protoplasts, calluses, anthers, pollens, pollen tubes, peduncle discs, scape discs, petals, calyx discs, and the like.

When plant cells are used as plant materials, regeneration of a transformed plant from the obtained transformed cells can be carried out by a known tissue culture method. Persons skilled in the art can readily carry out such procedure by a generally known method for regenerating a plant from plant cells. Regarding a method for regenerating a plant from plant cells, literature such as the "Plant Cell Culture Manual" (written and edited by Yasuyuki Yamada, Kodansha Scientific Ltd., 1984) can be referred to.

Specifically, transformed plant cells are cultured in advance in a sterilized medium for callus formation to which inorganic nutrients, vitamins, carbon source, sugars used as energy sources, and plant growth regulators (plant hormones such as auxin and cytokinin) have been added for formation of dedifferentiated calluses that can adventitiously proliferate (hereinafter referred to as "callus induction"). The thus formed calluses are transferred to a fresh medium containing plant growth regulators such as auxin for further proliferation (subculture).

Callus induction is performed using a solid medium such as agar. Subculture is performed via, for example, liquid culture. Thus, each culture can be efficiently carried out for mass proliferation. Next, calluses that have proliferated as a result of the above subculture are cultured under appropriate conditions for induction of redifferentiation of organs (hereinafter referred to as "redifferentiation induction"). Eventually, a complete plant can be regenerated. Redifferentiation induction can be carried out by adequately predetermining types and amounts of different components in a medium, such as a plant growth regulator (e.g., auxin or cytokinin) and a carbon source, light intensity, temperature, and the like. As a result of redifferentiation induction, adventitious embryos, adventitious roots, adventitious buds, adventitious leaves/stems, and the like are formed. Such redifferentiated organs are cultured, thereby allowing growth of a complete plant.

Alternatively, an incomplete plant (in the form of encapsulated artificial seeds, dried embryos, lyophilized cells and tissues, or the like) is preserved or treated. A complete plant can be regenerated from such incomplete plant via culture or the like according to need. Further, it is also possible to regenerate a transformed plant without callus formation by culturing or cultivating transformed plant cells under the above adequately predetermined conditions comprising different types and amounts of components, light intensity, temperature, and the like.

Once a transformed plant with a genome that has been transfected with the glycosyltransferase gene of the present invention can be obtained, a progeny can be obtained from the plant via sexual or asexual reproduction. In addition, it is also possible to mass-produce the plant using reproduction materials (e.g., seeds, fruits, cut ears, tubers, root tubers, stocks, calluses, and protoplasts) obtained from the plant or a progeny or clone thereof. Further, it is also possible to produce cut flowers from the transformed plant of the present invention or a progeny or clone thereof. The present invention also can provide such cut flowers. The term "cut flowers" generally refers to flowers that have been cut without removing branches or stems therefrom. However, the term "cut flowers" used in the present invention also refers to flowers lacking branches or stems.

[9] Production of Glycosyltransferase

Further, the present invention relates to a method for producing glycosyltransferase. The glycosyltransferase of the present invention can be produced via culture in an appropriate medium under conditions that allow expression of an introduced gene according to type of host.

Examples of a medium include an LB medium, an M9 medium, a YPD medium, a YPG medium, a YPM medium, a YPDM medium, and an SMM medium. Such medium contains a carbon source (e.g., glucose, glycerin, mannitol, fructose, or lactose), a nitrogen source such as an inorganic nitrogen source (e.g., ammonium sulfate or ammonium chloride) or an organic nitrogen source (e.g., casein digest, yeast extract, polypeptone, bacto tryptone, or beef extract), an inorganic salt (e.g., sodium diphosphate, potassium diphosphate, magnesium chloride, magnesium sulfate, or calcium chloride), a vitamin (e.g., vitamin B1), and a drug (e.g., an antibiotic such as ampicillin, tetracycline, or kanamycin) according to need. Culture conditions are not particularly limited as long as they are appropriate for gene expression. However, culture is carried out at generally 10° C. to 45° C. for several hours to several hundreds of hours with aeration and/or stirring according to need.

In order to obtain the enzyme of the present invention from a culture product (including a culture supernatant or a cultured transformant), a protein accumulating in a culture product can be extracted by a known method and then purified according to need. Examples of such method whereby the enzyme of the present invention can be obtained include a solvent extraction method, a salting-out method, a solvent precipitation method, a dialysis method, an ultrafiltration method, a gel electrophoresis method, gel filtration chromatography, ion-exchange chromatography, reversed-phase chromatography, and affinity chromatography. Such methods can be used alone or in combinations in an adequate manner.

As described above, the present invention relates to a sugar donating reagent containing a compound of formula (A), a method for glycosylation of polyphenol comprising allowing such sugar donating reagent to react with a glycosyltransferase, and a polyphenol glycosylation kit including the sugar donating reagent and the glycosyltransferase. According to the present invention, a glycosyl transfer reaction can be carried out without a sugar nucleotide that is a relatively expensive reagent such as UDP-glucose.

In addition, it is predicted that the glycosyl transfer reaction between the novel sugar donor compound and the glycosyltransferase of the present invention would differ from conventionally known glycosyl transfer reactions in terms of reaction mechanism. Therefore, it is expected that glycosylation of a substrate that has been conventionally difficult to glycosylate can be realized according to the present invention. In general, when a fat-soluble compound is glycosylated, the compound becomes soluble in water. In addition, when a water-soluble compound is glycosylated, stability of the compound can be improved. These facts have been known. For instance, the present invention can be used for the development of novel pharmaceutical compounds or novel functional food materials. In particular, a carnation-derived glycosyltransferase that catalyzes a glycosyl transfer reaction using, as a sugar donor, the novel sugar donor compound of the present invention has a relatively low optimum pH for reactions. Therefore, a glycosyl transfer reaction can be carried out even in acidic environments in which it has been difficult to carry out a glycosyl transfer reaction. Further, the method for glycosylation of the present invention can be used for glycosylation of other compounds, in addition to polyphenols. The method for glycosylation of the present invention would be applied to, for example, sugar chain synthesis.

Moreover, the present invention relates to a novel glycosyltransferase, a glycosyltransferase gene that encodes the glycosyltransferase, a recombinant vector containing the glycosyltransferase gene, a transformant obtained by transforming a host cell using the recombinant vector, and a plant transfected with the glycosyltransferase gene. When the novel glycosyltransferase of the present invention is used in combination with a sugar donating reagent containing the compound of formula (A) of the present invention, the aforementioned novel glycosyl transfer reaction can be efficiently carried out.

A novel glycosyltransferase can be artificially produced using the glycosyltransferase gene of the present invention. In addition, the use of the glycosyltransferase gene of the present invention enables production of a plant having a non-conventional petal color by, for example, introducing the gene into a plant lacking the glycosyltransferase of the present invention.

EXAMPLES

The present invention is hereafter described in greater detail with reference to the following examples, although the technical scope of the present invention is not limited thereto.

Example 1

(1) Preparation of Crude Enzyme Liquid of Glycosyltransferase

Pink petals from a carnation (variety: "Beam Cherry") were ground into a powder in liquid nitrogen using a mortar and a pestle. The powder was added in a stepwise manner to a 50 mM potassium phosphate buffer (pH 7.2) and dissolved therein via stirring to prevent freezing. Then, an insoluble fraction was removed by centrifugation. A saturate ammonium sulfate solution was added to the obtained supernatant so as to result in a concentration of 80% and left on ice for 5 minutes. A protein precipitated in the solution was collected by centrifugation. A 10 mM potassium phosphate buffer was added thereto until the precipitate was completely dissolved.

The obtained solution was applied to a Sephadex G-25 gel filtration support (GE Healthcare) for desalting. Thus, a crude enzyme liquid was obtained.

(2) Extraction of a Sugar Donor Compound

Red petals from a carnation (variety: "Red Vital") were immersed overnight in a 50% ethanol aqueous solution and filtered with filter paper. The obtained filtrate was concentrated under reduced pressure using a rotary evaporator. The concentrated filtrate was applied to a synthetic adsorption resin (DIAION® HP20, Mitsubishi Chemical Corporation) and the eluate fraction was collected. Further, the synthetic adsorption resin was washed with pure water at a volume 5 times that of the synthetic adsorption resin. The obtained washing liquid was added to the eluate fraction. The fraction was concentrated under reduced pressure. Acetic acid was added thereto so as to result in a final concentration of 0.1%. Then, the resultant was applied to an ODS column (Wakosil C18, Wako Pure Chemical Industries, Ltd.) that had been equilibrated in advance with a 0.1% acetic acid aqueous solution. The column was washed with a 0.1% acetic acid aqueous solution at a volume 5 times the column volume. The fraction eluted with a 0.1% acetic acid aqueous solution containing 5% methanol was collected and concentrated under reduced pressure. The resultant was used as a sample for fractionation HPLC.

Fractionation HPLC was performed using a Develosil RPAQUEOUS-AR-5 (particle size: 5 μm; inner diameter× length: 10 mm×250 mm; Nomura Chemical) reversed-phase column, eluent A (a 0.1% acetic acid aqueous solution), and eluent B (a 90% methanol aqueous solution). After separation with a linear gradient of 7% to 30% eluent B at a flow rate of 5 ml/min (40 minutes), the separated liquid was fractionated (5 ml for each fraction). The glycosyltransferase activity of each fraction was evaluated using the crude enzyme liquid (see the evaluation method described below). The fractions (the 21st to 24th fractions) that had been found to have the activity (active fractions) were collected, concentrated, and subjected to fractionation HPLC again.

The second fractionation HPLC was performed using an XTerra Prep MSC18 reversed-phase column (particle size: 10 μm; inner diameter×length: 10×250 mm; Waters), eluent A (a 0.1% acetic acid aqueous solution), and eluent B (a 90% methanol aqueous solution). After separation with a linear gradient of 6% to 10% eluent B at a flow rate of 5 ml/min (40 minutes), the separated liquid was fractionated (5 minutes for each fraction). The glycosyltransferase activity of each fraction was evaluated using the crude enzyme (see the evaluation method described below). The active fractions (the 21st to 25th fractions) were collected, concentrated, and subjected to fractionation HPLC again.

The third fractionation HPLC was performed using acetonitrile and pure water as eluents and an COSMOSIL HILIC Packed column (particle size: 5 μm; inner diameter×length: 10 mm×250 mm; Nacalai Tesque). After separation with a linear gradient of 100% to 75% acetonitrile at a flow rate of 5 ml/min (40 minutes), the separated liquid was fractionated (5 minutes for each fraction). The glycosyltransferase activity of each fraction was evaluated using the crude enzyme liquid (see the evaluation method described below). The active fractions (the 19th to 24th fractions) were collected and concentrated.

The red carnation petal extract purified above was applied to a high resolution HR-ESI-TOF mass spectrometer (AccuTOF JML-T100LC spectrometer, JEOL Ltd.). A molecular ion peak of m/z=353.08313 was detected via positive mode and a molecular ion peak of m/z=329.29592 was detected via negative mode. Thus, the extract was presumed to be a compound having a molecular weight of 330.

Next, the above purified extract was subjected to $^1$H NMR, $^{13}$C NMR HMQC, HMBC, and NOE analyses (ECX400; JEOL Ltd.). Table 1 shows the results. The results of the analyses indicated that the purified extract was a compound in which a hydroxy group at the 1 position (an anomeric carbon) of glucose was bound via an ester bond to a carboxyl group of vanillic acid. In addition, the coupling constant (J=7.8) at the anomeric position of 1H NMR indicated that the ester bond of glucose was a β bond. Therefore, the purified extract was found to be 1-O-β-vanillyl glucose.

TABLE 1

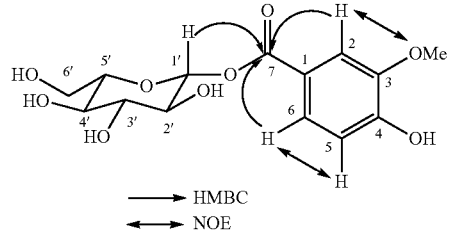 [SMILES: COc1cc(C(=O)OC2OC(CO)C(O)C(O)C2O)ccc1O]

→ HMBC
←→ NOE

NMR chemical shift (400 MHz CD$_3$OD)

| Position | δ $^1$H (ppm); multiple; J (Hz) | δ $^{13}$C (ppm) |
|---|---|---|
| Vanillic acid | | |
| 1 | — | 120.9 |
| 2 | 7.58, d, J = 1.8 | 113.8 |
| 3 | — | 149.1 |
| 4 | — | 154.7 |
| 5 | 6.82, d, J = 8.5 | 116.3 |
| 6 | 7.62, dd, J = 1.8, 8.5 | 125.9 |
| 7 | — | 166.9 |
| OMe | 3.88 | 56.4 |
| Glucose | | |
| 1' | 5.67, d, J = 7.8 | 96.0 |
| 2'~5' | 3.4~3.95 (4H) | 71.1, 74.1, 78.1, 78.8 |
| 6' | 3.69, dd, J = 4.6, 12.1 | 62.3 |
| | 3.85, dd, J = 1.8, 12.1 | |

NMR; ECX400 (JEOL, Tokyo, Japan)
TOF-MS; AccuTOF JML-T100LC spectrometer (JEOL, Tokyo, Japan)

(3) Evaluation of Glycosyltransferase Activity of the HPLC Fractions Using the Crude Enzyme Liquid HPLC fraction (3 μl), a 100 mM citric acid buffer (pH 5.6) (5 μl), and 2 mM cyanidin 3-glucoside (3 μl) were added to the crude enzyme liquid (30 μl). The reaction solution was left at 30° C. for 40 minutes. Thereafter, a 20% phosphoric acid aqueous solution (2.5 μl) was added thereto to terminate the reaction. Insoluble matter was removed by centrifugation, followed by HPLC analysis.

HPLC analysis was performed using a 1.5% phosphoric acid aqueous solution and acetonitrile as eluents and a Chromolith Performance RP-18e column (4.6×100 mm; Merck). After separation with a linear gradient of 17% to 40% acetonitrile at a flow rate of 3 ml/min (4 minutes), generation of cyanidin 3,5-diglucoside was confirmed by measuring the absorbance at a wavelength of 520 nm using a ultraviolet-visible detector.

(4) Detection of Glycosyl Transfer Reaction Using 1-O-β-vanillyl Glucose as a Sugar Donor Pink petals of a carnation (variety: "Beam Cherry") were ground into a powder in liquid nitrogen using a mortar and a pestle. The obtained powder was added in a stepwise manner to a 50 mM potassium phosphate buffer (pH 7.2) and dissolved therein via stirring to prevent freezing. Then, an insoluble fraction was removed by centrifugation. A saturate ammonium sulfate solution was added to the obtained supernatant so as to result in a concentration of 80%. The mixture was left on ice for 5 minutes. The precipitated protein was collected by centrifugation. A 10 mM potassium phosphate buffer was added thereto for complete dissolution. The obtained solution was applied to a Sephadex G-25 gelfiltration support (GE Healthcare) for desalting. Thus, a crude enzyme liquid was obtained.

500 μM 1-O-β-vanillyl glucose (5 μl), a 100 mM citric acid buffer (pH 5.6) (304, and 2 mM cyanidin 3-glucoside (5 μl) were added to the crude enzyme liquid (15 μl). The reaction solution was left at 30° C. for 40 minutes. Then, a 20% phosphoric acid aqueous solution (2.5 μl) was added thereto to terminate the reaction. Insoluble matter was removed by centrifugation, followed by HPLC analysis.

HPLC analysis was performed using a 1.5% phosphoric acid aqueous solution and acetonitrile as eluents and an ODS column (inner diameter×length: 4.6×250 mm; Cosmosil 5C18-MS-II; Nacalai Tesqueu). After separation with a linear gradient of 17% to 40% acetonitrile at a flow rate of 1 ml/min (20 minutes), detection was carried out using a photodiode array detector. The upper chart in FIG. 1 shows HPLC analysis results. The results were compared with results obtained by analyzing a commercially available product used as a reference product in the same manner (the bottom chart in FIG. 1) in terms of retention time. As a result, the reaction product was found to be cyanidin 3,5-O-β-diglucoside. This means that a glycosyl transfer reaction in accordance with the following formula took place:

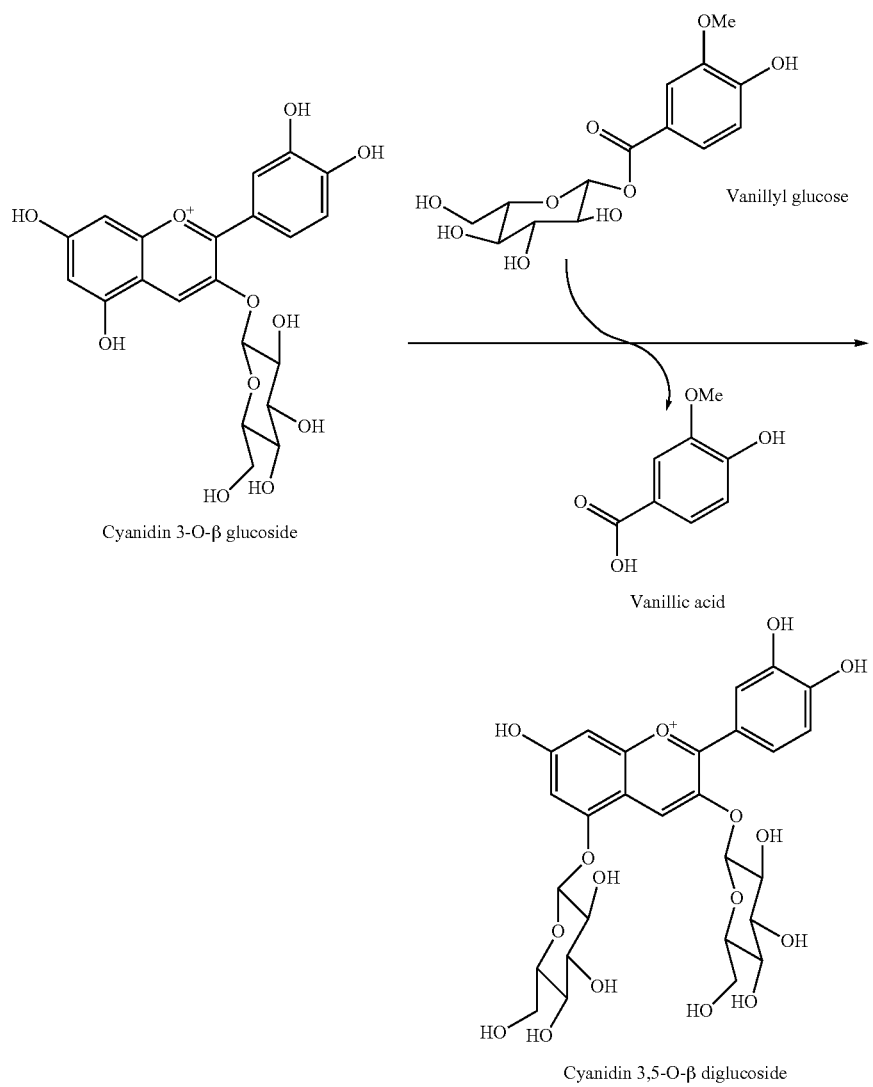

The above results revealed that 1-O-β-vanillyl glucose functions as a sugar donor in a glycosyl transfer reaction catalyzed by an enzyme from pink carnation petals.

(5) Purification of Glycosyltransferase and Physicochemical Properties Thereof

Pink petals of a carnation (variety: "Beam Cherry") were ground into a powder in liquid nitrogen using a mortar and a pestle. The obtained powder was added in a stepwise manner to a 50 mM potassium phosphate buffer (pH 7.2) and dissolved therein via stirring to prevent freezing. The resultant was squeezed using nylon mesh to obtain the solution. Insoluble components such as cell walls were removed from the solution. Further, ammonium sulfate was added in a stepwise manner to the solution so as to result in a final concentration of 35%, followed by sufficient stirring for dissolution. The solution was left at 4° C. for 30 minutes, followed by centrifugation at 4° C. and 15,000×g for 30 minutes. Then, the supernatant was collected. Ammonium sulfate was further added in a stepwise manner thereto so as to result in a final concentration of 55% for complete dissolution. The resultant was left overnight at 4° C., followed by centrifugation at 4° C. and 15,000×g for 30 minutes. A 10 mM potassium phosphate buffer (pH 7.2) was added to the obtained precipitate for complete dissolution, followed by dialysis with a sufficient amount of a 10 mM potassium phosphate buffer (pH 7.2). Thus, a crude enzyme liquid was obtained. All procedures used in this Example were carried out on ice or at 4° C. unless otherwise specified.

The dialyzed solution was applied to TOYOPEARL-DEAE650M (bed volume: 400 ml) that had been equilibrated in advance. The column was washed with a 10 mM potassium phosphate buffer (pH 7.2) at a volume 5 times the column volume (i.e., 5 CV (column volume)), followed by elution with a linear gradient of 0 M to 0.8 M NaCl (5 CV). The eluted protein solution was fractionated (25 ml for each fraction). 1-O-β-vanillyl glucose (3 µl) was added to each fraction (30 µl). Each fraction was evaluated in terms of glycosyltransferase activity in the manner described in (3) above. The active fractions (the 38th to 49th fractions) were collected, followed by dialysis with a sufficient amount of a 10 mM potassium phosphate buffer (pH 7.2).

Ammonium sulfate was added in a stepwise manner to the dialyzed fractions for complete dissolution so as to result in a final concentration of 20%. The resultant was applied to TOYOPEARL-Butyl 650M (Bed volume 80 ml) that had been equilibrated in advance with a 10 mM phosphoric acid buffer containing 20% ammonium sulfate (pH 7.2). The column was washed with a 10 mM phosphoric acid buffer (pH 7.2) containing 20% ammonium sulfate (5 CV), followed by elution with a linear gradient of 20% to 0% ammonium sulfate (10 CV). The eluted protein solution was fractionated (10 ml for each fraction). The glycosyltransferase activity of each fraction (30 µl) was evaluated using 1-O-β-vanillyl glucose (3 µl) in the manner described in (3) above. The active fractions (the 60th to 77th fractions) were collected, followed by dialysis with a sufficient amount of a 10 mM potassium phosphate buffer (pH 7.2).

The dialyzed fractions were applied to Benzamidine Sepharose 4 Fast Flow (high sub) (GE Healthcare; bed volume: 8 ml) that had been equilibrated in advance with a Bz buffer (10 mM potassium phosphate, pH 7.2, 0.5 M NaCl). The column was washed with a benzamidine buffer (5 CV), followed by elution with a linear gradient of 0 mM to 25 mM p-benzamidine (12.5 CV). The eluted protein solution was fractionated (2.5 ml for each fraction). The glycosyltransferase activity of each fraction (30 µl) was evaluated using 1-O-β-vanillyl glucose (3 µl) in the manner described in (3) above. The active fractions (the 25th and 26th fractions) were collected and concentrated using Amicon Ultra-15 (10,000 MWCO, Millipore), followed by buffer substitution with a 10 mM potassium phosphate buffer.

The concentrated fractions were applied to a Superdex 200 10/300 GL column (GE Healthcare) (10 mM potassium phosphate, pH 7.2, 150 mM NaCl) that had been equilibrated in advance with gel filtration buffer. The eluate was fractionated (0.7 ml for each fraction). The glycosyltransferase activity of each fraction (30 µl) was evaluated using 1-O-β-vanillyl glucose (3 µl) in the manner described in (3) above. The active fractions (the 22nd to 25th fractions) were collected and concentrated using Amicon Ultra-15 (10,000 MWCO, Millipore), followed by buffer substitution with a 10 mM potassium phosphate buffer.

The fractions purified by gel filtration were applied to an Resource Q 1-ml column that had been equilibrated in advance with a 10 mM potassium phosphate buffer (pH 7.2). The column was washed with a 10 mM potassium phosphate buffer (pH 7.2) (5 CV), followed by elution with a linear gradient of 0 M to 0.5 M NaCl. The eluted protein solution was fractionated (0.2 ml for each fraction). The glycosyltransferase activity of each fraction (30 µl) was evaluated using 1-O-β-vanillyl glucose (3 µl) in the manner described in (3) above. The active fractions (the 41st to 48th fractions) were collected.

The collected fractions were analyzed by SDS-PAGE (SDS-polyacrylamide gel electrophoresis). As a result, the obtained protein was found to have a molecular weight of approximately 55 kDa. In addition, the reaction optimum pH of the enzyme was examined and thus found to be approximately 5.0 to 5.5. This reaction optimum pH of the enzyme was lower than that of glycosyltransferase (pH 7.5 to 8.0) which has been conventionally known. Therefore, it is thought that the enzyme reaction would proceed even under weakly acidic conditions that conventionally do not allow a enzyme reaction to take place.

(6) Synthesis of Vanillyl Glucose

A hydroxyl group at the 4 position of commercially available vanillic acid (Sigma-Aldrich) and a hydroxyl group of carboxylic acid were benzyl-protected in a dimethylformamide solvent (DMF, Thermo Fisher Scientific K.K.) using benzyl bromide (Sigma-Aldrich). Then, the unreacted product was removed using an open column (silica gel 60 (spherical); Kanto Chemical Co., Inc.) (hexane:ethyl acetate=8:1), followed by purification. The yield was found to be 100%: $^1$H NMR (300 MHz, CDCl$_3$): δ7.65 (1H, dd, H-6), 7.59 (1H, d, H-2), 7.41-7.26 (9H, m, H-benzylic CH$_2$), 6.88 (1H, d, H-5), 5.33 (2H, s, H-benzylic CH$_2$), 5.21 (1H, s, H-benzylic CH$_2$), and 3.92 (3H, s, CH$_3$).

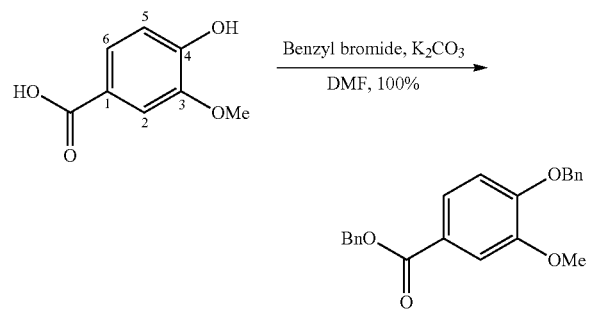

Next, the purified product was hydrolyzed in the presence of lithium hydroxide (Wako Pure Chemical Industries, Ltd.) in a solvent (THF (Kanto Chemical Co., Inc.):H$_2$O:MeOH (Wako Pure Chemical Industries, Ltd.)=3:2:1) so as to remove a benzyl group protecting a hydroxyl group of carboxylic acid. Then, the resultant was purified using an open column (at different concentration ratios of hexane:ethyl acetate=10:1, 4:1, and 0:1) so as to remove the unreacted product and benzyl alcohol. The yield was found to be 58%: $^1$H NMR (300 MHz, CDCl$_3$): δ7.68 (1H, dd, H-6), 7.60 (1H, d, H-2), 7.45-7.25 (5H, m, H-benzylic CH$_2$), 6.90 (1H, d, H-5), 5.25 (2H, s, H-benzylic CH$_2$), and 3.92 (3H, s, CH$_3$).

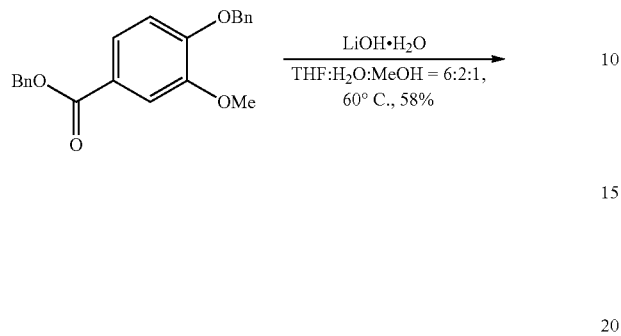

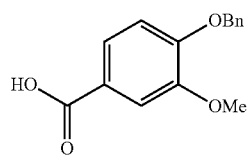

Vanillic acid having a benzyl-protected hydroxyl group at the 4 position and 2,3,4,6-tetrabenzyl glucose having benzyl-protected hydroxyl groups at positions other than the 1 position (Sigma-Aldrich) were condensed in a DMF solvent (at a reaction temperature of 60° C.) using the following condensing agents: 1-ethyl-3-(3-dimethylaminopropyl) carbodiimide hydrochloride (EDCI, Kokusaikagaku Co., Ltd.), 4-dimethylaminopyridine (DMAP, Tokyo Kasei Kogyo), and triethylamine (Et$_3$N, Wako Pure Chemical Industries, Ltd.). The obtained condensate was a mixture comprising α anomer and β anomer at a ratio of 1:2. The condensate was purified using an open column (at different concentration ratios of hexane: ethyl acetate=6:1 and 5:1). A unreacted starting material was removed. The yield was found to be 84%: Molecular MS [M+Na]$^+$ m/z 803.14, $^1$H NMR (300 MHz, CDCl$_3$): δ7.60 (1H, dd, H-6), 7.59 (1H, d, H-2), 7.45-7.26 (60H, m, H-benzylic CH$_2$), 6.90 (1H, d, H-5), 6.55 (1H, d, H-Glc1α, J=3.21), 5.84 (1H, d, H-Glc1β, J=7.65), 5.25 (10H, s, H-benzylic CH$_2$), 4.96-3.56 (94H, m, CH$_3$, H-Glc).

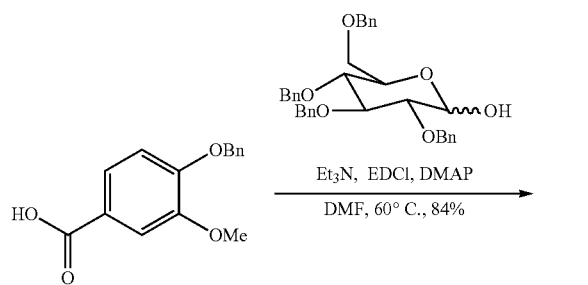

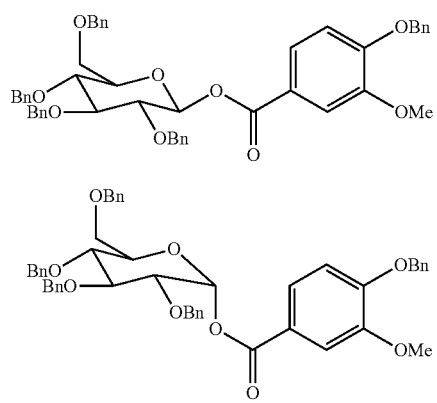

Next, hydrogenation was carried out using a palladium hydroxide charcoal catalyst (Sigma-Aldrich) for deprotection of benzyl groups. Thus, a mixture of α-vanillyl glucose and β-vanillyl glucose was obtained (yield: 81%). Palladium hydroxide was removed via Celite filtration. The obtained mixture was subjected to separation using 10% liquid B comprising eluent A (a 0.1% acetic acid aqueous solution) and eluent B (a 90% methanol aqueous solution) by fractionation HPLC (Develosil C$_{30}$; 10×250 mm; Nomura Chemical) (for 40 minutes). Accordingly, 1-O-α-vanillyl glucose (degree of refining: 99.6%) and 1-O-β-vanillyl glucose (degree of refining: 98.9%) were separately obtained. The degree of refining was calculated based on the HPLC area: Molecular MS [M+Na]$^+$ (m/z: 352.9), α-$^1$H NMR (400 MHz, CD$_3$CD): δ 7.62 (1H, dd, H-6), 7.58 (1H, d, H-2), 6.83 (1H, d, H-5), 6.28 (1H, d, H-Glc1, J=3.66), 3.89 (3H, s, CH$_3$), and 3.83-3.33 (5H, m, H-Glc), β-$^1$H NMR (400 MHz, CD$_3$CD): δ 7.62 (1H, dd, H-2), 7.60 (1H, d, H-6), 6.83 (1H, d, H-5), 5.67 (1H, d, H-Glc1, J=7.79), 3.89 (3H, s, CH$_3$), and 3.83-3.33 (5H, m, H-Glc).

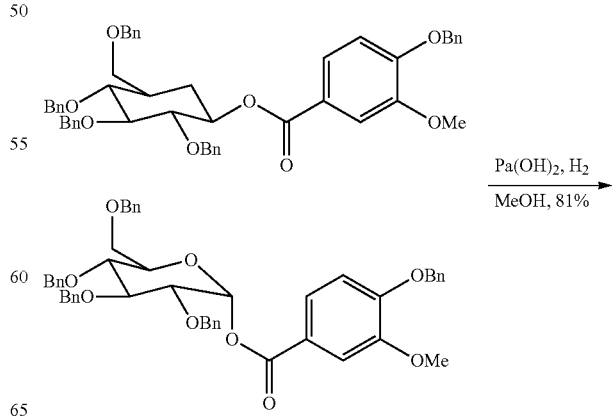

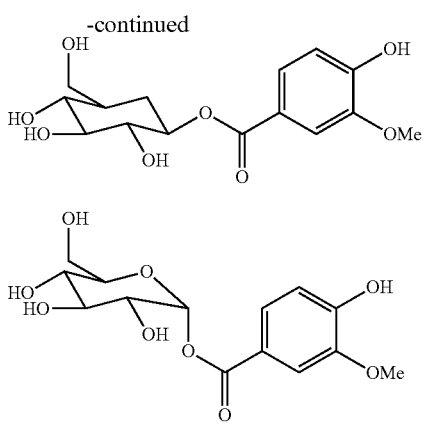

(7) Synthesis of Isovanillyl Glucose

A hydroxyl group at the 3 position of commercially available isovanillic acid (Sigma-Aldrich) and a hydroxyl group of carboxylic acid were benzyl-protected in a DMF solvent using benzyl bromide.

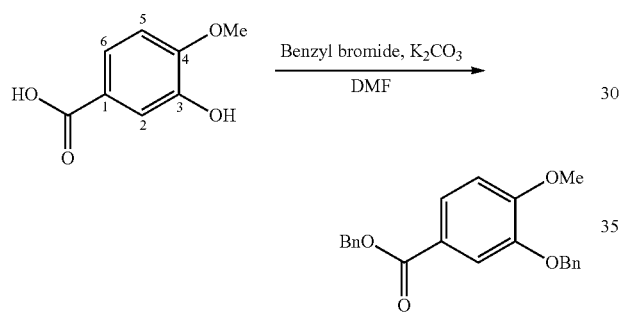

Next, benzyl groups protecting hydroxyl groups of carboxylic acid were removed via hydrolysis in the presence of lithium hydroxide in a solvent (THF:H$_2$O:MeOH=3:2:1). Then, an unreacted product and benzyl alcohol were removed via purification using an open column (at different concentrations of hexane:ethyl acetate of 10:1, 4:1, and 0:1). The yield was found to be 86%: $^1$H NMR (300 MHz, CDCl$_3$): δ7.75 (1H, dd, H-6), 7.65 (1H, d, H-2), 7.45-7.25 (5H, m, H-benzylic CH$_2$), 6.90 (1H, d, H-5), 5.15 (2H, s, H-benzylic CH$_2$), 3.90 (3H, s, CH$_3$).

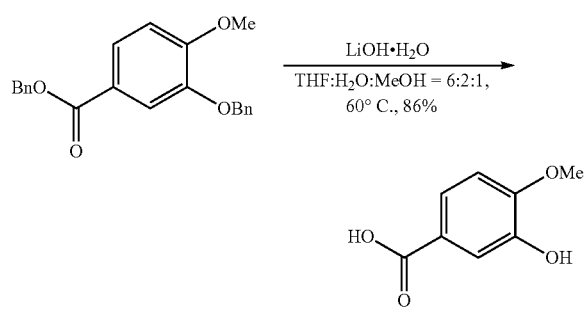

Isovanillic acid having a benzyl-protected hydroxyl group at the 3 position and 2,3,4,6-tetrabenzyl glucose having benzyl-protected hydroxyl groups at positions other than the 1 position were condensed in a DMF solvent (at a reaction temperature of 60° C.) using the following condensing agents: EDCI, DMAP, and Et$_3$N. The obtained condensate was a mixture comprising an α anomer and a β anomer at a ratio of 3:2. The condensate was purified using an open column (at different concentration ratios of hexane:ethyl acetate=6:1 and 5:1) so as to remove an unreacted starting material. The yield was found to be 60%: $^1$H NMR (300 MHz, CDCl$_3$): δ7.82 (1H, dd, H-6), 7.72 (1H, d, H-2), 7.52-7.26 (60H, m, H-benzylic CH$_2$), 6.90 (1H, d, H-5), 6.67 (1H, d, H-Glc1α, J=3.64), 5.96 (1H, d, H-Glc1β, J=8.16), 5.25-3.71 (H, m, CH$_3$, H-Glc).

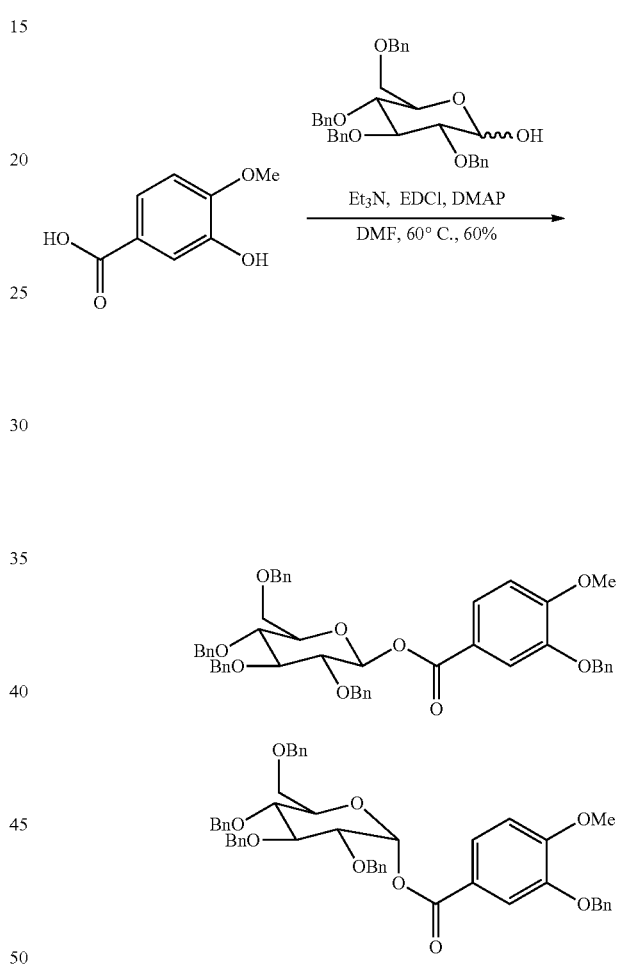

Next, hydrogenation was carried out using a palladium hydroxide charcoal catalyst for deprotection of benzyl groups. Thus, a mixture of α-isovanillyl glucose and β-isovanillyl glucose was obtained (yield: 100%). Palladium hydroxide was removed via Celite filtration. The obtained mixture was subjected to separation using 10% liquid B comprising eluent A (a 0.1% acetic acid aqueous solution) and eluent B (a 90% methanol aqueous solution) by fractionation HPLC (Develosil C$_{30}$; 10×250 mm) (for 40 minutes). Accordingly, 1-O-α-isovanillyl glucose and 1-O-α-isovanillyl glucose were separately obtained: Molecular MS [M+Na]$^+$ m/z 353.0, $^1$H NMR (300 MHz, CD$_3$CD): δ 7.63 (1H, dd, H-6), 7.60 (1H, d, H-2), 7.00 (1H, d, H-5), 6.30 (1H, d, H-Glc1α, J=3.60), 5.67 (1H, d, H-Glc1β, J=8.10), 3.91 (3H, s, CH$_3$), 3.88-2.88 (5H, m, H-Glc).

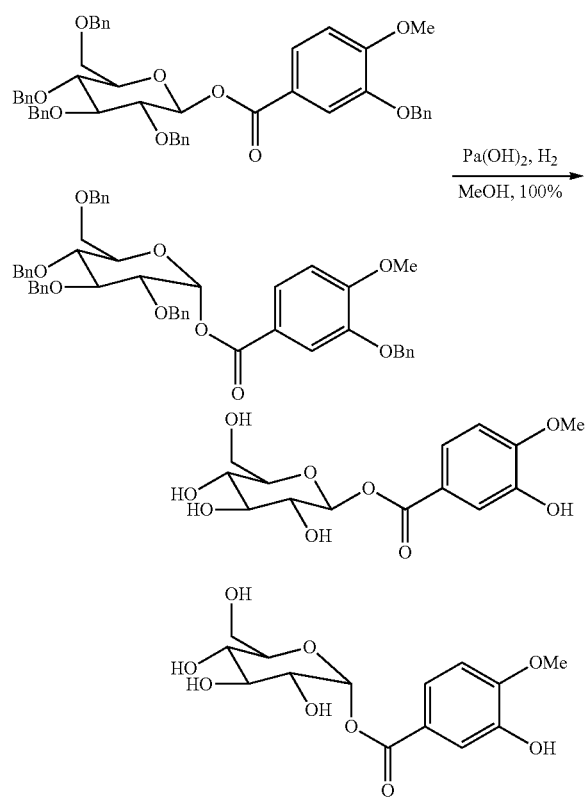

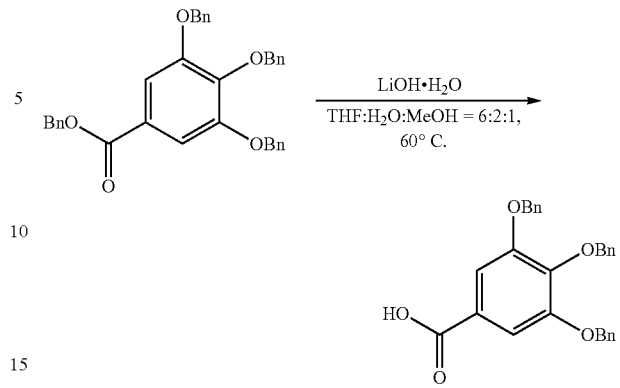

Gallic acid having benzyl-protected hydroxyl groups at the 3, 4, and 5 positions and 2,3,4,6-tetrabenzyl glucose having benzyl-protected hydroxyl groups at positions other than the 1 position were condensed in a DMF solvent (at a reaction temperature of 60° C.) using the following condensing agents: EDCI, DMAP, and Et$_3$N. The condensate was purified using an open column (at different concentration ratios of hexane:ethyl acetate=6:1 and 5:1) so as to remove an unreacted starting material. The obtained condensate was a mixture comprising an α anomer and a β anomer at a ratio of 3:7: Molecular MS [M+Na]$^+$ m/z 985.18, $^1$H NMR (300 MHz, CDCl$_3$): δ7.40-7.11 (92H, m, H-2, 6, 5, H-benzylic CH$_2$), 6.52 (1H, d, H-Glc1α, J=2.40), 5.85 (1H, d, H-Glc1β, J=7.50), 5.16 (18H, s, H-benzylic CH$_2$), 4.99-3.64 (28H, m, H-Glc, H-benzylic CH$_2$).

(8) Synthesis of Glucose Gallate

Hydroxyl groups at the 3, 4, and 5 positions of commercially available gallic acid (Sigma-Aldrich) and a hydroxyl group of carboxylic acid were benzyl-protected in a DMF solvent using benzyl bromide. Then, a unreacted product was removed using an open column (hexane:ethyl acetate=8:1), followed by purification.

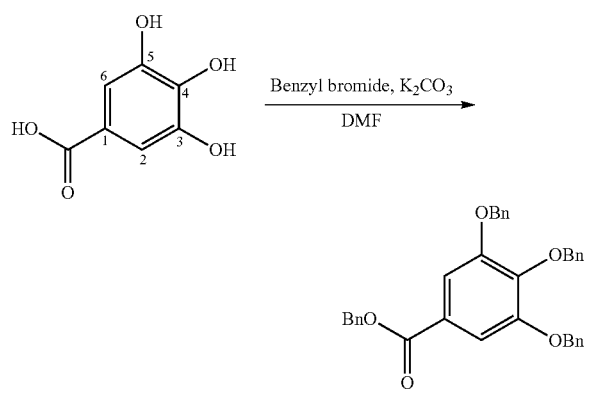

Next, benzyl groups protecting hydroxyl groups of carboxylic acid were removed via hydrolysis in the presence of lithium hydroxide in a solvent (THF:H$_2$O:MeOH=3:2:1). Then, an unreacted product and benzyl alcohol were removed via purification using an open column (at different concentrations of hexane:ethyl acetate of 10:1, 4:1, and 0:1).

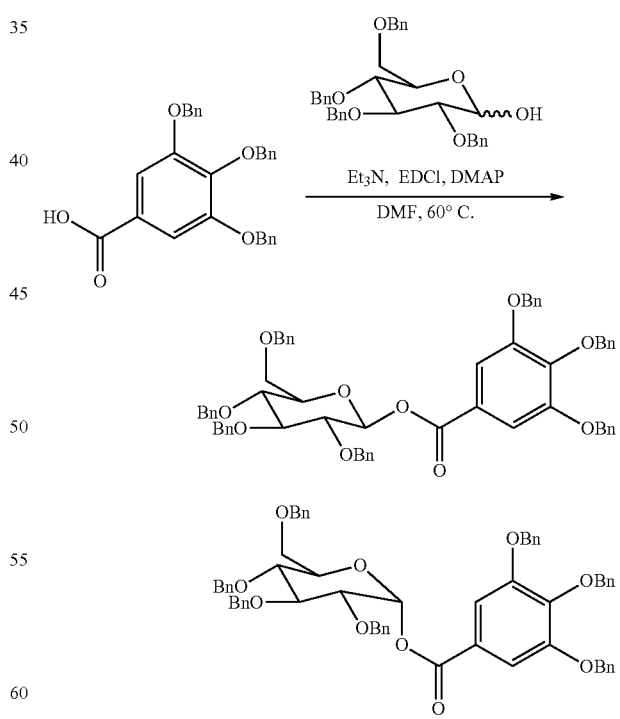

Next, hydrogenation was carried out using a palladium hydroxide charcoal catalyst for deprotection of benzyl groups. Thus, a mixture of α-glucose gallate and β-glucose gallate was obtained. Palladium hydroxide was removed via Celite filtration. The obtained mixture was subjected to separation using 10% liquid B comprising eluent A (a 0.1% acetic acid aqueous solution) and eluent B (a 90% methanol aqueous solution) by fractionation HPLC (Develosil $C_{30}$; 10×250 mm; Nomura Chemical) (for 40 minutes). Accordingly, 1-O-α-galloyl glucose and 1-O-β-galloyl glucose were separately obtained: Molecular MS [M+Na]$^+$ m/z 354.9, α-$^1$H NMR (400 MHz, $CD_3CD$): δ 7.10 (2H, s, H-2, 6), 6.25 (1H, d, H-Glc1, J=3.66), 3.82-3.32 (5H, m, H-Glc), β-$^1$H NMR (400 MHz, $CD_3CD$): δ 7.10 (2H, s, H-2, 6), 5.63 (1H, d, H-Glc1, J=7.79), 3.84-3.32 (5H, m, H-Glc).

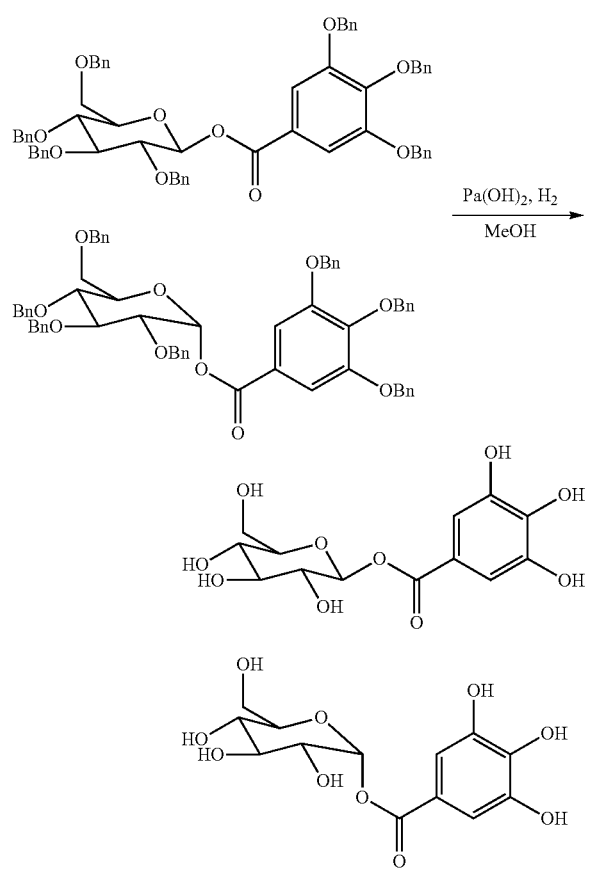

(8) Verification of Glycosyl Transfer Reaction Using Each Obtained Compound as a Sugar Donor An enzyme reaction was carried out at 30° C. for 15 minutes in a reaction solution obtained by adding a citric acid buffer (pH 5.6) to a crude enzyme obtained from pink petals of a carnation (variety: "Beam Cherry") (61 μg), cyanidin β-glucoside (200 μM), and a sugar donor (1-O-β-vanillyl glucose extracted from a carnation or any of synthesized 1-O-vanillyl glucose (in the α or β form), 1-O-isovanillyl glucose (in the α or β form), and 1-O-galloyl glucose (in the α or β form)) (500 μM) to a final volume of 30 μl. The reaction was terminated by adding a 20% phosphoric acid aqueous solution to the reaction liquid so as to result in a final phosphoric acid concentration of 1%, followed by centrifugation. The obtained supernatant was subjected to separation using an HPLC (Chromolith Speed ROD; 4.6×50 mm; Merck) with a linear gradient (5 minutes) of 18% to 28% liquid B containing eluent A (a 1.5% phosphoric acid aqueous solution) and eluent B (a 90% methanol aqueous solution) (flow rate: 3.0 ml/min; 520 nm), followed by analysis. The relative activity of the enzyme on each sugar donor was calculated based on the HPLC chromatogram area of a reaction product (cyanidin 3,5-O-β diglucoside) at a wavelength of 505 nm. The table below shows the results.

TABLE 2

|  | Relative activity of an enzyme on a sugar donor (when synthetic 1-O-β-vanillyl glucose is set as 100) |
| --- | --- |
| 1-O-β-vanillyl glucose (synthetic) | 100 |
| 1-O-β-vanillyl glucose (from carnation) | 97.9 |
| 1-O-α-vanillyl glucose (synthetic) | 1.7 |
| 1-O-β-isovanillyl glucose (synthetic) | 23.1 |
| 1-O-α-isovanillyl glucose (synthetic) | Not detectable |
| 1-O-β-galloyl glucose (synthetic) | 2.4 |

Example 2

(1) Extraction of Glycosyltransferase

Petals of a carnation (variety: "Beam Cherry") that had been quickly frozen in liquid nitrogen and stored at −80° C. (wet weight: 400 g) were sufficiently disrupted in an extraction buffer (100 mM potassium phosphate, pH 7.2) (1500 ml) using a mixer. All procedures described below were carried out on ice or at 4° C. unless otherwise specified. Disruption was further carried out using a homogenizer (Polytron, KINEMATICA) at 15,000 rpm for 10 minutes. The supernatant was collected by centrifugation at 20,000×g and 4° C. for 20 minutes. The above procedure was repeated twice such that approximately 3,000 ml of a crude extraction liquid was obtained from 800 g (in total) of petals.

(2) Purification of Glycosyltransferase (a) Fractionation Via Ammonium Sulfate Precipitation Granular ammonium sulfate was added in a stepwise manner to the obtained crude extraction liquid and completely dissolved therein via stirring with a magnetic stirrer so as to result in a concentration of 35%. The resultant was left at 4° C. for 2 hours. Then, the supernatant was collected via centrifugation at 20,000×g at 4° C. for 20 minutes. Granular ammonium sulfate was further added in a stepwise manner to the collected supernatant and completely dissolved therein via stirring with a magnetic stirrer so as to result in a concentration of 55%. The resultant was left overnight at 4° C., followed by centrifugation at 20,000×g and 4° C. for 20 minutes. Thus, the precipitate was collected. The collected precipitate was dissolved in a 10 mM phosphoric acid buffer (pH 7.2) (3000 ml). The resultant was passed through a dialysis membrane, followed by dialysis with a 10 mM phosphoric acid buffer (pH 7.2) (6 L). The phosphoric acid buffer was replaced by a fresh phosphoric acid buffer 4 to 12 hours thereafter. The final volume of the phosphoric acid buffer used for dialysis was 4000 times that of the sample inside the dialysis membrane.

(b) Separation by DEAE Sepharose Fast Flow

The sample solution dialyzed in (a) above was applied to a glass column (bed volume: 350 ml) filled with a DEAE sepharose FF ion exchanger (GE Healthcare) that had been equilibrated in advance with a 10 mM potassium phosphate buffer (pH 7.2), followed by washing with a 10 mM phosphoric acid buffer (pH 7.2) (1250 ml). Then, protein separation was carried out using a 10 mM potassium phosphate buffer (pH 7.2) (1000 ml) containing liquid A (a 10 mM phosphoric acid buffer (pH 7.2)) and liquid B (0.8 M NaCl) with a linear gradient of 0% to 100% liquid B. The separated protein solution was fractionated (25 ml for each fraction). The glycosylation enzyme activity of each fraction was determined using cyanidin-3-O-β-glucoside as a substrate and 1-O-β-vanillyl glucose as a sugar donor. The active fractions (the 31st to 45th fractions) were collected and dialyzed using a sufficient volume of a 10 mM potassium phosphate buffer (pH 7.2).

(c) Separation Using TOYOPEARL-Butyl

Granular ammonium sulfate was gradually added to the fraction dialyzed in (b) above so as to result in a concentration of 20% and dissolved therein. The obtained sample solution was applied to a TOYOPEARL-Butyl-650M support column (Tosoh Corporation; 50 mm×100 mm; bed volume: 250 ml) that had been equilibrated in advance with a butyl equilibration buffer (10 mM potassium phosphate, 20% ammonium sulfate, pH 7.2). The column was washed with a butyl equilibration buffer (1250 ml). Then, protein separation was carried out using liquid A liquid (butyl equilibration buffer) and liquid B (10 mM potassium phosphate buffer) (pH 7.2) with a linear gradient of 0% to 100% liquid B (1250 ml). The separated protein solution was fractionated (20 ml for each fraction). The glycosylation enzyme activity of each fraction was determined using cyanidin-3-O-β-glucoside as a substrate and 1-O-β-vanillyl glucose as a sugar donor. The active fractions (the 63rd to 85th fractions) were collected and concentrated using Amicone-15ultra (Millipore). Then, the buffer was replaced by a 10 mM potassium phosphate buffer.

(d) Separation Using Benzamidine Sepharose

The sample dialyzed in (c) was applied to a Benzamidine Sepharose 4 Fast Flow column (bed volume: 8 ml) that had been equilibrated in advance with a Bz washing buffer (10 mM potassium phosphate, pH 7.2, 0.5 M NaCl). The column was washed with a Bz washing buffer (40 ml). Then, protein separation was carried out using liquid A (Bz washing buffer) and liquid B (Bz elution buffer (10 mM potassium phosphate, pH 7.2, 0.5 M NaCl, 20 mM 4-amino benzamidine)) with a linear gradient of 0% to 100% liquid B (80 ml). The separated protein solution was fractionated (2 ml for each fraction). The glycosylation enzyme activity of each fraction was determined using cyanidin-3-O-β-glucoside as a substrate and 1-O-β-vanillyl glucose as a sugar donor. The active fractions (the 27th to 33rd fractions) were collected and concentrated using Amicone-15ultra. Then, the buffer was replaced by a 10 mM potassium phosphate buffer.

(e) Separation Via Gel Filtration

The sample solution obtained in (d) above was applied to Superdex 7510/300GL (GE Healthcare) that had been equilibrated in advance with gel filtration buffer (10 mM potassium phosphate, pH 7.2, 150 mM NaCl). Protein separation was carried out by allowing the gel filtration buffer to pass through the column at a flow rate of 0.5 ml/min. The separated protein solution was fractionated (500 μl for each fraction). The glycosylation enzyme activity of each fraction was determined using cyanidin-3-O-β-glucoside as a substrate and 1-O-β-vanillyl glucose as a sugar donor. The active fractions (the 29th to 32nd fractions) were collected and concentrated using Amicone-15ultra. Then, the buffer was replaced by a 10 mM potassium phosphate buffer.

(f) Separation Using Resouce ETH

The protein solution obtained in (e) above was applied to Resouce ETH (GE Healthcare) that had been equilibrated in advance with an ETH equilibrated buffer (10 mM potassium phosphate, pH 7.2, 35% ammonium sulfate). The column was washed with an ETH equilibrated buffer. Then, protein separation was carried out using liquid A (ETH equilibration buffer) and liquid B (ETH elution buffer (10 mM potassium phosphate, pH 7.2, 15% ammonium sulfate)) with a linear gradient of 0% to 100% liquid B for 19 minutes (flow rate: 0.8 ml/min). The separated protein solution was fractionated (300 μl for each fraction). The glycosylation enzyme activity of each fraction was determined using cyanidin-3-O-β-glucoside as a substrate and 1-O-β-vanillyl glucose as a sugar donor. The active fractions (the 20th to 25rd fractions) were collected and concentrated using Amicone-15ultra. Then, the buffer was replaced by a 10 mM potassium phosphate buffer.

(g) Separation Using HiTrap Butyl

A saturate ammonium sulfate aqueous solution was added to the protein solution obtained in (1) above so as to result in a final concentration of 20%. The sample solution was applied to HiTrap Butyl (GE Healthcare) that had been equilibrated in advance with a butyl equilibration buffer (10 mM potassium phosphate, 20% ammonium sulfate, pH 7.2). The column was washed with a butyl equilibration buffer (5 ml). Then, protein separation was carried out using liquid A (butyl equilibration buffer) and liquid B (butyl elution buffer (10 mM potassium phosphate buffer, pH 7.2, 10% ethylene glycol) with a linear gradient of 0% to 100% liquid B for 19 minutes (flow rate: 1 ml/min). The separated protein solution was fractionated (300 μl for each fraction). The glycosylation enzyme activity of each fraction was determined using cyanidin-3-O-β-glucoside as a substrate and 1-O-β-vanillyl glucose as a sugar donor. The active fractions (the 43rd to 48th fractions) were collected and concentrated using Amicone-15ultra (Millipore). The buffer was replaced by a 10 mM potassium phosphate buffer.

Figure 2:
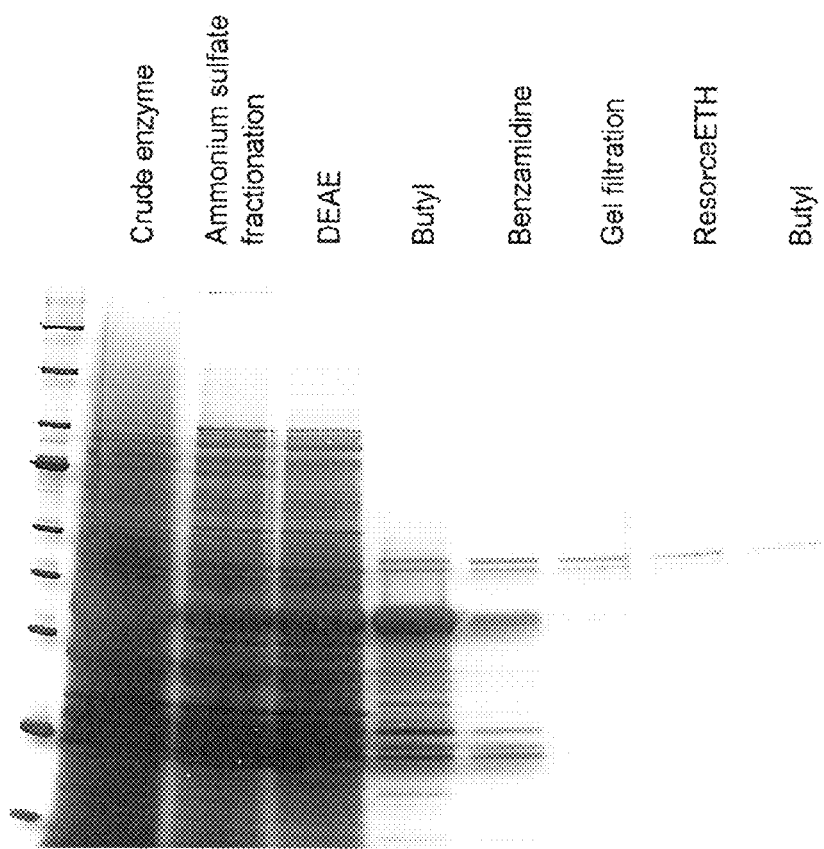
FIG. 2 shows results obtained by separating a glycosyltransferase purified from a carnation by SDS-PAGE and visualizing the glycosyltransferase by a silver staining method.

The refined protein was separated by SDS-PAGE and visualized by a silver staining method for confirmation. FIG. 2 shows the results.

(h) Determination of Glycosylation Enzyme Activity of Each Fraction

The glycosylation enzyme activity was determined in (b) to (g) above in the manner described below using cyanidin-3-O-β-glucoside as a substrate and 1-O-β-vanillyl glucose as a sugar donor.

Fractions obtained by fractionation were subjected to buffer replacement (100 mM citric acid buffer (pH 5.6)) using a SephadexG-25 support (GE Healthcare). 10 mM 1-O-β-vanillyl glucose (3 μl) and 2 mM cyanidin-3-O-β-glucoside (3 μl) were added to a crude enzyme liquid (30 μl) The reaction solution was left at 30° C. for 30 minutes. Then, a 20% phosphoric acid aqueous solution (2 μl) was added thereto to terminate the reaction. Insoluble matter was removed by centrifugation, followed by HPLC analysis.

HPLC analysis was performed using a 1.5% phosphoric acid aqueous solution and a 90% methanol aqueous solution as eluents and a Chromolith Performance RP-18e column (4.6×100 mm; Merck). Separation was carried out with a linear gradient of 17% to 40% using a 90% methanol aqueous solution at a flow rate of 3 ml/min (4 minutes). Generation of cyanidin-3,5-O-β-diglucoside was confirmed based on the absorbance at a wavelength of 520 nm using a ultraviolet-visible detector.

(3) Amino Acid Sequence Analysis of a Glycosyltransferase Protein

The amino acid sequence of the purified glycosyltransferase protein was analyzed using a high sensitivity protein internal sequence analysis service (by commission) and a medium sensitivity N-terminal amino acid sequence analysis service (by commission) provided by APRO Science Co., Ltd. (Naruto city, Tokushima, Japan). As a result of protein internal sequence analysis, the following three types of amino acid sequences were found to be present in the protein: "GLEYYNNLVNA (SEQ ID NO: 5);" "GTQPHVTLLH (SEQ ID NO: 6);" and "FTPXETELLTG (SEQ ID NO: 7)." In addition, the N-terminal amino acid sequence analysis results revealed that the amino acid sequence of the protein starts with a "SEFDRLDFPK (SEQ ID NO: 8)" sequence. In addition, the results of N-terminal amino acid sequence analysis further revealed that the protein comprises two types of amino acid sequences ("EFDRLDFPKH (SEQ ID NO: 9)" and "PSEFDRLDFP (SEQ ID NO: 10)") in addition to the above. Therefore, it was assumed that the N-terminus was degraded during purification or the substrate specificity of the enzyme processed in plants was low.

(4) Isolation of cDNA Encoding a Glycosyltransferase (from a Carnation)

RNA was extracted from petals of a carnation (variety: "Beam Cherry") by the modified GTC/CsCl density gradient centrifugation method (Chirgwin et al., 1979). Each tissue disc was sufficiently pulverized in liquid nitrogen using a mortar and a pestle. Each resultant was transferred to a 50-ml polypropylene centrifuge tube, followed by complete vaporization of liquid nitrogen at −80° C. Then, a GTC solution (4.23 M guanidine thiocyanate, 25 mM trisodium citrate, 100 mM 2-mercaptoethanol, 0.5% sodium N-lauroylsarcosinate) (3 ml) was added thereto, which was immediately followed by sufficient mixing. The mixture was left at room temperature for 30 minutes, followed by centrifugation at 20,000×g for 20 minutes. The supernatant was transferred to a new centrifuge tube, followed by centrifugation again at 20,000×g for 20 minutes. Thus, insoluble matter was completely removed. The obtained GTC extraction liquid was added to a 5-ml ultracentrifuge tube (Beckman Coulter Inc., Fullerton, Calif.) into which a cesium chloride solution (5.7 M CsCl, 0.1 M EDTA, pH 7.5) (2.2 ml) had been dispensed such that the liquid phase was formed on the solution phase, followed by ultracentrifugation at 70,000 rpm (TL-100 Ultracentrifuge, TLA110 roter, Beckman Coulter Inc.) for 3 hours. Precipitated total RNA was suspended in a TE-SDS buffer (10 mM Tris-HCl, pH 8.0, 1 mM EDTA, 0.1% SDS) (300 pd). Poly (A)+RNA was purified from the obtained total RNA using Oligotex-dT<super> (TaKaRa Bio Inc., Shiga, Japan) in accordance with the manual of the kit.

Full-length cDNA was synthesized from poly(A)+RNA using a GeneRacer (trademark) Kit (Invitrogen corp., CA) by an oligo-capping method in accordance with the manual of the kit. Synthesized cDNA was aliquoted and stored at −80° C. immediately before use. 3'-RACE cDNA was synthesized from the above poly(A)+RNA using a 3'-Full RACE Core Set (TaKaRa Bio Inc.) in accordance with the manual of the kit.

A DNA fragment (approximately 600 bp) was obtained by PCR (94° C., 30 seconds, 46° C., 30 seconds, 72° C., 1 minute) using the preliminarily synthesized 3'-RACE cDNA as a template and degenerate primers ("GGN ACN CAR CCN CAY GTN AC" (SEQ ID NO: 11) and "TTY ACN CCN GAY GAR ACN GA" (SEQ ID NO: 12)) designed based on amino acid sequences ("GTQPHVTLLH" (SEQ ID NO: 6) and "FTPXETELLTG" (SEQ ID NO: 7)) obtained as a result of amino acid internal sequence analysis of the glycosyltransferase protein. The obtained cDNA fragment was ligated to a cloning vector pGEM-T easy (Promega) using Ligation Mix mighty (Takara Bio inc.), followed by transformation of the *Escherichia coli* DH5α strain. A plasmid was extracted from the obtained colony, followed by DNA nucleotide sequence analysis using an ABI PRISM 3100 genetic analyzer (Applied Biosystems Japan Ltd., Tokyo, Japan). The obtained DNA nucleotide sequence was compared with the database using BLASTX of the DNA Databank of Japan (DDBJ). A series of DNA nucleotide sequence analyses were carried out using Genetyx WIN ver. 5.0 (Genetyx Corp., Tokyo, Japan).

PCR was performed using the preliminarily synthesized full-length cDNA as a template, a primer ("GGAAGTCGGGGGCCACCATTCTTCC" (SEQ ID NO: 13)) designed based on the DNA nucleotide sequence of the obtained cDNA fragment, and a GeneRacer5' primer. The obtained PCR product was purified by an ethanol precipitation method. A cDNA fragment (approximately 550 bp) was obtained by nested PCR using the purified PCR product as a template and primers designed based on the DNA nucleotide sequence of the cDNA fragment. The cDNA nucleotide sequence of the obtained cDNA fragment was determined via cloning into a pGEM-Teasy vector in the aforementioned manner.

cDNA comprising the sequence starting from the first ATG of the glycosyltransferase protein was obtained by PCR using the preliminarily synthesized 3'-RACE cDNA as a template, a primer ("ATGAACATGTCATGCAAGTTTGAAATTG" (SEQ ID NO: 14)) designed to comprise a sequence ranging from the determined cDNA 5'-end fragment to the first ATG, and a 3 site 3' adaptor primer (Takara Bio inc.). The obtained cDNA was cloned in the above manner for determination of the DNA nucleotide sequence. FIG. 3 shows the determined cDNA sequence, the predicted nucleotide sequence (SEQ ID NO: 2), and the predicted amino acid sequence (SEQ ID NO: 1) encoded by the nucleotide sequence.

In FIG. 3, the sequences (SEQ ID NOS: 5 to 7) identified as a result of amino acid internal sequence analysis of the purified glycosyltransferase protein were underlined. In addition, the amino acid sequence (SEQ ID NO: 8) identified based on the N-terminal amino acid sequence was underlined and indicated in boldface. cDNA was found to have a full length of 1749 bp and to encode a protein comprising 502 amino acid residues. As a result of cDNA nucleotide sequence analysis and N-terminal amino acid sequence analysis, it was presumed that the enzyme comprising 502 amino acid residues was translated, followed by amino acid removal via processing. In addition, as a result of amino acid motif search on the database, it was suggested that the sequence subjected to processing contained a vacuolar transfer signal sequence.

(5) Expression of the Carnation-Derived Glycosyltransferase Gene in *Escherichia coli*

PCR was performed using a sense primer ("ATGTCGAGTTTGACCGCCTTGACTTTC" (SEQ ID NO: 15))

designed so as to add a methionine residue for the initiation of translation at the N-terminus that had been revealed as a result of analysis of the N-terminal amino acid sequence of the glycosyltransferase and an antisense primer ("GTAGAAG-TACGTATGTG" (SEQ ID NO: 16)) designed so as to lack a stop codon. The PCR product was ligated to a pTrcHis2-TOPO vector (Invitrogen) using a pTrcHis2-TOPO TA expression Kit (Invitrogen), followed by transformation of the *Escherichia coli* JM109 strain. DNA was extracted from the transformed *Escherichia coli* and the DNA nucleotide sequence was analyzed in the above manner. Accordingly, the direction of cDNA introduction and the nonoccurrence of a PCR-induced nucleotide substitution were confirmed.

The transformed *Escherichia coli* was seeded on an LB medium containing 50 μl/ml ampicillin (5 ml), followed by shake culture at 30° C. for 4 hours. Then, IPTG was added thereto to result in 1 mM, followed by shake culture at 16° C. for 2 hours. The cultured *Escherichia coli* was harvested via centrifugation at 1,800×g. The medium was removed therefrom. A 0.1 M citric acid buffer (pH 5.6) (150 μl) was added thereto, followed by sufficient mixing. The resultant was repeatedly subjected to ultrasonication on ice 3 times for 10 seconds (output: 4; duty: 70) using a ultrasonic disintegrator (UD-201, TOMY SEIKO Co., Ltd., Tokyo, Japan), followed by centrifugation at 20,000×g. The supernatant was transferred to a new centrifuge tube and designated as a crude enzyme liquid.

Figure 4:
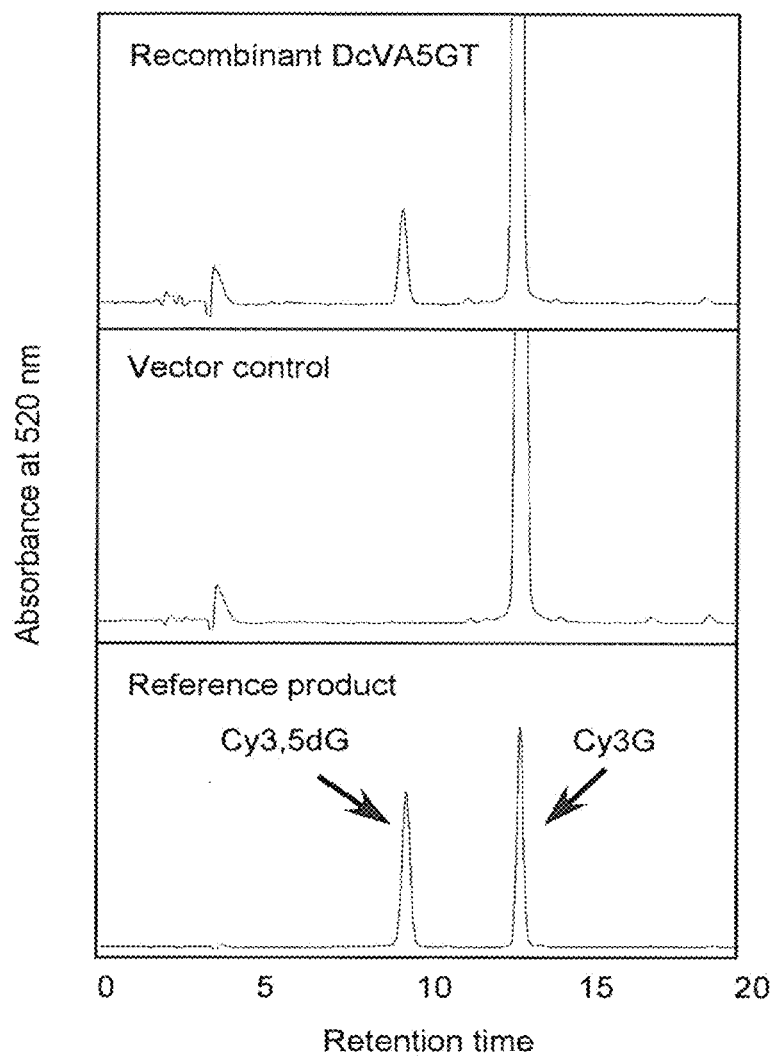
FIG. 4 shows HPLC analysis results indicating generation of cyanidin 3,5-O-β-diglucoside from cyanidin 3-O-β-glucoside as a result of glycosyl transfer reaction with the use of crude enzyme liquid obtained from *Escherichia coli* transformed with the carnation-derived glycosyltransferase gene.

A reaction was induced in a reaction liquid containing the crude enzyme liquid (20 μl), a 0.1M citric acid buffer (pH 5.6) (20 μA), cyanidin-3-O-β-glucoside (5 μl), and 1-O-β-vanillyl glucose (5 μl) at 30° C. for 3 hours. Then, a 20% phosphoric acid aqueous solution (2.5 μl) was added thereto to terminate the reaction. The insoluble protein was removed via centrifugation at 20,000×g. Thereafter, the reaction product was confirmed by HPLC analysis. HPLC analysis was performed using a 1.5% phosphoric acid aqueous solution and methanol as eluents and a Develosil ODS-SR-5 column (4.6×250 mm; Nomura Chemical). Separation was carried out with a linear gradient of 22% to 60% methanol at a flow rate of 1 ml/min (20 minutes). Generation of cyanidin 3,5-O-β-diglucoside was confirmed based on the absorbance at a wavelength of 520 nm using a photodiode array detector (FIG. 4). No product was confirmed in a crude enzyme liquid obtained as a control from *Escherichia coli* that had been transformed with a vector transfected with the LacZ gene provided with the kit. This indicated that the gene consisting of the nucleotide sequence (SEQ ID NO: 2) shown in FIG. 3 encodes an enzyme protein capable of transferring glucose to the 5 position of the anthocyanin skeleton using vanillyl glucose as a sugar donor.

Example 3

(1) Isolation of cDNA Encoding Glycosyltransferase (from a *Delphinium*)

RNA was extracted from petals of a delphinium (variety: "Marine Blue") by the modified GTC/CsCl density gradient centrifugation method (Chirgwin et al., 1979). Each tissue disc was sufficiently pulverized in liquid nitrogen using a mortar and a pestle. The resultant was transferred to a 50-ml polypropylene centrifuge tube, followed by complete vaporization of liquid nitrogen at −80° C. Then, a GTC solution (4.23 M guanidine thiocyanate, 25 mM trisodium citrate, 100 mM 2-mercaptoethanol, 0.5% sodium N-lauroylsarcosinate) (3 ml) was added thereto, which was immediately followed by sufficient mixing. The mixture was left at room temperature for 30 minutes, followed by centrifugation at 20,000×g for 20 minutes. The supernatant was transferred to a new centrifuge tube, followed by centrifugation again at 20,000×g for 20 minutes. Thus, insoluble matter was completely removed. The obtained GTC extraction liquid was added to a 5-ml ultracentrifuge tube (Beckman Coulter Inc., Fullerton, Calif.) into which a cesium chloride solution (5.7 M CsCl, 0.1M EDTA, pH 7.5) (2.2 ml) had been dispensed such that the liquid phase was formed on the solution phase, followed by ultracentrifugation at 70,000 rpm (TL-100 Ultracentrifuge, TLA110 roter, Beckman Coulter Inc.) for 3 hours. Precipitated total RNA was suspended in a TE-SDS buffer (10 mM Tris-HCl, pH 8.0, 1 mM EDTA, 0.1% SDS) (300 μl). Poly(A)$^+$RNA was purified from the obtained total RNA using Oligotex-dT<super> (TaKaRa Bio Inc., Shiga, Japan) in accordance with the manual of the kit.

Full-length cDNA was synthesized from poly(A)$^+$RNA using a GeneRacer (trademark) Kit (Invitrogen corp., CA) by an oligo-capping method in accordance with the manual of the kit. Synthesized cDNA was aliquoted and stored at −80° C. immediately before use. 3'-RACE cDNA was synthesized from the above poly(A)$^+$RNA using a 3'-Full RACE Core Set (TaKaRa Bio Inc.) in accordance with the manual of the kit.

A DNA fragment (approximately 600 bp) was obtained by PCR (94° C., 30 seconds, 46° C., 30 seconds, 72° C., 1 minute) using the preliminarily synthesized 3'-RACE cDNA as a template and degenerate primers ("GGN ACN CAR CCN CAY GTN AC" (SEQ ID NO: 11) and "TTY ACN CCN GAY GAR ACN GA" (SEQ ID NO: 12)) designed based on amino acid sequences ("GTQPHVTLLH" (SEQ ID NO: 6) and "FTPXETELLTG" (SEQ ID NO: 7)) obtained as a result of amino acid internal sequence analysis of the glycosyltransferase protein. The obtained cDNA fragment was ligated to a cloning vector pGEM-T easy (Promega) using Ligation Mix mighty (Takara Bio inc.), followed by transformation of the *Escherichia coli* DH5α strain. A plasmid was extracted from the obtained colony, followed by DNA nucleotide sequence analysis using an ABI PRISM 3100 genetic analyzer (Applied Biosystems Japan Ltd., Tokyo, Japan). The obtained DNA nucleotide sequence was compared with the database using BLASTX of the DNA Databank of Japan (DDBJ). A series of DNA nucleotide sequence analyses were carried out using Genetyx WIN ver. 5.0 (Genetyx Corp., Tokyo, Japan).

Figure 5:
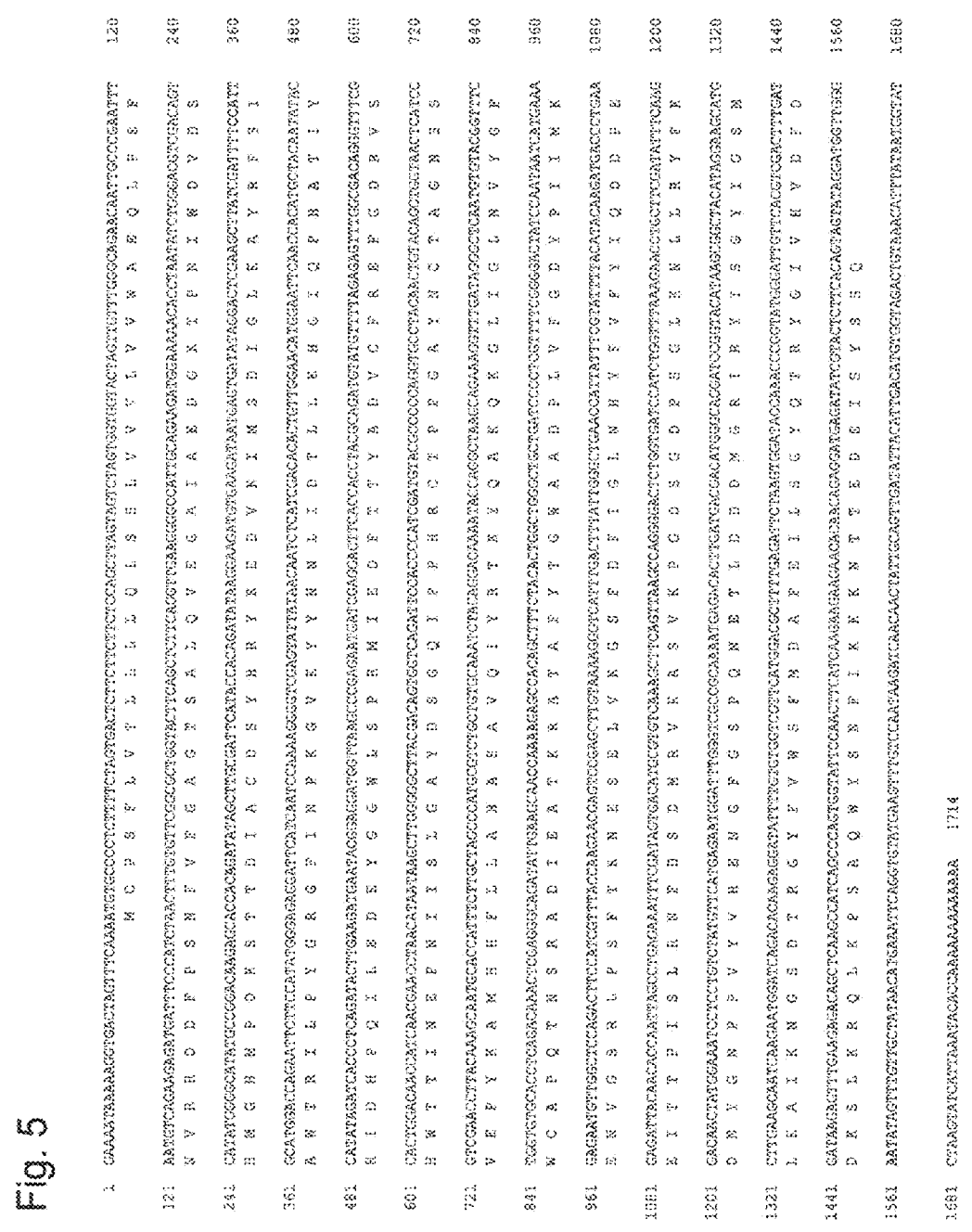

PCR was performed using the preliminarily synthesized full-length cDNA as a template, a primer ("CTGGTTGCT-TCAATATCTGCCCTCG" (SEQ ID NO: 17)) designed based on the DNA nucleotide sequence of the obtained cDNA fragment, and a GeneRacer5' primer. The obtained PCR product was purified by an ethanol precipitation method. A cDNA fragment (approximately 550 bp) was obtained by nested PCR using the purified PCR product as a template and primers designed based on the DNA nucleotide sequence of the cDNA fragment. The cDNA nucleotide sequence of the obtained cDNA fragment was determined via cloning into a pGEM-Teasy vector in the aforementioned manner. cDNA comprising the sequence starting from the first ATG of the glycosyltransferase protein was obtained by PCR using the preliminarily synthesized 3'-RACE cDNA as a template, a primer ("ATGTGCCCCTCTTTTCTAGTGACTC" (SEQ ID NO: 18)) designed to comprise a sequence ranging from the determined cDNA 5'-end fragment to the first ATG, and a 3 site 3' adaptor primer (Takara Bio inc.). The obtained cDNA was cloned in the above manner for determination of the DNA nucleotide sequence. FIG. 5 shows the determined cDNA sequence, the predicted nucleotide sequence (SEQ ID NO: 4), and the predicted amino acid sequence (SEQ ID NO: 3) encoded by the nucleotide sequence.

cDNA isolated in the above manner was found to have a full length of 1701 bp and to encode a protein comprising 505 amino acid residues. As a result of amino acid motif search on the database, it was suggested that a sequence of 30 aminoacid residues at the N-terminus of the amino acid sequence contained a vacuolar transfer signal sequence.

(2) Expression of the *Delphinium*-Derived Glycosyltransferase Gene in *Escherichia coli*

PCR was performed using a sense primer ("ATG CCC GAA TTT AAT GTC AG" (SEQ ID NO: 19)) designed so as to add a methionine residue for the initiation of translation to a sequence from which 28 amino acid residues at the N-terminus predicted as corresponding to vacuolar transfer signals of DgVA7GT had been removed and an antisense primer ("CTG TGA AGA GTA CGA TAT C" (SEQ ID NO: 20)) designed so as to lack a stop codon. The PCR product was ligated to a pTrcHis2-TOPO vector (Invitrogen) using a pTrcHis2-TOPO TA expression Kit (Invitrogen), followed by transformation of the *Escherichia coli* JM109 strain. DNA was extracted from the transformed *Escherichia coli* and the DNA nucleotide sequence was analyzed in the above manner. Accordingly, the direction of cDNA introduction and the nonoccurrence of a PCR-induced nucleotide substitution were confirmed.

The transformed *Escherichia coli* was seeded on an LB medium containing 50 µl/ml ampicillin (5 ml), followed by shake culture at 30° C. for 4 hours. Then, IPTG was added thereto to result in 1 mM, followed by shake culture at 16° C. for 2 hours. The cultured *Escherichia coli* was harvested via centrifugation at 1,800×g. The medium was removed therefrom. A 0.1 M citric acid buffer (pH 5.6) (150 µl) was added thereto, followed by sufficient mixing. The resultant was repeatedly subjected to ultrasonication on ice 3 times for 10 seconds (output: 4; duty: 70) using a ultrasonic disintegrator (UD-201, TOMY SEIKO Co., Ltd., Tokyo, Japan), followed by centrifugation at 20,000×g. The supernatant was transferred to a new centrifuge tube and designated as a crude enzyme liquid.

Figure 6:
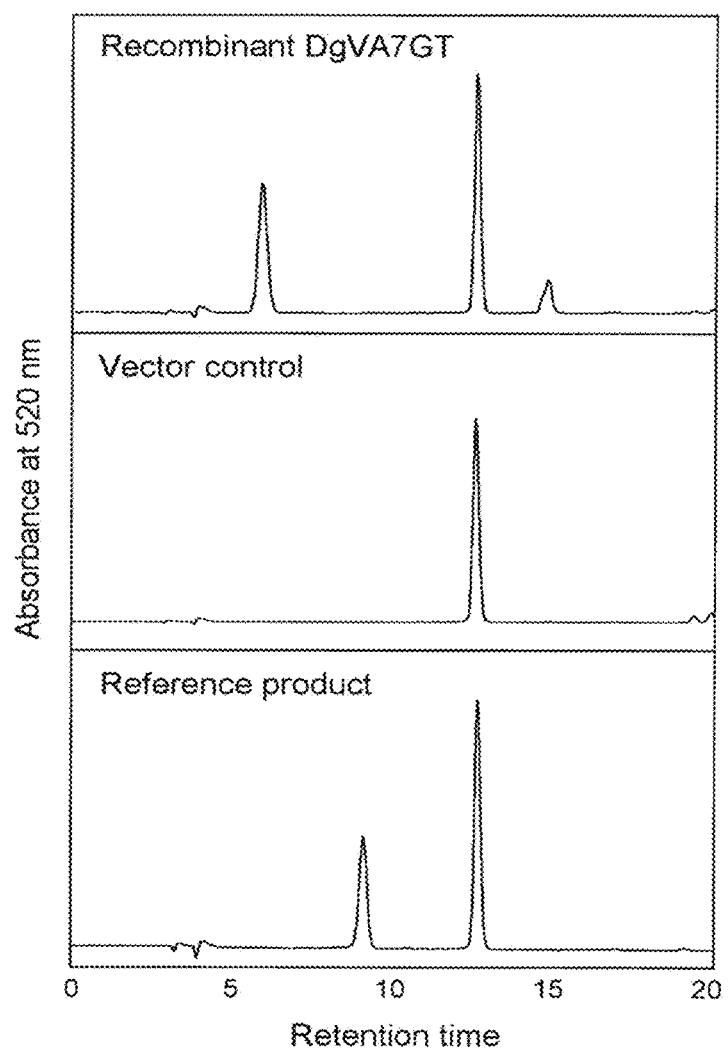
FIG. 6 shows HPLC analysis results indicating generation of a product other than cyanidin 3,5-O-β-diglucoside from cyanidin 3-O-β-glucoside as a result of glycosyl transfer reaction with the use of crude enzyme liquid obtained from *Escherichia coli* transformed with the delphinium-derived glycosyltransferase gene.

A reaction was induced in a reaction liquid containing the crude enzyme liquid (20 µl), a 0.1M citric acid buffer (pH 5.6) (20 µl), a cyanidin-3-O-β glucoside (5 µl), and 1-O-β-vanillyl glucose (5 µl) at 30° C. for 3 hours. Then, a 20% phosphoric acid aqueous solution (2.5 µl) was added thereto to terminate the reaction. The insoluble protein was removed via centrifugation at 20,000×g. Thereafter, the reaction product was confirmed by HPLC analysis. HPLC analysis was performed using a 1.5% phosphoric acid aqueous solution and methanol as eluents and a Wakopak Handy ODS column (4.6×250 mm, Wako Pure Chemical Industries, Ltd.). Separation was carried out with a linear gradient of 22% to 55% methanol at a flow rate of 1 ml/min (20 minutes). Peak generation was confirmed at a retention time that differed from the retention time at which peak generation was observed for cyanidin 3,5-O-β-diglucoside at the absorbance of a wavelength of 520 nm using a photodiode array detector (FIG. 6). It is known that an anthocyanin generated via modification of the 3 and 7 positions of anthocyanidin accumulates in blue delphinium petals. Therefore, the anthocyanin produced through the above reaction was presumed to be cyanidin 3,7-O-β-diglucoside. Meanwhile, no product was confirmed in the crude enzyme liquid obtained as a control from *Escherichia coli* transformed with a vector transfected with the LacZ gene provided with the kit. The results indicated that the gene having the nucleotide sequence (SEQ ID NO: 4) shown in FIG. 5 encodes an enzyme protein capable of transferring glucose to the 7 position of the anthocyanin skeleton using vanillyl glucose as a sugar donor.

Example 9

Analysis of expression levels of the gene encoding glycosyltransferase, levels of glycosyltransferase activity, and amounts of accumulated anthocyanin in stems, leaves, and petals at the four different development stages Time-dependent changes in the expression level of the gene encoding glycosyltransferase in a carnation (variety: "Beam Cherry") and organ specificity were examined. Petals at the four different development stages were used as samples for time-dependent analysis. Also, stems and leaves were used as samples for analysis of organ specificity.

RT-PCR was performed for expression analysis. cDNA was synthesized from total RNA (500 ng) extracted from each sample by the methods described in Examples 2 and 3. The primer and the reverse transcriptase used herein were an Oligo(dT)15 primer (Promega) and M-MLV ReverseTranscriptase (invitrogen), respectively. The following are the primers used for detection of expression of the relevant genes: carnation-derived UDP-glucose transferase (Dc3UGT): 5'-GGC ACC CAC GAC ACC ACC ATC CC-3' (SEQ ID NO: 21) and 5'-CAG GAT TGT CCA AGA TTA GAG TC-3' (SEQ ID NO: 22); carnation-derived vanillyl glucose transferase (DcVA5GT; the enzyme of the present invention): 5'-GAG GGA GTT TAC TCC AAA GAA G-3' (SEQ ID NO: 23) and 5'-CAC CAT GAG TTC GAC ATC TTC C-3' (SEQ ID NO: 24); and carnation-derived actin (DcActin): 5'-CCC TAT TGA GCA CGG TAT CGT CAC C-3' (SEQ ID NO: 25) and 5'-CAG CAC TTG TGG TGA GGG AGT AAC C-3' (SEQ ID NO: 26). The following are PCR conditions: 94° C. for 2 minutes and 27, 32, or 37 cycles of 94° C. 30 seconds, 60° C. for 30 seconds, and 72° C. for 20 seconds. Then, each PCR product was subjected to agarose gel electrophoresis for separation. The amounts of samples transcribed were compared based on the amounts of light used for UV irradiation of the PCR products.

Glycosyltransferase activity was examined using a crude enzyme extracted from each sample in the manner described in Example 1. Cyanidin 3-O-β-glucoside (final concentration: 200 µM) and 1-O-β-vanillyl glucose (final concentration: 1 mM) were used as a receptor and a sugar donor, respectively. The pH was adjusted to 5.6 with a citric acid buffer, followed by a glycosyltransferase reaction at 30° C. for 15 minutes. The reaction was terminated with phosphoric acid (final concentration: 1%), followed by centrifugation for the removal of insoluble matter. Then, the supernatant was analyzed by HPLC (see Example 1(3) for HPLC conditions). The pkat per 1 mg of a crude enzyme was calculated based on the HPLC area using cyanidin 3,5-O-β-diglucoside as a reference substance.

The amount of accumulated anthocyanin in petals was quantified by determining the absorbance at 520 nm of the extraction liquid obtained by extracting each sample (0.1 g) with 80% methanol containing 1% trifluoroacetic acid for 72 hours. The amount of anthocyanin per 1 g of each sample was calculated based on the absorbance of pelargonidin 3,5-diglucoside.

Figure 7:
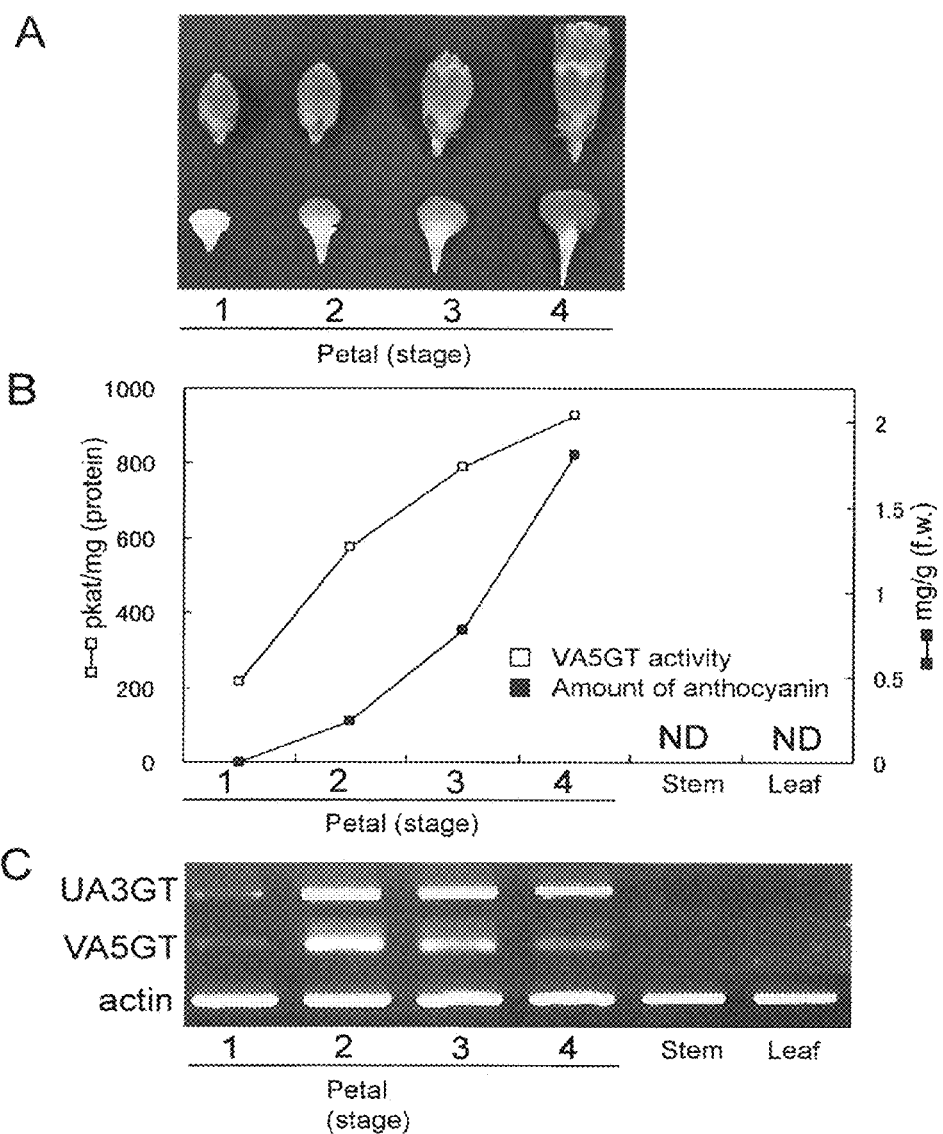
FIG. 7 shows carnation petals at four different development stages (A), analysis results of levels of glycosyltransferase activity and amounts of accumulated anthocyanin in stems, leaves, and petals at the four different development stages (B), and the expression levels of the gene encoding glycosyltransferase in stems, leaves, and petals at the four different development stages (C).

FIG. 7 shows the analysis results. These results indicate that the glycosylation gene is involved in synthesis of the carnation anthocyanin pigment in a carnation plant.

Example 5

(1) Synthesis of 1-O-β-p-hydroxybenzoyl Glucose

A vanillic acid glycosylation enzyme gene was amplified by PCR using PCR primers (DcA82atg: ATGGAGGAG- GATAAACAAAAGCC (SEQ ID NO: 27); and DcA82atgrt: ATGTGAAGTAACTTCTTCAATA (SEQ ID NO: 28)) designed based on the DNA sequence information of a homologous carnation glycosylation enzyme gene (DcUGTA82) (DDBJ accession No. AB294379) in the DDBJ database and template 3'-RACE cDNA synthesized in the manner described in Example 2. The amplified DNA was ligated to a pTrcHis2-TOPO vector (Invitrogen) using a pTrcHis2-TOPO TA expression Kit (Invitrogen) for transformation of the *Escherichia coli* JM109 strain. DNA was extracted from the transformed *Escherichia coli* to analyze the DNA nucleotide sequence in the above manner. Accordingly, the direction of cDNA introduction and the nonoccurrence of PCR-induced nucleotide substitution were confirmed.

The transformed *Escherichia coli* was seeded on an LB medium containing 50 ampicillin (5 ml), followed by shake culture at 30° C. for 14 hours. IPTG was added thereto to result in 1 mM, followed by shake culture at 16° C. for 2 hours. The cultured *Escherichia coli* was harvested via centrifugation at 1,800×g. The medium was removed therefrom. A pulverization buffer (0.1 M potassium phosphate, pH 7.5, 7 mM 2-mercaptoethanol) (150 µl) was added thereto, followed by sufficient mixing. The resultant was repeatedly subjected to ultrasonication on ice 3 times for 10 seconds (output: 4; duty: 70) using a ultrasonic disintegrator (UD-201, TOMY SEIKO Co., Ltd., Tokyo, Japan), followed by centrifugation at 20,000×g for. The supernatant was transferred to a new centrifuge tube and designated as a crude enzyme liquid.

A reaction was induced in a reaction liquid containing the crude enzyme liquid (20 µl), a pulverization buffer (0.1 M potassium phosphate, pH 7.5, 7 mM 2-mercaptoethanol) (20 W), 10 mM UDP-glucose (5 µl), and 10 mM vanillic acid or p-hydroxybenzoic acid (5 µl) at 30° C. for 3 hours. Then, a 20% phosphoric acid aqueous solution (2.5 µl) was added thereto to terminate the reaction. The insoluble protein was removed via centrifugation at 20,000×g. Thereafter, the reaction product was confirmed by HPLC analysis. HPLC analysis was performed using a 1.5% phosphoric acid aqueous solution and methanol as eluents and a Wakopak Handy ODS column (4.6×250 mm, Wako Pure Chemical Industries, Ltd.). Separation was carried out with a linear gradient of 22% to 60% methanol at a flow rate of 1 ml/min (20 minutes). A reaction product was confirmed using a photodiode array detector.

Figure 8:
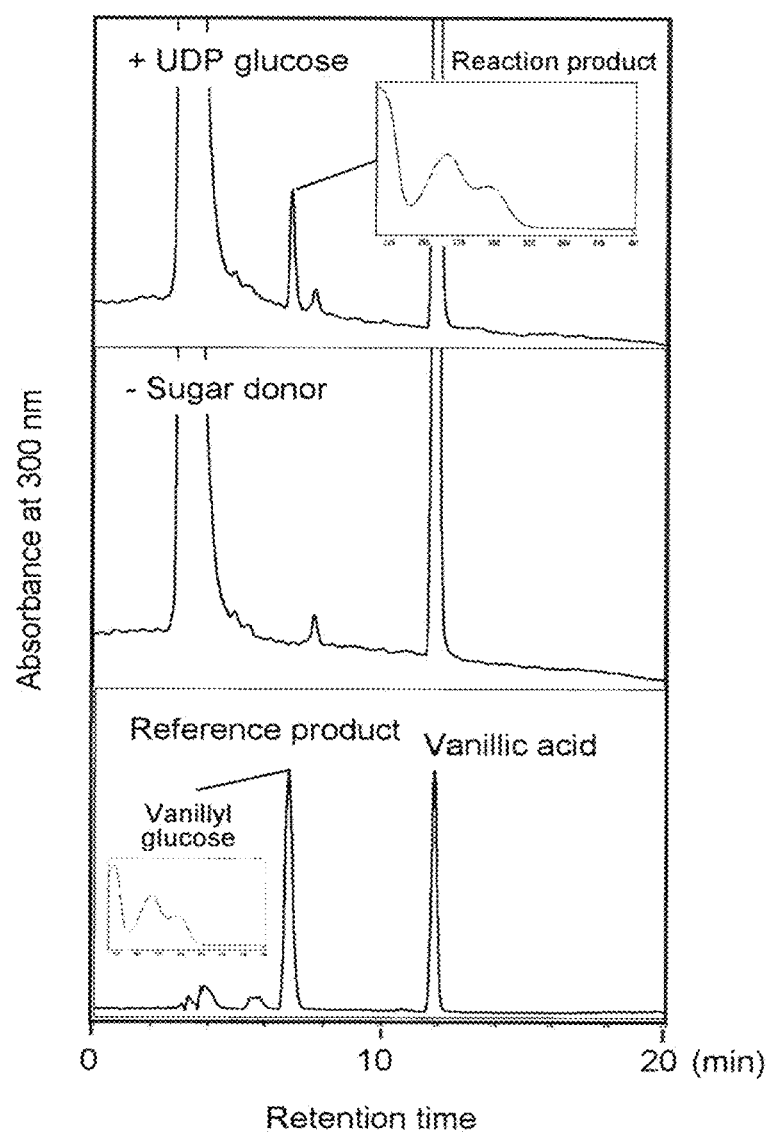
FIG. 8 shows HPLC analysis results indicating generation of 1-O-β-vanillyl glucose as a result of glycosyltransferase reaction with the use of vanillic acid as a substrate and UDP-glucose as a sugar donor.
Figure 9:
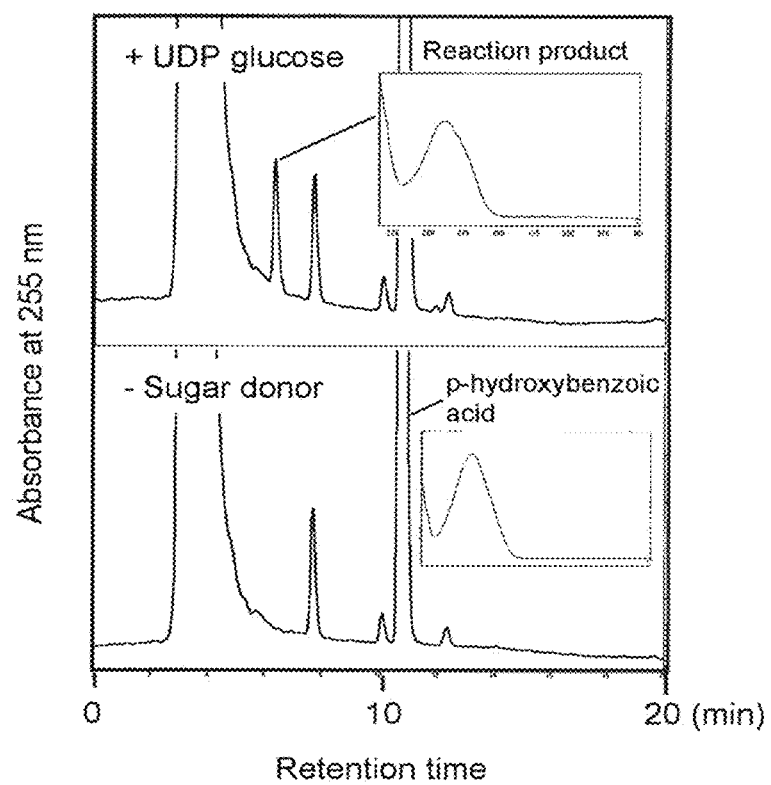
FIG. 9 shows HPLC analysis results indicating generation of a reaction product presumed to be 1-O-β-p-hydroxybenzoyl glucose as a result of glycosyl transfer reaction with the use of p-hydroxybenzoic acid as a substrate and UDP-glucose as a sugar donor.

When vanillic acid was used as a substrate, a new peak was found if the reaction mixture contained UDP-glucose as a sugar donor. (The upper chart shows a peak obtained with the addition of UDP-glucose and the middle chart shows a peak obtained without the addition of any sugar donor in FIG. 8). The compound was found to be identical to chemically synthesized 1-O-β-vanillyl glucose in terms of the retention time and the DAD spectrum. Therefore, it was demonstrated that the enzyme allows glucose to bind via an ester bond to an aromatic organic acid such as vanillic acid so as to result in the p form. Similarly, a reaction was induced using p-hydroxybenzoic acid as a substrate and UDP-glucose as a sugar donor. As a result, a new peak was detected on an HPLC chromatogram. (The upper chart shows a peak obtained with the addition of UDP-glucose and the middle chart shows a peak obtained without the addition of any sugar donor in FIG. 9). The obtained compound was presumed as 1-O-β-p-hydroxybenzoyl glucose.

Next, *Escherichia coli* transformed with DcUGTA82 was cultured in an LB medium (200 ml) at 30° C. for 14 hours. IPTG was added thereto so as to result in a final concentration of 1 mM. Culture was further carried out at 16° C. for 3 hours. The cultured cells of *Escherichia coli* were harvested by centrifugation at 6,000×g and suspended in a pulverize buffer (10 ml). The resultant was subjected to ultrasonication (output: 7; duty: 70) on ice for 30 minutes using a ultrasonic disintegrator, followed by centrifugation at 20,000×g. The supernatant was transferred to a new centrifuge tube and designated as a crude enzyme liquid. An enzyme reaction was carried out in a reaction liquid (30 ml in total) containing the crude enzyme liquid (10 ml), p-hydroxybenzoic acid (final concentration: 1 mM), and UDP-glucose (final concentration: 1 mM) at 30° C. for 3 hours. Then, phosphoric acid was added thereto to result in a final concentration for 1% so as to terminate the reaction, followed by centrifugation at 20,000×g for the removal of the insolubilized protein. 1-O-β-p-hydroxybenzoyl glucose contained in the supernatant was purified by flash chromatography (YFLC-AI-580, YAMAZEN corp.) using an ODS column (ODS-SM, 26×100 mm). The concentration of purified 1-O-β-p-hydroxybenzoyl glucose was calculated based on the absorbance at 255 nm for p-hydroxybenzoic acid using an ultraviolet-visible spectrophotometer.

(2) Detection of a Glycosyl Transfer Reaction Using 1-O-β-p-hydroxybenzoyl Glucose as a Sugar donor Glycosyltransferase activity was examined using a crude enzyme extracted from pink petals of a carnation (variety: "Beam Cherry") or petals of a delphinium (variety: "marine blue") in the manner described in Example 1. Cyanidin 3-O-β-glucoside (final concentration: 200 µM) and 1-O-β-p-hydroxybenzoyl glucose (final concentration: 1 mM) were used as a receptor and a sugar donor, respectively. The pH was adjusted to 5.6 with a citric acid buffer, followed by a glycosyltransferase reaction at 30° C. for 15 minutes. The reaction was terminated with phosphoric acid (final concentration: 1%), followed by centrifugation for the removal of insoluble matter. Then, the supernatant was analyzed by HPLC. HPLC analysis was carried out using a 1.5% phosphoric acid aqueous solution and methanol as eluents and a Wakopak Handy ODS column (4.6×250 mm, Wako Pure Chemical Industries, Ltd.). Separation was carried out at a flow rate of 1 ml/min with a linear gradient of 20% to 55% methanol (20 minutes). A reaction product was confirmed using a photodiode array detector.

Figure 10:
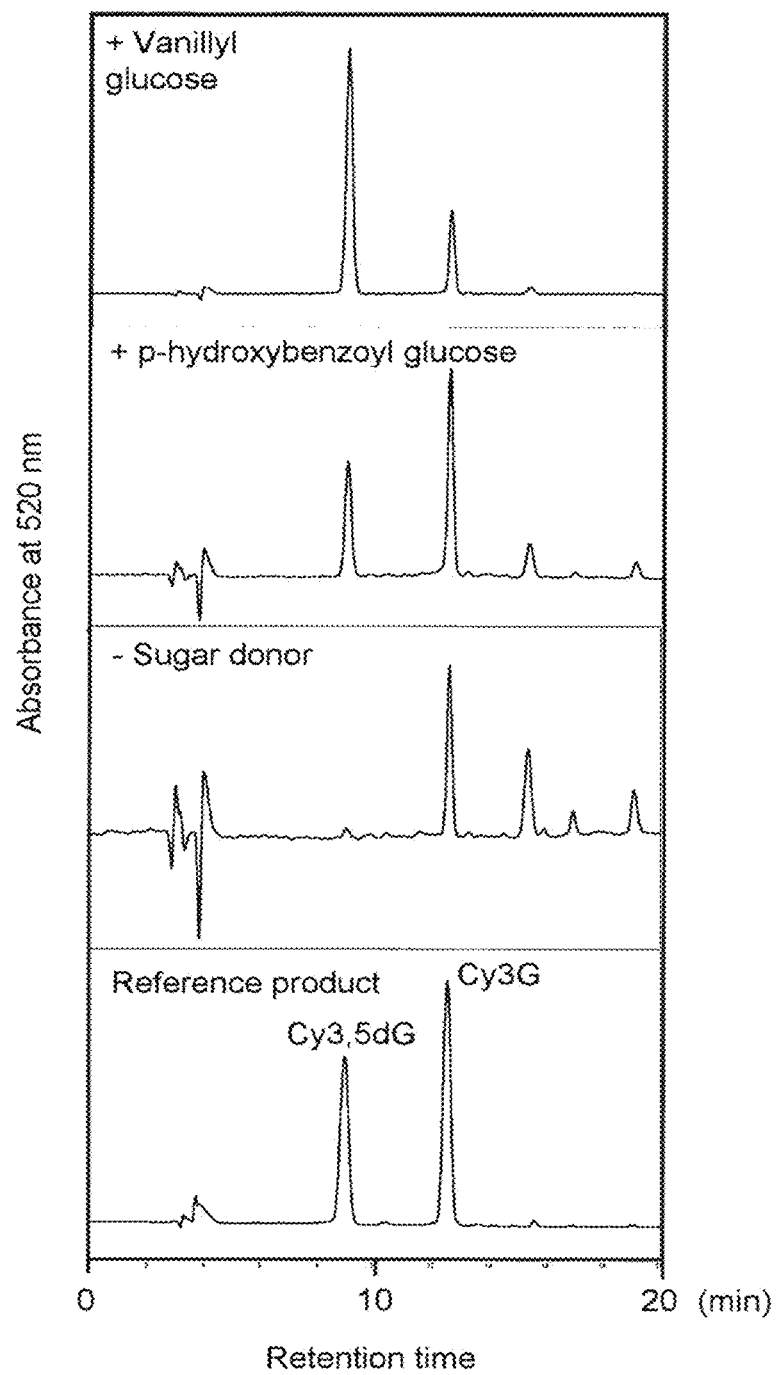
FIG. 10 shows HPLC analysis results indicating generation of cyanidin 3,5-O-β-diglucoside from cyanidin 3-O-β-glucoside as a result of glycosyl transfer reaction with the use of 1-O-β-p-hydroxybenzoyl glucose as a sugar donor induced in the presence of crude enzyme liquid obtained from carnation petals.
Figure 11:
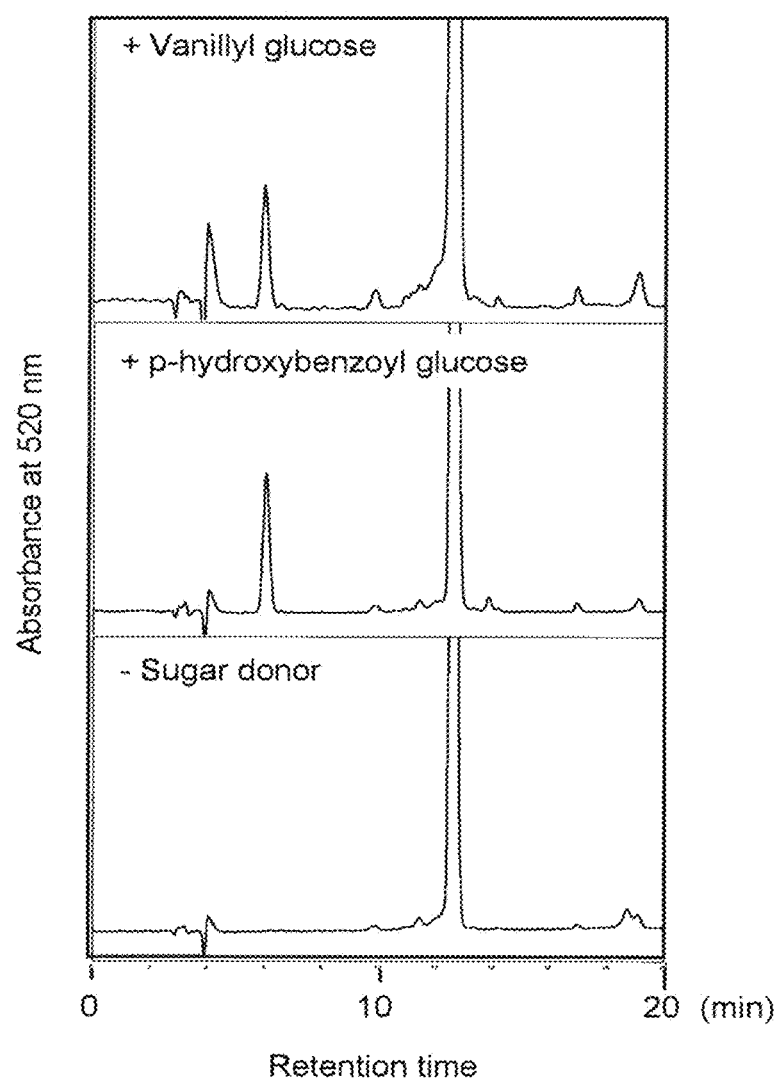
FIG. 11 shows HPLC analysis results indicating generation of cyanidin 3,5-O-β-diglucoside from cyanidin 3-O-β-glucoside as a result of glycosyl transfer reaction with the use of 1-O-β-p-hydroxybenzoyl glucose as a sugar donor induced in the presence of crude enzyme liquid obtained from delphinium petals.

As a result, the activity of a glycosylation enzyme on cyanidin 3-O-β-glucoside was confirmed in each case in which either a carnation or delphinium crude enzyme liquid was used. (FIG. 10: The upper chart shows a peak obtained with the addition of 1-O-β-vanillyl glucose to an enzyme obtained from carnation petals, the middle chart shows a peak obtained with the addition of 1-O-β-p-hydroxybenzoyl glucose to the same, and the bottom chart shows a peak obtained without the addition of any sugar donor to the same; FIG. 11: The upper chart shows a peak obtained with the addition of 1-O-β-vanillyl glucose to an enzyme obtained from delphinium petals, the middle chart shows a peak obtained with the addition of 1-O-β-p-hydroxybenzoyl glucose to the same, and the bottom chart shows a peak obtained without the addition of any sugar donor to the same.) The above results indicated that each of the above glycosylation enzymes can recognize 1-O-β-p-hydroxybenzoyl glucose as a sugar donor, in addition to 1-O-β-vanillyl glucose.

Figure 12:
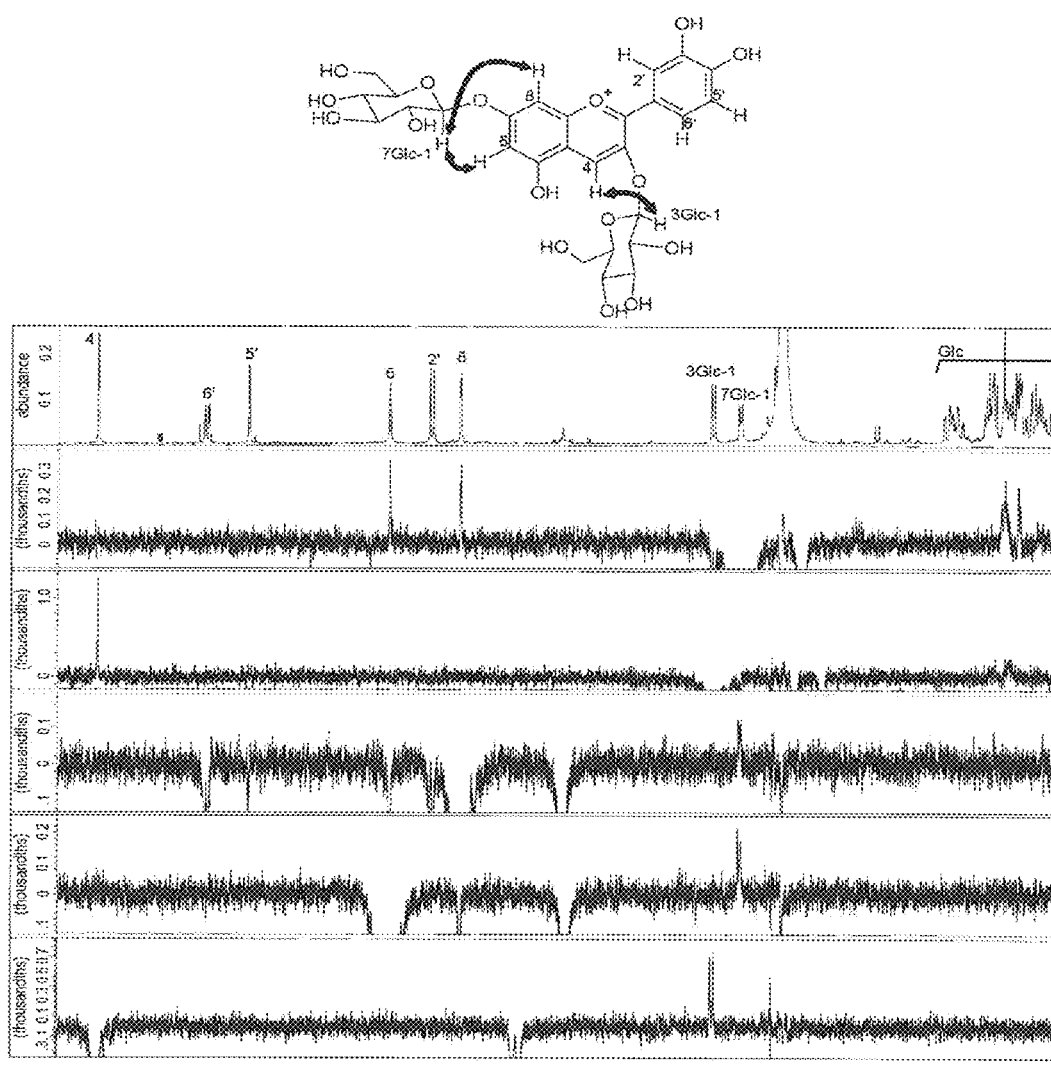
FIG. 12 shows NOE difference spectra for anthocyanin generated as a result of reaction with the use of a recombinant delphinium-derived glycosyltransferase.

(3) Confirmation of the Position of a Glucose Bond in Anthocyanin Generated Via a Reaction with the Use of *Delphinium*-Derived Glycosyltransferase A glycosyltransferase reaction was carried out using a recombinant delphinium-derived glycosyltransferase produced by the method described in Example 3 (2), cyanidin 3-O-β-glucoside as a sugar receptor, and 1-O-β-p-hydroxybenzoyl glucose as a sugar donor. A product obtained as a result of the reaction, which was presumed to be cyanidin 3,7-O-β-diglucoside, was purified by medium-pressure chromatography using an ODS column. The purified sample (dry weight: approximately 5 mg) was dissolved in heavy methanol for NOE difference spectrometry. FIG. 12 shows the results. In the chemical formula shown in the figure, each arrow indicates a correlation found as a result of NOE difference spectrometry. It was found that there is a correlation between C8 proton in the cyanidin skeleton and glucose 1' proton and that there is a correlation between C6 proton in the same and glucose 1' proton. The results indicate that anthocyanin generated through the glycosyl transfer reaction is cyanidin 3,7-diglucoside formed as a result of transfer of glucose to a hydroxyl group at the 7 position of cyanidin 3-glucoside.

Example 6

Variation of Glycosyl Transfer Reaction Using an Enzyme Purified from a Carnation and a Different Compound as a Sugar Donor An enzyme reaction was carried out at 30° C. for 15 minutes using an enzyme (135 ng) purified from pink petals of a carnation (variety: "Beam Cherry") by the method described in Example 2 ((1) and (2)), cyanidin 3-glucoside (200 µM), and a sugar donor (1-O-β-D-vanillyl glucose or any of 1-O-β-D-p-coumaryl glucose, 1-O-β-D-caffeyl glucose, 1-O-β-D-feruloyl glucose, and 1-O-β-D-sinapoyl glucose that had been enzymatically synthesized according to the method described in Matsuba Y et al., Plant Biotechnology vol. 25, No. 4 (2008) pp. 369-375) (500 µM) in a reaction solution adjusted to 30 µl with the addition of a citric acid buffer (pH 5.6). A 20% phosphoric acid aqueous solution was added to the reaction liquid so as to result in a final phosphoric acid concentration of 1%. Thus, the reaction was terminated, followed by centrifugation. The resulting supernatant was subjected to separation using a HPLC column (Chromolith SpeedROD, 4.6×50 mm, Merck), eluent A (a 1.5% phosphoric acid aqueous solution), and eluent B (a 90% methanol aqueous solution) with a linear gradient of 18% to 28% liquid B (flow rate: 3.0 ml/min, 520 nm) (5 minutes), followed by analysis. The relative activity of the enzyme on each sugar donor was determined by calculating the area of the reaction product (cyanidin 3,5-O-β-diglucoside) on an HPLC chromatogram at a wavelength of 505 nm. The results are listed in the table below.

TABLE 3

| | Relative activity of an enzyme on a sugar donor (when synthetic 1-O-β-vanillyl glucose is set as 100) |
|---|---|
| 1-O-β-vanillyl glucose (synthetic) | 100 |
| 1-O-β-D-p-coumaryl glucose (synthetic) | 350 |
| 1-O-β-D-caffeyl glucose (synthetic) | 464 |
| 1-O-β-D-feruloyl glucose (synthetic) | 1320 |
| 1-O-β-D-sinapoyl glucose (synthetic) | 793 |

INDUSTRIAL APPLICABILITY

A glycosylation reaction can be carried out using the sugar donating reagent of the present invention without a sugar nucleotide such as UDP-glucose. In addition, an enzyme capable of catalyzing a glycosyl transfer reaction using a sugar donor other than a sugar nucleotide can be provided using the glycosyltransferase and the glycosyltransferase gene of the present invention.

All publications, patents, and patent applications cited herein are incorporated herein by reference in their entirety.

The invention claimed is:

1. An isolated cDNA of a glycosyltransferase gene comprising cDNA that encodes a protein that is selected from the following (a) and (b):
   (a) a protein comprising the amino acid sequence set forth in SEQ ID NO: 1 or 3; and
   (b) a protein comprising an amino acid sequence derived from the amino acid sequence set forth in SEQ ID NO: 1 or 3 by deletion, substitution, insertion, or addition of one to five amino acids and having glycosyltransferase activity.

2. An isolated cDNA of a glycosyltransferase gene comprising cDNA that is one selected from the following (a) to (c):
   (a) cDNA comprising the nucleotide sequence set forth in SEQ ID NO: 2 or 4;
   (b) cDNA which hybridizes under stringent conditions to DNA comprising a nucleotide sequence complementary to the nucleotide sequence set forth in SEQ ID NO: 2 or 4 and encodes a protein having glycosyltransferase activity; and
   (c) cDNA comprising a degenerate isomer of the nucleotide sequence set forth in SEQ ID NO: 2 or 4,
   wherein the stringent conditions in (b) include a condition of washing at 42° C., 5×SSC, and 0.1% SDS after hybridization.

3. A recombinant vector comprising the cDNA of the glycosyltransferase gene according to claim 1.

4. A recombinant vector comprising the cDNA of the glycosyltransferase gene according to claim 2.

5. A transformant obtained by transforming a host cell using the recombinant vector according to claim 3.

6. A transformant obtained by transforming a host cell using the recombinant vector according to claim 4.

7. A transgenic plant transfected with the cDNA of the glycosyltransferase gene according to claim 1 or a progeny of the plant having the same properties as the plant.

8. A transgenic plant transfected with the cDNA of the glycosyltransferase gene according to claim 2 or a progeny of the plant having the same properties as the plant.

9. A method for producing a protein that is encoded by the cDNA of the glycosyltransferase gene according to claim 1, which comprises culturing a transformant obtained by transforming a host cell using a recombinant vector comprising the cDNA of the glycosyltransferase gene according to claim 1.

10. A method for producing a protein that is encoded by the cDNA of the glycosyltransferase gene according to claim 1, which comprises culturing a transformant obtained by transforming a host cell using a recombinant vector comprising the cDNA of the glycosyltransferase gene comprising cDNA that is one selected from the following (a) to (c):
   (a) cDNA comprising the nucleotide sequence set forth in SEQ ID NO: 2 or 4;
   (b) cDNA which hybridizes under stringent conditions to DNA comprising a nucleotide sequence complementary to the nucleotide sequence set forth in SEQ ID NO: 2 or 4 and encodes a protein having glycosyltransferase activity; and
   (c) cDNA comprising a degenerate isomer of the nucleotide sequence set forth in SEQ ID NO: 2 or 4,
   wherein the stringent conditions in (b) include a condition of washing at 42° C., 5×SSC, and 0.1% SDS after hybridization.

11. The cDNA of the glycosyltransferase gene of claim 2, wherein the stringent conditions of (b) further include washing at 50° C., 5×SSC, and 0.1% SDS after hybridization.

12. The cDNA of the glycosyltransferase gene of claim 2, wherein the stringent conditions of (b) further include washing at 65° C., 0.1×SSC, and 0.1% SDS after hybridization.

13. The method of claim 10, wherein the stringent conditions of (b) further include washing at 50° C., 5×SSC, and 0.1% SDS after hybridization.

14. The method of claim 10, wherein the stringent conditions of (b) further include washing at 65° C., 0.1×SSC, and 0.1% SDS after hybridization.

* * * * *